United States Patent
Yang et al.

(10) Patent No.: US 10,227,304 B2
(45) Date of Patent: Mar. 12, 2019

(54) MITOCHONDRIAL ALDEHYDE DEHYDROGENASE-2 MODULATORS AND METHODS OF USE THEREOF

(71) Applicant: The Board of Trustees of the Leland Stanford Junior University, Stanford, CA (US)

(72) Inventors: Wenjin Yang, Foster City, CA (US); Che-Hong Chen, Fremont, CA (US); Daria Mochly-Rosen, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 15/495,670

(22) Filed: Apr. 24, 2017

(65) Prior Publication Data

US 2017/0320828 A1  Nov. 9, 2017

Related U.S. Application Data

(62) Division of application No. 14/774,071, filed as application No. PCT/US2014/025993 on Mar. 13, 2014, now Pat. No. 9,670,162.

(60) Provisional application No. 61/782,071, filed on Mar. 14, 2013.

(51) Int. Cl.

| | |
|---|---|
| C07D 213/02 | (2006.01) |
| A61K 31/44 | (2006.01) |
| C07D 213/82 | (2006.01) |
| C07D 213/81 | (2006.01) |
| C07D 401/12 | (2006.01) |
| C07D 405/12 | (2006.01) |
| C07C 311/16 | (2006.01) |
| C07C 311/17 | (2006.01) |
| C07C 311/29 | (2006.01) |
| C07C 311/40 | (2006.01) |
| C07C 317/32 | (2006.01) |
| C07C 233/66 | (2006.01) |
| C07C 233/73 | (2006.01) |
| C07C 233/78 | (2006.01) |
| C07C 233/87 | (2006.01) |
| C07C 235/60 | (2006.01) |
| C07C 237/32 | (2006.01) |
| C07C 235/48 | (2006.01) |
| C07D 213/89 | (2006.01) |
| C07D 317/58 | (2006.01) |
| C07D 403/12 | (2006.01) |
| C07D 413/12 | (2006.01) |
| C07D 417/12 | (2006.01) |

(52) U.S. Cl.
CPC .......... *C07D 213/82* (2013.01); *C07C 233/66* (2013.01); *C07C 233/73* (2013.01); *C07C 233/78* (2013.01); *C07C 233/87* (2013.01); *C07C 235/48* (2013.01); *C07C 235/60* (2013.01); *C07C 237/32* (2013.01); *C07C 311/16* (2013.01); *C07C 311/17* (2013.01); *C07C 311/29* (2013.01); *C07C 311/40* (2013.01); *C07C 317/32* (2013.01); *C07D 213/81* (2013.01); *C07D 213/89* (2013.01); *C07D 317/58* (2013.01); *C07D 401/12* (2013.01); *C07D 403/12* (2013.01); *C07D 405/12* (2013.01); *C07D 413/12* (2013.01); *C07D 417/12* (2013.01); *C07C 2601/02* (2017.05); *C07C 2601/04* (2017.05); *C07C 2601/08* (2017.05)

(58) Field of Classification Search
None
See application file for complete search history.

(56) References Cited

U.S. PATENT DOCUMENTS

| | | | |
|---|---|---|---|
| 2,319,808 A | 5/1943 | Fernholz et al. | |
| 4,006,239 A | 2/1977 | Mayer et al. | |
| 4,861,891 A | 8/1989 | Saccomano et al. | |
| 4,992,417 A | 2/1991 | Katsoyannis | |
| 4,992,418 A | 2/1991 | Katsoyannis | |
| 5,004,743 A | 4/1991 | Young | |
| 5,200,534 A | 4/1993 | Rao | |
| 5,202,448 A | 4/1993 | Carver et al. | |
| 5,229,529 A | 7/1993 | Ueno et al. | |
| 5,260,323 A | 11/1993 | Baader et al. | |
| 5,283,253 A | 2/1994 | Holton et al. | |
| 5,294,637 A | 5/1994 | Chen et al. | |
| 5,360,806 A | 11/1994 | Toki et al. | |
| 5,374,605 A | 12/1994 | Hallenbach et al. | |
| 5,409,907 A | 4/1995 | Blasé et al. | |
| 5,415,869 A | 5/1995 | Straubinger et al. | |
| 5,474,978 A | 12/1995 | Bakaysa et al. | |
| 5,504,188 A | 4/1996 | Baker et al. | |
| 5,514,646 A | 5/1996 | Chance et al. | |
| 5,547,929 A | 9/1996 | Anderson, Jr. et al. | |

(Continued)

FOREIGN PATENT DOCUMENTS

| | | |
|---|---|---|
| CN | 1749415 | 3/2006 |
| EP | 1402887 | 3/2004 |

(Continued)

OTHER PUBLICATIONS

Yu et al. "Safrole Induces Apoptosis in Human Oral Cancer HSC-3 cell," J. Dent. Res 90(2) 168-174 (2011) First published online 2010.

(Continued)

*Primary Examiner* — Zinna Northington Davis
(74) *Attorney, Agent, or Firm* — Rudy J. Ng; Paula A. Borden; Bozicevic, Field & Francis LLP

(57) ABSTRACT

The present disclosure provides compounds of formula (I) that function as modulators of mitochondrial aldehyde dehydrogenase-2 (ALDH2) activity, and methods of preparing these compounds.

37 Claims, 12 Drawing Sheets

(56) References Cited

U.S. PATENT DOCUMENTS

| | | | |
|---|---|---|---|
| 5,650,486 A | 7/1997 | De Felippis | |
| 5,693,609 A | 12/1997 | Baker et al. | |
| 5,700,662 A | 12/1997 | Chance et al. | |
| 5,747,642 A | 5/1998 | De Felippis | |
| 5,922,675 A | 7/1999 | Baker et al. | |
| 5,952,297 A | 9/1999 | De Felippis et al. | |
| 6,034,054 A | 3/2000 | De Felippis et al. | |
| 6,235,791 B1 | 5/2001 | Breliere et al. | |
| 6,384,080 B1 | 5/2002 | Oku et al. | |
| 6,762,176 B1 | 7/2004 | Chabrier de Lassauniere et al. | |
| 6,780,883 B2 | 8/2004 | Booth et al. | |
| 6,900,338 B1 | 5/2005 | Haj-Yehia | |
| 6,939,882 B1 | 9/2005 | Cooke et al. | |
| 7,179,912 B2 | 2/2007 | Halbrook | |
| 7,569,572 B2 | 8/2009 | Bell et al. | |
| 7,750,025 B2 | 7/2010 | Sanofi-Aventis | |
| 7,790,753 B2 | 9/2010 | Sanofi-Aventis | |
| 7,799,782 B2 | 9/2010 | Munson | |
| 8,124,389 B2 | 2/2012 | Chen et al. | |
| 8,354,435 B2 | 1/2013 | Chen et al. | |
| 8,389,522 B2 | 3/2013 | Mochly-Rosen et al. | |
| 8,772,295 B2 | 7/2014 | Mochly-Rosen et al. | |
| 9,670,162 B2 * | 6/2017 | Yang | C07D 213/81 |
| 2002/0034783 A1 | 3/2002 | Meyers et al. | |
| 2002/0147192 A1 | 10/2002 | Bridger et al. | |
| 2002/0156281 A1 | 10/2002 | Booth et al. | |
| 2003/0100034 A1 | 5/2003 | Hunter | |
| 2004/0234622 A1 | 9/2004 | Muto et al. | |
| 2004/0242596 A1 | 12/2004 | Kim et al. | |
| 2005/0009812 A1 | 1/2005 | Seko et al. | |
| 2005/0171043 A1 | 8/2005 | Mochly-Rosen et al. | |
| 2005/0062308 A1 | 9/2005 | Wang et al. | |
| 2005/0215548 A1 | 9/2005 | Wang et al. | |
| 2005/0215645 A1 | 9/2005 | Muto et al. | |
| 2006/0106051 A1 | 5/2006 | Dyckman et al. | |
| 2006/0173050 A1 | 8/2006 | Liu et al. | |
| 2008/0021217 A1 | 1/2008 | Borchardt et al. | |
| 2008/0153926 A1 | 6/2008 | Mochly-Rosen et al. | |
| 2008/0200461 A1 | 8/2008 | Anderson et al. | |
| 2008/0214675 A1 | 9/2008 | Kehler et al. | |
| 2008/0317848 A2 | 12/2008 | Gramatte | |
| 2009/0082431 A1 | 3/2009 | Mochly-Rosen et al. | |
| 2009/0163545 A1 | 6/2009 | Goldfarb | |
| 2009/0203708 A1 | 8/2009 | Churlmin | |
| 2010/0113423 A1 | 5/2010 | Mochly-Rosen et al. | |
| 2011/0105602 A2 | 5/2011 | Mochly-Rosen et al. | |
| 2012/0101079 A1 | 4/2012 | Kuehnert et al. | |
| 2012/0258947 A1 | 10/2012 | Kuehnert et al. | |
| 2013/0053362 A1 | 2/2013 | Castro et al. | |
| 2013/0253010 A1 | 9/2013 | Chen et al. | |
| 2013/0267501 A1 | 10/2013 | Mochly-Rosen et al. | |

FOREIGN PATENT DOCUMENTS

| | | |
|---|---|---|
| EP | 1402888 | 3/2004 |
| EP | 1438973 | 7/2004 |
| EP | 1477186 | 11/2004 |
| EP | 1661572 | 5/2006 |
| EP | 1862552 | 1/2008 |
| EP | 2018863 | 1/2009 |
| EP | 2126574 | 10/2014 |
| FR | 1581075 | 9/1969 |
| JP | 57122039 | 7/1982 |
| JP | 01151546 | 6/1989 |
| JP | 203351 | 8/1989 |
| JP | 03184973 | 8/1991 |
| JP | H0 6502632 | 3/1994 |
| JP | 07505411 | 6/1995 |
| JP | 08208615 | 8/1996 |
| JP | 200526621 | 1/2005 |
| JP | 2012087116 | 5/2012 |
| WO | WO 199710223 | 5/1997 |
| WO | WO 199932444 | 7/1999 |
| WO | WO 199954284 | 10/1999 |
| WO | WO 200112604 | 2/2001 |
| WO | WO 200132928 | 5/2001 |
| WO | WO 200222599 | 3/2002 |
| WO | WO 2002053544 | 7/2002 |
| WO | WO 2002064568 | 8/2002 |
| WO | WO 2002096135 | 11/2002 |
| WO | WO 2003064391 | 8/2003 |
| WO | WO 2004005278 | 1/2004 |
| WO | WO 2004022523 | 3/2004 |
| WO | WO 2004089416 | 10/2004 |
| WO | WO 2005014550 | 2/2005 |
| WO | WO 2005057213 | 6/2005 |
| WO | WO 200507889 | 8/2005 |
| WO | WO 2005084392 | 9/2005 |
| WO | WO 2005011561 | 10/2005 |
| WO | WO 2005110422 | 11/2005 |
| WO | WO 2006091671 | 8/2006 |
| WO | WO 2006100502 | 9/2006 |
| WO | WO 2007034312 | 3/2007 |
| WO | WO 2007075783 | 7/2007 |
| WO | WO 2007110237 | 10/2007 |
| WO | WO 2007136707 | 11/2007 |
| WO | WO 2008002725 | 1/2008 |
| WO | WO 2008014497 | 1/2008 |
| WO | WO 2008021388 | 2/2008 |
| WO | WO 2008024497 | 2/2008 |
| WO | WO 2008071397 | 6/2008 |
| WO | WO 2008082487 | 7/2008 |
| WO | WO 2008082490 | 7/2008 |
| WO | WO 2009146555 | 12/2009 |
| WO | WO 2009156484 | 12/2009 |
| WO | WO 2010028175 | 3/2010 |
| WO | WO 2010062308 | 6/2010 |
| WO | WO 2010137351 | 12/2010 |
| WO | WO 2011044157 | 4/2011 |
| WO | WO 2012082862 | 6/2012 |
| WO | WO 2012088420 | 6/2012 |
| WO | WO 2012106534 | 8/2012 |
| WO | WO 2013006400 | 1/2013 |

OTHER PUBLICATIONS

Bukhitiarova et al. "Structure and Anti-inflammatory Activity of Isonicotinic and Nicotine Amides," *Pharmaceutical Chemistry Journal* 31(11): 597-598 (1997).

Chaturvedi, A. K. et. al.,"Effects of choline acetyltransferase inhibitors on the growth and differentiation of mouse neuroblastoma cells in culture", *Research Communications in Chemical Pathology and Pharmacology*, 37(3), 491-494 (1982).

Chung, W. K. et. el. "Synthesis and antitumor activities of potential antineoplastic agents. IV. Synthesis and antitumor activities of N-substituted-p-arsanilic acid", Yakhak Hoechi, 1971, 15(1), 16-23 & CAPLUS Accession No. 1974:115993.

Dimmock et al. "Evaluation of some mannich bases derived from substituted acetophenones against p-388 Lymphocyctic leukemia and on respiration in isolated rat liver mitochondria," *J. Pharmaceutical Sciences* 72(8) 887-894 (1983).

Gul, H. I. et. al. "Evaluation of the cytotoxicity of some mono-Mannich bases and their corresponding azine derivatives against androgen-independent prostate cancer cells", *Arzneim.-Forsch./Drug Res.*, 56(12), 850-855 (2006).

Huang, et al., "Antineoplastic activities of 2,3,4-chloro-substituted β-alkylaminopropiophenone derivatives in CF1 mice and in murine and human tumor cells" (Experimental Report), *Anti-Cancer Drugs*, 7, 613-620 (1996).

Kim et al. "Direct One-Pot Synthesis of Phenanthrenes via Suzuki-Miyaura Coupling/Aldol Condensation Cascade Reaction," *J. Org. Chem.* 73(2) 495-501 (2008).

Kondo et al. "[PPN][Ru3H(CO)11]/PCy3-Catalyzed Direct Addition ofFormyl Compounds to Alkenes," *Organometallics* 18(20) 4123-4127 (1999).

Leone et al., The effects of Melatonin and Melatonin Analogues on the P388, DLD-1 and MCF-7 Tumour Cell Lines, *NATO ASI series A: Life Sciences* 241-242 (1991).

Malyugina et al., "Antitumor action of some derivatives of adrenalones," *Pharmaceutical Chemistry Journal* 13(7): 56-58 (1979).

(56) References Cited

OTHER PUBLICATIONS

Messiha and Hughes "Liver Alcohol and Aldehyde Dehydrogenase Inhibition and Potentiation by histamine Agonists and Antagonists," *Clinical and Experimental Pharmacology and physiology* 6(3) 281-292 (1979).
Masu et al. "Phase-Dependent Emission of Naphthalene-Anthracene-Based Concave-Shaped Molecules," *Crystal Growth & Design* 6(9) 2086-2091 (2006).
Pradines et al. "In vitro increase in chloroquine accumulation in duced by dihydroethano- and ethenoanthracene derivatives in Plasmodium falciparum-parasitized erythrocyte," *Antimicrobial Agents and Chemotherapy* 46(7) 2061-2068 (2002).
Registry (STN) [online], Dec. 21, 1990 (searched date:), CAS Registry No. 131139-67-8.
Registry (STN) [online], Jun. 5, 2001(searched date:Dec. 19, 2013), CAS Registry No. 339335-56-7.
Ruechardt, C. et al., Organic peroxides. XIV. Thermal decomposition of polycyclic bridgehead peroxycarboxylates, Chemische Berichte, 114(8) 2769-2785 (1981).
Sudrik et al., Microwave Specific Wolff Rearrangement of α-Diazoketones and Its Relevance to the Nonthermal and Thermal Effect, Journal of Organic Chemistry 67(5) 1574-1579 (2002).
Weber "Decker-Oxidation 2-Substituierter N-Alkylpyridiniumverbindungen, 5 Mitt. Die Decker-Oxidation Von Homarin", *Archiv Der Pharmazie*, Wiley Verlag, Weinheim, 309(7): 664-669, XP001026698, ISSN: 0365-6233, DOI: 10.1002/ARDP.19763090810 (1976).
Werner, W. et. al. "Relations between the chemical structure of Mannich bases with and without nitrogen mustard groups and their cytostatic activisty against Ehrlich ascites carcinoma in mice," Arzneimittel-Forschung 20(2): 246-249 (1970).
Werner, W. et. al. "Structure-effect interactions in Mannich bases with and without nitrogen-mustard groups and some reduction products derived from β-aminoketones on the basis of a cancerostatic-3-step test with transplantation tumors", Pharmazie, 32(6): 341-347 & CAPLUS Accession No. 1977:545546 (1977).
White et al. "Specific sequestering agents for the actinides. 16. Synthesis and initial biological testing of polydentate oxohydroxypyridinecarboxylate ligands", *Journal of Medical Chemistry*, 31(1): 11-18 (1988).
Budas et al, "Activation of Aldehyde Dehydrogenase 2 (ALDH2) Confers Cardioprotection in Protein Kinase C Epsilon (PKCe) Knockout Mice," *Journal of Molecular and Cellular Cardiology* 48: 757-764 (2009).
Bukhitiarova et al. "Possiblities for search for New Analagesics in the series of Arylamides of Isoniotinic and Nocotine Acids," *Noi Akademii Nauk Ukraini* 8: 162-164 (1998).
Chen et al. "Interactive effects of lifetime alcohol consumption and alcohol and aldehyde dehydrogenase polymorphisms on esophageal cancer risks," *Int J Cancer*; 119(12)2827-2831 (2003).
Chen et al. "An Activator of Mutant and Wildtype Aldehyde Dehydrogenase Reduces Ischemic Damage to the Heart," *Science* 321 (5895): 1493-1495 (2008).
Chen et al. CAS: 149: 548594 (2008).
Cutshall et al. "Nicotinamide N-Oxides as CXCR2 Antagonists," *Bioorganic & Medicinal Chemisrty Letters*, 11: 1951-1954 (2001).
Davis et al. "Requirement for Pax6 in Corneal Morphogenesis: a Role in Adhesion," *Journal of Cell Science* 116 (11): 2157-2167 (2003).
Deng et al. "Distinct Expression Levis and patterns of Stem Cell Marker, Aldehyde Dehydrogenase Isoform 1 (ALDH1), in Human Epithelial Cancers," *PLos One* 5 (4) 1-11 (2010).
Feng et al. "Isolation and Characteriaztion of Human Salivary Glands for Stem Cell Transplantation to Reduce Radiation-Induced Hyposalivation, Radiotherapy and Oncology," *Radiotherapy and Oncology* 92:466-471 (2009).
Fernholz et al. "Stigmastadienone-22, 23-dibromide and related compounds," 1943: 40468 (1943).

Furata et al., "Efficient Synthesis of Phenanthridinone Derivatives via a Palladium-Catalyzed Coupling Process", *Org. Lett.* 9(2):183-186 (2007).
Gilman et al. "Organometallic Compounds in the Kolbe and Reimer-Tiemann Reactions," *J.of Organic Chemisrty* 1946: 2074 (1945).
Grigg et al., "Synthesis of Cyclopropanes by Intramolecular Attack of N-Nucleophiles on the Central Carbon of (π-Allyl)palladium Complexes," *Eur. J. Org. Chem.* 4:707-712. (2001).
Hashibe et al. "Evidence for an Important Role of Alcohol- and Aldehyde-Metabolizing Genes in Cancers of the Upper Aerodigestive Tract," *Cancer Epidemiol Biomarkers Prev.*; 15(4):696-703 (2006).
Hashimoto et al. "ALDH2 1510 G/A (Glu487Lys) polymorphism interaction with age in head and neck squamous cell carcinoma," *Tumour Biol*; 27(6):334-338 (2006).
Hess et al. "Functional Characterization of Highly Purified Human Hematopoietic Repopulating Cells Isolated According to Aldehyde Dehydrogenase Activity," *Blood* 104(6): 1648-1655 (2004).
Himel et al., "Fluorescent analogs of insecticides and synergists. Synthesis and reactions of active-site-directed fluorescent probes," *J. Arg. Food Chem* 19(6): 1175-1180 (1971).
Huigsen et al., CAS: 46: 45365 (1952).
Johnson et al. "Metabolism, Excretion, and Pharmacokinetics of 3-{[ 4-Tert-Butylbenzy)-(Pyridine-3-sulfonyl)-Amino]-Methyl-Phenoxy)-Acetic Acid, An Ep2recepto-Selective Prostaglandin E2 Agonist, In Male and Female Sprague-Dawley Rats," *Drug Metabolism and Disposition* 33(8): 1191-1201 (2005).
Katritzky et al. "N-Oxides and Related Compounds. Part X. The Hydrogenation pd some Polyridine 1-oxides," *J. Chem. Soc.*: 1-18 (1958).
Konoplitskaya et al., "Influence of Cyclopropylethyl-Containing Amines and Amides of the Isoenzyme Forms of Rat Liver Aldehyde Dehydrogenase," 28(1): 7-10. (1994).
Larson et al., "Disruption of the Coenzyme Binding Site and Dimer Interface Revealed in the Crystal Structure of Mitochondrial Aldehde Dehydrogenase Asian Variant," *The J. of Biological Chem* 280 (34): 30550-30556 (2005).
Li et al., "Mitochondrial Aldehyde Dehydrongenase-2(ALDH2) Glu554Lys Polymorphism Contributes to the Variation in Efficacy of Sublingual Nitroglycerin," *The J. of Clinical Investigation* 116 (2): 506-511 (2006).
Lombaert et al., "Rescue of Salivary Gland Function after Stem Cell Transplantation in Irradiated Glands," *PLos ONE* 3(4): 1-13 (2008).
Moussa et al. CAS: 146: 337551 (2007).
Nicoll-Griffith, "Stereoelectronic Model to Explain the Resolution of Enantiomeric Ibuprofen Amides on the Pirkle Chiral Stationary Phase," *J. of Chromatography* 402: 179-187 (1987).
Nicoll-Griffith's CAS: 107 141210 (1987).
Palacios, "Diuretic Action of New Sulfonmide Compounds," *Arch. Inst. Farmacol. Exptl.* 16(1): 1-18 (1964).
Paruszewski et al. "Anticonvulsant Activty of Benzylamides of Some Amino Acids and Heterocyclic Acids," *Protein and Peptide and Peptide Letters* 10(5): 475-482 (2003).
Perez-Miller et al. "Alda-1 is an Agonist and Chemical Chaperone for the common Human Aldehyde Dehydrogenase 2 Variant," *Nat Struct Mol Biol.* 17(2) 159-164 (2010).
Registry (STN) [online], Apr. 2, 2004 (searched date: Apr. 25, 2013), CAS Registry No. 670271-74-6.
Registry (STN) [online], Apr. 24, 2001 (searched date: Apr. 25, 2013), CAS Registry No. 332129-81-4.
Registry (STN) [online], Aug. 1, 2001 (searched date Apr. 25, 2013), CAS Registry No. 349615-88-9.
Registry (STN) [online], Jan. 2, 2001 (searched date: Apr. 25, 2013), CAS Registry No. 312526-08-2.
Registry (STN) [online], Jul. 25, 2006 (searched date: Apr. 25, 2013), CAS Registry No. 895680-72-5.
Registry (STN) [online], Jul. 25, 2006 (searched date: Apr. 25, 2013), CAS Registry No. 895680-64-5.
Registry (STN) [online], Jul. 26, 2001 (searched date: Apr. 25, 2013), CAS Registry No. 348604-08-0.
Registry (STN) [online], Jul. 29, 2001 (searched date: Apr. 25, 2013), CAS Regisrty No. 349438-38-6.

(56) References Cited

OTHER PUBLICATIONS

Registry (STN) [online], Jun. 7, 2004 (searched date: Apr. 25, 2013), CAS Registry No. 690210-80-1.
Registry (STN) [online], May 14, 2003 (searched date: Apr. 25, 2013), CAS Registry No. 514816-37-6.
Registry (STN) [online], Nov. 5, 2004 (searched date: Apr. 25, 2013), CAS Registry No. 775317-15-2.
Sato et al. "2-hydroxymethylnicotinic Acid Lactone, 2-Hydroxymethylpyridine-3-acetic Acid Lactone, and Some of their Derivatives," *Chem. Pharm. Bull.* 8(5) 427-435 (1960).
Satoh et al., "Comparison of the inhibitory action of synthetic capsaicin analogues with various NADH-ubiquinone oxidoreductases," *Biochimica et Biophysica Acta* 1273(1):21-30 (1996).
Seto et al, "Design and Synthesis of Novel 9-substituted-7-aryl-3,4,5,6-tetrahydro-2H-pyrido [4,3-b]- and [2,3-b]- and [2,3,-b]-1,5-oxazocin-6-ones as NK1 Antagonists," *Bioorganic & Medicinal Chemistry Letters* 15: 1479-1484 (2005).
STN: 11/16 RN 7500-45-0 (1984).
Tracy et al. "Product class 4: N-Arylalkanamides, ynamides, enamides, dienamides and allenamides," *Science of Synthesis* 2006:359121 (2005).
Weintraub et al., CAS: 143405804 (2005).
Yokoyama et al. "Genetic Polymorphisms of Alcohol and Aldehyde Dehydrogenases and Risk for Esophageal and Head and Neck Cancers," *Alcohol*; 35(3):175-185 (2005).
Zhang et al., "Automation of Fluorous Solid-Phase Extraction for Parallel Synthesis," *J. Comb. Chem.* 8(6):890-896 (1994).
Bohn et al. CAS: 121: 280094 (1994).
Borgna et al., "Preparation and Study of the Phytotoxic Activity of N-Aralkyl Substituted Amides," *Il Farmaco; Edizione Scientifica* 32 (11): 813-826 (1977).
Kharchenko et al. CAS: 150: 423065 (2008).
Patani et al., "Bioisosterism A Rational Approach in Drug Design," *Chem Rev.* 96: 3146-3176 (1996).
Stella and Nti-Addae, "Prodrug Strategies to Overcome Poor Water Solubility," *Department of Pharm Chem* 59:677-694 (2007).
Williams et al, "Drug Design and Relationship of Functional Groups to Pharmacologic Activity," *Foye's Principles of Medicinal Chemistry* 5: 50 and 59-61 (2002).
WU Toxicology 236: 1-6 (2007).
Chinn et al., "Isovanillyl Sweeteners. Amide Analogues of Dihydrochalcones," *J. Agric. Food Chem.*35(3) 409-411 (1987).
Dubois et al., "Dihydrochalcone Sweeteners. A Study of the Atypical Temporal Phenomena," *J. Med. Chem.* 24(4) 408-428 (1981).
Konoplitskaya et al., "Amides of benzoic and heterocyclic carboxylic acids are inhibitors of rat liver alcohol dehydrogenase," Pharmaceutical Chemistry Journal, 28 (1) 4-7 (1994).
Roe et al., "On the Utility of S-mesitylsulfinimines for the stereoselective synthesis of chiral amines and aziridines," Chem Commun 47 7491-7493 (2011).
Stavber et al. "Selectfluortm F-Teda-Bf4 Mediated Introduction of Perfluoroalkyl-Containing Groups in the Benzylic Position of Hexamethylbenzene," Acta Chim Slov. 49: 553-560 (2002).

\* cited by examiner

MITOCHONDRIAL ALDEHYDE DEHYDROGENASE-2 MODULATORS AND METHODS OF USE THEREOF

CROSS-REFERENCE

This application is a divisional of U.S. application Ser. No. 14/774,071, filed Sep. 9, 2015, now U.S. Pat. No. 9,670,162, issued Jun. 6, 2017, which is a National Phase entry of International Application No. PCT/US2014/025993, filed Mar. 13, 2014, which claims the benefit of U.S. Provisional Patent Application No. 61/782,071, filed Mar. 14, 2013, which applications are incorporated herein by reference in their entirety.

STATEMENT REGARDING FEDERALLY SPONSORED RESEARCH

This invention was made with Government support under contract AA011147 awarded by the National Institutes of Health. The Government has certain rights in the invention.

INTRODUCTION

Mitochondrial aldehyde dehydrogenase-2 (ALDH2) is encoded in the nuclear genome and is transported into mitochondria. ALDH2 is a tetrameric protein composed of four identical subunits, each consisting of 500 amino acid residues. This tetramer can be regarded as a dimer of dimers. The interface between monomers that form a dimer is different and more extensive than the interface between the two dimers that form the tetramer. Each subunit is composed of three main domains: the catalytic domain, the coenzyme or NAD⁺-binding domain, and the oligomerization domain.

Diseases and conditions associated with ALDH2 include ischemic stress, chronic free-radical associated diseases, acute free-radical associated diseases, insensitivity to nitroglycerin (e.g., in angina and heart failure), hypertension, diabetes, osteoporosis, cancer, Fanconi anemia, Alzheimer disease, Parkinson disease, alcoholism, alcohol intolerance, alcohol addiction, an alcohol abuse disorder, alcohol intoxication, alcohol dependence, alcohol poisoning, symptoms of alcohol consumption, and narcotic addition. Compounds of the present disclosure may a modulator of ALDH2, agonist of ALDH2, or antagonist of ALDH2. Agonists of ALDH2 are also useful for reducing the level in a subject of a compound such as ethanol, methanol, ethylene glycol monomethyl ether, polyvinyl chloride, xenogenic aldehydes, and biogenic aldehydes. Agonists of ALDH2 are also useful for reducing the level in a subject of a compound that, when ingested, absorbed, or inhaled, gives rise to an aldehyde substrate for ALDH2. Antagonists of ALDH2 are useful for treating or preventing disorders such as cancer, where the ALDH2 antagonist is used as an adjuvant to a standard cancer therapy. Antagonists of ALDH2 are also useful for treating or preventing alcoholism and narcotic addiction. The present disclosure addresses these needs.

SUMMARY

The present disclosure provides compounds that function as modulators of mitochondrial aldehyde dehydrogenase-2 (ALDH2) activity, and methods of preparing the compounds of the present disclosure.

The present disclosure relates to a compound of formula:

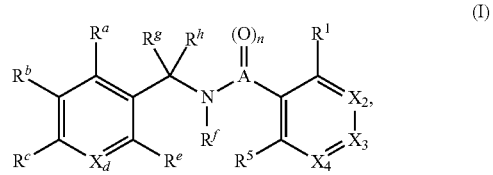

or a pharmaceutically acceptable salt, solvate, or prodrug thereof, wherein
A is selected from C and S;
$X_2$ is selected from $CR^2$, N, and NO;
$X_3$ is selected from $CR^3$, N, and NO;
$X_4$ is selected from $CR^4$, N, and NO;
$X_d$ is selected from $CR^d$, N, and NO;
$R^a$, $R^b$, $R^c$, $R^d$, and $R^e$ are independently selected from hydrogen, halogen, OH, $C_1$-$C_6$ alkyl, $C_1$-$C_6$ alkoxy, $NH_2$, $NO_2$, $NHR^6$, $NR^6R^6$, $S(O)_pR^6$, $C(O)R^6$, $C(O)OR^6$, $CF_3$, $CF_2H$, $CFH_2$, $OCF_3$, $OCF_2H$, and $OCFH_2$;
alternatively, $R^b$ and $R^c$ together form a 3-14 membered saturated, partially saturated, or unsaturated heterocycle containing one or more heteroatoms selected from N, O, and S; wherein the heterocycle is optionally substituted with one or more $R^8$;
$R^f$, $R^g$, and $R^h$ are independently selected from hydrogen and $C_1$-$C_6$ alkyl;
$R^1$, $R^2$, $R^3$, $R^4$, and $R^5$ are independently selected from hydrogen, halogen, OH, $C_1$-$C_6$ alkyl, $C_1$-$C_6$ alkoxy, $OR^7$, $NH_2$, $NO_2$, $NHR^7$, $NR^7R^7$, $S(O)_qR^7$, $C(O)R^7$, $C(O)OR^7$, $CF_3$, $CF_2H$, $CFH_2$, $OCF_3$, $OCF_2H$, and $OCFH_2$;
$R^6$ is selected from hydrogen and $C_1$-$C_6$ alkyl;
$R^7$ is selected from (a) hydrogen, (b) $C_1$-$C_6$ alkyl, (c) $C_2$-$C_6$ alkenyl, (d) $C_2$-$C_6$ alkynyl, (e) 3-14 membered saturated, partially saturated, or unsaturated carbocycle, and (f) 3-14 membered saturated, partially saturated, or unsaturated heterocycle containing one or more heteroatoms selected from N, O, and S;
wherein (b)-(f) optionally is substituted with one or more $R^8$;
$R^8$ is selected from (a) halogen, (b) OH, (c) $NO_2$, (c) $NH_2$, (d) C(O)OH, (e) $NH(C_1$-$C_6$ alkyl), (f) $N(C_1$-$C_6$ alkyl)$_2$, (g) C(O)O—($C_1$-$C_6$ alkyl), (h) $C_1$-$C_6$ alkyl, (i) $C_1$-$C_6$ alkoxy, (j) 3-14 membered saturated, partially saturated, or unsaturated carbocycle, (k) 3-14 membered saturated, partially saturated, or unsaturated heterocycle containing one or more heteroatoms selected from N, O, and S; and (l) =O;
wherein (e)-(k) optionally is substituted with one or more $R^9$;
$R^9$ is selected from halogen, OH, $C_1$-$C_6$ alkyl, $C_1$-$C_6$ alkoxy, C(O)OH, $NH_2$, $NH(C_1$-$C_6$ alkyl), $N(C_1$-$C_6$ alkyl)$_2$, $NO_2$, and $S(O)_q$—($C_1$-$C_6$ alkyl);
n is 1 or 2;
p is 1 or 2;
q is 0, 1, or 2;
provided that

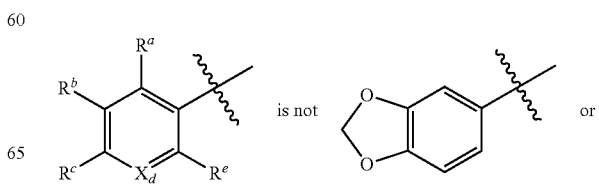

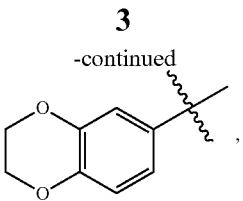

and
provided that the compound is not selected from:

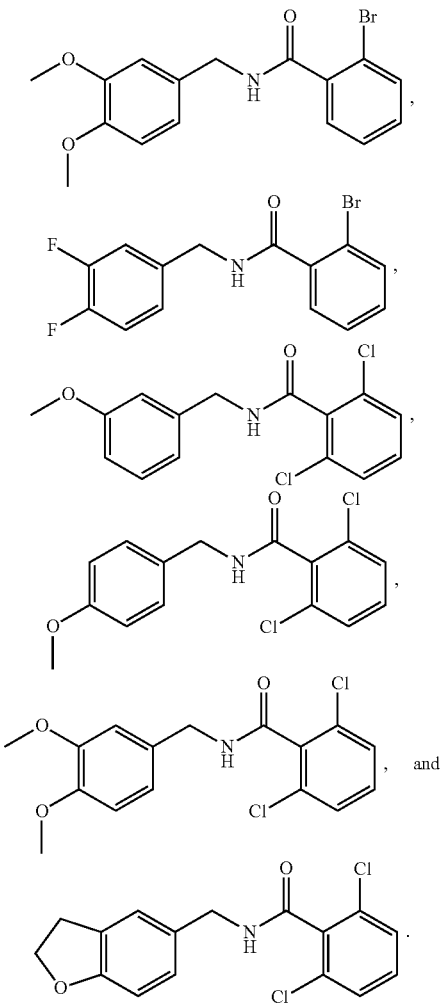

In one embodiment, the present disclosure relates to a compound of formula II:

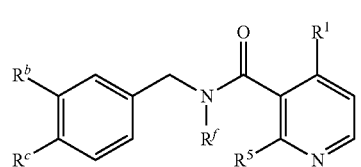

or a pharmaceutically acceptable salt, solvate, or prodrug thereof.

In one embodiment, the present disclosure relates to a compound of formula IV:

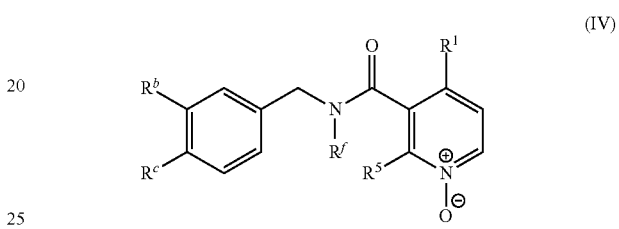

or a pharmaceutically acceptable salt, solvate, or prodrug thereof.

In one embodiment, the present disclosure relates to a compound of formulae I, II, III or IV, wherein $R^b$ is halogen, OH, or $C_1$-$C_6$ alkoxy. In another embodiment, $R^b$ is halogen.

In one embodiment, the present disclosure relates to a compound of formulae I, II, III or IV, wherein Rc is halogen, OH, or C1-C6 alkoxy. In another embodiment. Rc is C1-C6 alkoxy. In another embodiment, Rc is methoxy or ethoxy.

In one embodiment, the present disclosure relates to a compound of formula IIa:

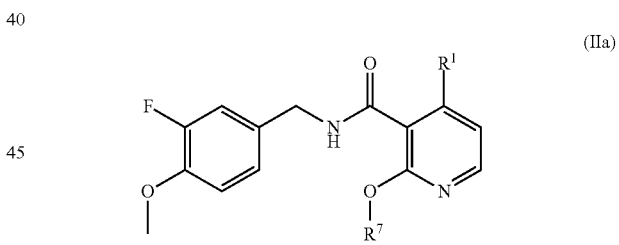

or a pharmaceutically acceptable salt, solvate, or prodrug thereof.

In one embodiment, the present disclosure relates to a compound of formula IIIa:

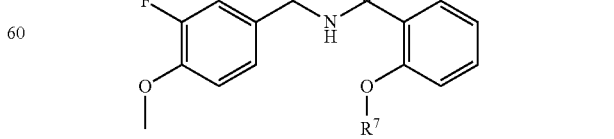

or a pharmaceutically acceptable salt, solvate, or prodrug thereof.

In one embodiment, the present disclosure relates to a compound of formula III:

In one embodiment, the present disclosure relates to a compound of formula IVa:

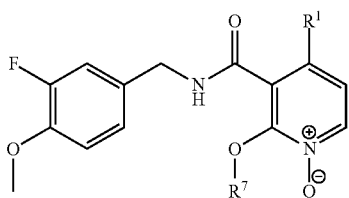
(IVa)

or a pharmaceutically acceptable salt, solvate, or prodrug thereof.

In one embodiment, the present disclosure relates to a compound of formula IIb:

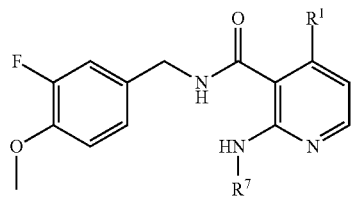
(IIb)

or a pharmaceutically acceptable salt, solvate, or prodrug thereof.

In one embodiment, the present disclosure relates to a compound of formula IIIb:

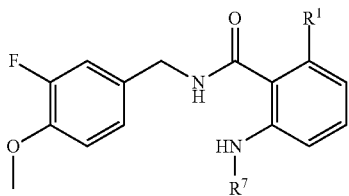
(IIIb)

or a pharmaceutically acceptable salt, solvate, or prodrug thereof.

In one embodiment, the present disclosure relates to a compound of formula IVb:

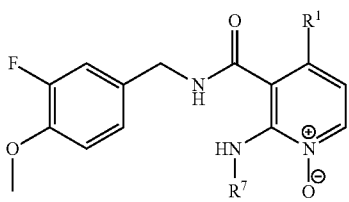
(IVb)

or a pharmaceutically acceptable salt, solvate, or prodrug thereof.

In one embodiment, the present disclosure relates to a compound of formulae I, II, III, IV, IIa, IIIa, IVa, IIb, IIIb, or IVb, wherein $R^1$ is halogen. In another embodiment, $R^1$ is F, Cl, or Br.

In one embodiment, the present disclosure relates to a compound of formulae I, II, III, IV, IIa. IIIa, IVa, IIb, IIIb, or IVb, wherein R7 is C1-C6 alky or 3-14 membered saturated, partially saturated, or unsaturated carbocycle; wherein the alkyl and carbocycle are optionally substituted with R8. In another embodiment, R7 is C1-C6 alkyl optionally substituted with R8.

In one embodiment, the present disclosure relates to a compound of formulae I, II, III, IV, IIa. IIIa, IVa, IIb, IIIb, or IVb, wherein R8 is selected from (a) 3-14 membered saturated, partially saturated, or unsaturated carbocycle, and (b) 3-14 membered saturated, partially saturated, or unsaturated heterocycle containing one or more heteroatoms selected from N, O, and S; wherein the carbocycle and heterocycle are optionally substituted with R9. In one embodiment, R9 is selected from halogen, OH, and C1-C6 alkoxy.

In one embodiment, the present disclosure relates to a compound of formula IIc:

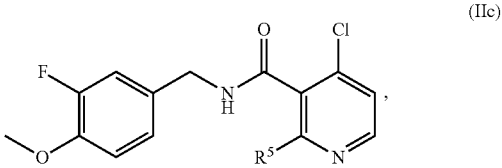
(IIc)

wherein $R^5$ is selected from halogen, $C_1$-$C_6$ alkyl, $OR^7$, and $NHR^7$, $R^7$ is selected from $C_1$-$C_6$ alkyl optionally substituted with $R^8$, $R^8$ is 3-14 membered saturated, partially saturated, or unsaturated carbocycle optionally substituted with $R^9$, and $R^9$ is $C_1$-$C_6$ alkyl, or a pharmaceutically acceptable salt, solvate, or prodrug thereof.

In one embodiment, the present disclosure relates to a compound of formula IIIc:

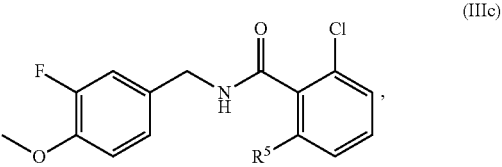
(IIIc)

wherein $R^5$ is selected from halogen, $C_1$-$C_6$ alkyl, $OR^7$, and $NHR^7$, $R^7$ is selected from $C_1$-$C_6$ alkyl optionally substituted with $R^8$, $R^8$ is 3-14 membered saturated, partially saturated, or unsaturated carbocycle optionally substituted with $R^9$, and $R^9$ is $C_1$-$C_6$ alkyl, or a pharmaceutically acceptable salt, solvate, or prodrug thereof.

In one embodiment, the present disclosure relates to a compound of formula IVc:

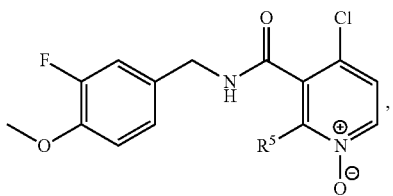

(IVc)

R⁵ is selected from halogen, $C_1$-$C_6$ alkyl, $OR^7$, and $NHR^7$,
$R^7$ is selected from $C_1$-$C_6$ alkyl optionally substituted with $R^8$,
$R^8$ is 3-14 membered saturated, partially saturated, or unsaturated carbocycle optionally substituted with $R^9$, and
$R^9$ is $C_1$-$C_6$ alkyl,
or a pharmaceutically acceptable salt, solvate, or prodrug thereof.

In one embodiment, the present disclosure relates to a compound selected from Table 1, and a pharmaceutically acceptable salt, solvate, or prodrug thereof.

In one embodiment, the present disclosure relates to a compound of formula (V):

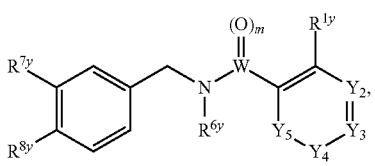

(V)

or a pharmaceutically acceptable salt, solvate, or prodrug thereof, wherein
W is selected from C and S;
$Y_2$ is selected from $CR^{2y}$, N, and NO;
$Y_3$ is selected from $CR^{3y}$, N, and NO;
$Y_4$ is selected from $CR^{4y}R^{4y}$ and $NR^{4y}$;
$Y_5$ is selected from $CR^{5y}R^{5y}$ and $NR^{5y}$;
$R^{1y}$, $R^{3y}$, $R^{4y}$, and $R^{5y}$ are independently selected from (a) hydrogen, (b) halogen, (c) OH, (d) $C_1$-$C_6$ alkyl, (e) $C_1$-$C_6$ alkoxy, (f) $OR^{9y}$, (g) $NH_2$, (h) $NO_2$, (i) $NHR^{9y}$, (j) $NR^{9y}R^{9y}$, (k) $S(O)_tR^{9y}$, (l) $C(O)R^{9y}$, (m) $C(O)OR^{9y}$, (n) $CF_3$, (o) $CF_2H$, (p) $CFH_2$, (q) $OCF_3$, (r) $OCF_2H$, (s) $OCFH_2$, (t) $(CH_2)_u$-3-14 membered saturated, partially saturated, or unsaturated carbocycle, and (u) $(CH_2)_v$-3-14 membered saturated, partially saturated, or unsaturated heterocycle containing one or more heteroatoms selected from N, O, and S;
wherein (t)-(u) optionally is substituted with $R^{10y}$;
alternatively, two $R^{4y}$ or two $R^{5y}$ together form a =O;
$R^{6y}$ is selected from hydrogen and $C_1$-$C_6$ alkyl;
$R^{7y}$ and $R^{8y}$ are independently selected from halogen, OH, $NO_2$, $NH_2$, C(O)OH, $NH(C_1$-$C_6$ alkyl), $N(C_1$-$C_6$ alkyl), C(O)O—($C_1$-$C_6$ alkyl), $C_1$-$C_6$ alkyl, $C_1$-$C_6$ alkoxy, $CF_3$, $CF_2H$, $CFH_2$, $OCF_3$, $OCF_2H$, and $OCFH_2$;
$R^{9y}$ is selected from halogen, OH, $C_1$-$C_6$ alkyl, $C_1$-$C_6$ alkoxy, C(O)OH, $NH_2$, $NH(C_1$-$C_6$ alkyl), $N(C_1$-$C_6$ alkyl)$_2$, $NO_2$, and $S(O)_t$—($C_1$-$C_6$ alkyl);
$R^{10y}$ is selected from halogen, OH, $C_1$-$C_6$ alkyl, $C_1$-$C_6$ alkoxy, C(O)OH, $NH_2$, $NH(C_1$-$C_6$ alkyl), $N(C_1$-$C_6$ alkyl)$_2$, $NO_2$, $CF_3$, $CF_2H$, $CFH_2$, $OCF_3$, $OCF_2H$, and $OCFH_2$ m is 1 or 2;
t is 0, 1, or 2;
u is 0, 1, 2, 3, 4, 5, or 6; and
v is 0, 1, 2, 3, 4, 5, or 6.

In one embodiment, the present disclosure relates to a compound of formula Va:

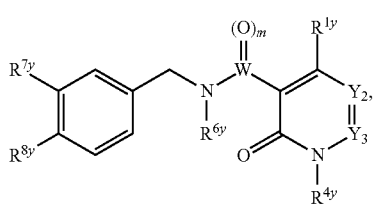

(Va)

or a pharmaceutically acceptable salt, solvate, or prodrug thereof.

In one embodiment, the present disclosure relates to a compound of formula Vb:

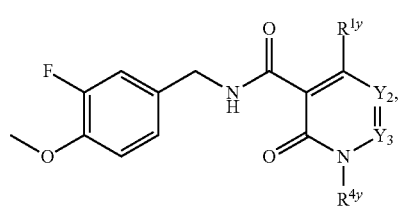

(Vb)

or a pharmaceutically acceptable salt, solvate, or prodrug thereof.

In one embodiment, the present disclosure relates to a compound of formula V, Va, and Vc, wherein $R^{4y}$ is selected from hydrogen, (CH2)u-3-14 membered saturated, partially saturated, or unsaturated carbocycle, or (CH2)v-3-14 membered saturated, partially saturated, or unsaturated heterocycle containing one or more heteroatoms selected from N, O, and S. In another embodiment, R4y is selected from (CH2)u-3-14 membered saturated, partially saturated, or unsaturated carbocycle.

In one embodiment, the present disclosure relates to a compound of formula Vc:

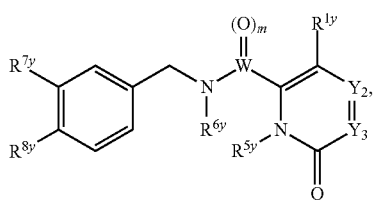

(Vc)

or a pharmaceutically acceptable salt, solvate, or prodrug thereof.

In one embodiment, the present disclosure relates to a compound of formula Vd:

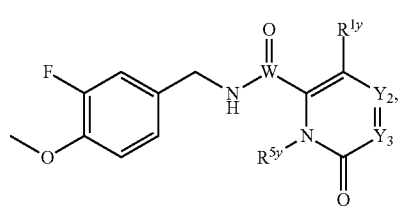

(Vd)

or a pharmaceutically acceptable salt, solvate, or prodrug thereof.

In one embodiment, the present disclosure relates to a compound of formulae V, Vc, and Vd, wherein $R^{5y}$ is selected from hydrogen, $(CH_2)_u$-3-14 membered saturated, partially saturated, or unsaturated carbocycle, or $(CH_2)_u$-3-14 membered saturated, partially saturated, or unsaturated heterocycle containing one or more heteroatoms selected from N, O, and S. In another embodiment, $R^{5y}$ is selected from $(CH_2)_u$-3-14 membered saturated, partially saturated, or unsaturated carbocycle.

In one embodiment, the present disclosure relates to a pharmaceutical composition comprising a compound of the present disclosure and a pharmaceutical acceptable excipient.

In one embodiment, the present disclosure relates a method of treating or preventing alcohol intolerance, alcohol addiction, an alcohol abuse disorder, alcohol intoxication, alcohol dependence, alcohol poisoning, or symptoms of alcohol consumption, the method comprising administering to a subject an effective amount of a compound or pharmaceutical composition of the present disclosure. In one embodiment, the alcohol poisoning is methanol poisoning. In one embodiment, the alcohol poisoning is acute alcohol poisoning. In one embodiment, the alcohol intoxication is acute alcohol intoxication. In one embodiment, the symptom of alcohol consumption is a hangover symptom. In another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the method of treating or preventing alcohol intolerance, alcohol addiction, an alcohol abuse disorder, alcohol intoxication, alcohol dependence, alcohol poisoning, or symptoms of alcohol consumption further comprises administering an opioid receptor antagonist. In one embodiment, the opioid receptor antagonist is naltrexone.

In one embodiment, the present disclosure relates to a method of sequestering aldehyde in a subject exposed to alcohol or aldehyde, comprising administering to the subject an effective amount of a compound or pharmaceutical composition of the present disclosure.

In one embodiment, the present disclosure relates to a method of reducing a level of an aldehyde present at a toxic level in a subject to below the toxic level, the method comprising administering to the subject an effective amount of a compound or pharmaceutical composition of the present disclosure, wherein the aldehyde is a biogenic aldehyde or a xenogenic aldehyde. In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (HNE). In one embodiment, the xenogenic aldehyde is an environmental aldehyde that is ingested or inhaled.

In one embodiment, the present disclosure relates to a method of treating or preventing an acute or a chronic free-radical associated disease in a subject, the method comprising administering to the subject an effective amount of a compound or pharmaceutical composition of the present disclosure. In one embodiment, the acute free-radical associated disease is selected from seizures and photo-damage to the skin.

In one embodiment, the present disclosure relates to a method of treating or preventing an ocular disorder in a subject, the method comprising administering to the subject an effective amount of a compound or pharmaceutical composition of the present disclosure. In one embodiment, the ocular disorder is selected from age-related cataracts, secondary cataracts, traumatic cataracts, congenital cataracts, age-related macular degeneration, and radiation cataracts.

In one embodiment, the present disclosure relates to a method of treating or preventing radiation-induced damage to epithelial cells in a subject, the method comprising administering to the subject a compound or pharmaceutical composition of the present disclosure. In one embodiment, the radiation-induced damage results in radiation dermatitis. In one embodiment, the compound or pharmaceutical composition is administered before the subject is exposed to ionizing radiation. In one embodiment, the compound or pharmaceutical composition is administered after the subject is exposed to ionizing radiation. In one embodiment, the compound or pharmaceutical composition is administered both before and after the subject is exposed to ionizing radiation. In one embodiment, the radiation-induced damage results in mucositis. In one embodiment, the compound or pharmaceutical composition is administered to a mucosal surface in the subject.

In one embodiment, the present disclosure relates to a method of reducing the likelihood that a subject will develop head and neck cancer, the method comprising administering to the subject an effective amount of a compound or composition of the present disclosure. In one embodiment, the subject is a habitual use of betel quid. In one embodiment, the composition is a toothpaste, a tooth gel, a tooth powder, a mouth rinse, a chewing gum, or a lozenge. In one embodiment, the present disclosure relates to a method of treating or preventing cancer in a subject, the method comprising administering: a) a compound or pharmaceutical composition of the present disclosure; and b) a cancer chemotherapeutic agent or ionizing radiation, wherein the compound or composition and the cancer chemotherapeutic agent, or compound or composition and the ionizing radiation, are administered in combined effective amounts to treat or prevent the cancer. In one embodiment, the chemotherapeutic agent is selected from an alkylating agent, a nitrosourea, an antimetabolite, an antitumor antibiotic, a plant (vinca) alkaloid, and a steroid hormone. In one embodiment, the alkylating agent is selected from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

In one embodiment, the ionizing radiation is administered via external beam radiation therapy or brachytherapy. In one embodiment, the administration of the compound or pharmaceutical composition reduces the amount of the chemotherapeutic agent or the ionizing radiation required to treat or prevent the cancer.

In one embodiment, the present disclosure relates to a method of reducing the likelihood that an a subject will develop oral cancer or lung cancer, the method comprising administering to the subject an effective amount of a compound or pharmaceutical composition of the present disclosure. In one embodiment, the compound or pharmaceutical composition is administered by a route selected from intramuscular, intravenous, subcutaneous, oral, and topical.

In one embodiment, the present disclosure relates to a method of synthesizing a compound of the present disclosure, or a pharmaceutically acceptable salt, solvate, or prodrug thereof.

In one embodiment, the present disclosure relates to a use of a compound or pharmaceutical composition as disclosed above for the manufacture of a medicament for treating or preventing alcohol intolerance, alcohol addiction, an alcohol abuse disorder, alcohol intoxication, alcohol dependence, alcohol poisoning, or symptoms of alcohol consumption.

In one embodiment, the alcohol poisoning is methanol poisoning.

In one embodiment, the alcohol poisoning is acute alcohol poisoning.

In one embodiment, the alcohol intoxication is acute alcohol intoxication.

In one embodiment, the symptom of alcohol consumption is a hangover symptom.

In one embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the use further comprises administering an opioid receptor antagonist.

In one embodiment, the opioid receptor antagonist is naltrexone.

In one embodiment, the present disclosure relates to a use of a compound or pharmaceutical composition as disclosed above for the manufacture of a medicament for sequestering aldehyde in a subject exposed to alcohol or aldehyde.

In one embodiment, the present disclosure relates to a use of a compound or pharmaceutical composition as disclosed above for the manufacture of a medicament for reducing a level of an aldehyde present at a toxic level in a subject to below the toxic level, wherein the aldehyde is a biogenic aldehyde or a xenogenic aldehyde.

In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (HNE).

In one embodiment, the xenogenic aldehyde is an environmental aldehyde that is ingested or inhaled.

In one embodiment, the present disclosure relates to a use of a compound or pharmaceutical composition as disclosed above for the manufacture of a medicament for treating or preventing an acute or a chronic free-radical associated disease in a subject.

In one embodiment, the acute free-radical associated disease is selected from seizures and photo-damage to the skin.

In one embodiment, the present disclosure relates to a use of a compound or pharmaceutical composition as disclosed above for the manufacture of a medicament for treating or preventing an ocular disorder in a subject.

In one embodiment, the ocular disorder is selected from age-related cataracts, secondary cataracts, traumatic cataracts, congenital cataracts, age-related macular degeneration, and radiation cataracts.

In one embodiment, the present disclosure relates to a use of a compound or pharmaceutical composition as disclosed above for the manufacture of a medicament for treating or preventing radiation-induced damage to epithelial cells in a subject.

In one embodiment, the radiation-induced damage results in radiation dermatitis.

In one embodiment, the compound or pharmaceutical composition is administered before the subject is exposed to ionizing radiation.

In one embodiment, the compound or pharmaceutical composition is administered after the subject is exposed to ionizing radiation.

In one embodiment, the compound or pharmaceutical composition is administered both before and after the subject is exposed to ionizing radiation.

In one embodiment, the radiation-induced damage results in mucositis.

In one embodiment, the compound or pharmaceutical composition is administered to a mucosal surface in the subject.

In one embodiment, the present disclosure relates to a use of a compound or pharmaceutical composition as disclosed above for the manufacture of a medicament for reducing the likelihood that a subject will develop head and neck cancer.

In one embodiment, the subject is a habitual use of betel quid.

In one embodiment, the composition is a toothpaste, a tooth gel, a tooth powder, a mouth rinse, a chewing gum, or a lozenge.

In one embodiment, the present disclosure relates to a use of a compound or pharmaceutical composition as disclosed above for the manufacture of a medicament for treating or preventing cancer in a subject, the use further comprises a cancer chemotherapeutic agent or ionizing radiation, wherein the compound or composition and the cancer chemotherapeutic agent, or compound or composition and the ionizing radiation, are administered in combined effective amounts to treat or prevent the cancer.

In one embodiment, the chemotherapeutic agent is selected from an alkylating agent, a nitrosourea, an antimetabolite, an antitumor antibiotic, a plant (vinca) alkaloid, and a steroid hormone.

In one embodiment, the alkylating agent is selected from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

In one embodiment, the ionizing radiation is administered via external beam radiation therapy or brachytherapy.

In one embodiment, the administration of the compound or pharmaceutical composition reduces the amount of the chemotherapeutic agent or the ionizing radiation required to treat or prevent the cancer.

In one embodiment, the present disclosure relates to a use of a compound or pharmaceutical composition as disclosed above for the manufacture of a medicament for reducing the likelihood that a subject will develop oral cancer or lung cancer.

In one embodiment, the compound or pharmaceutical composition is administered by a route selected from intramuscular, intravenous, subcutaneous, topical, and oral.

DETAILED DESCRIPTION

1. Compounds of the Disclosure

Figure 1:
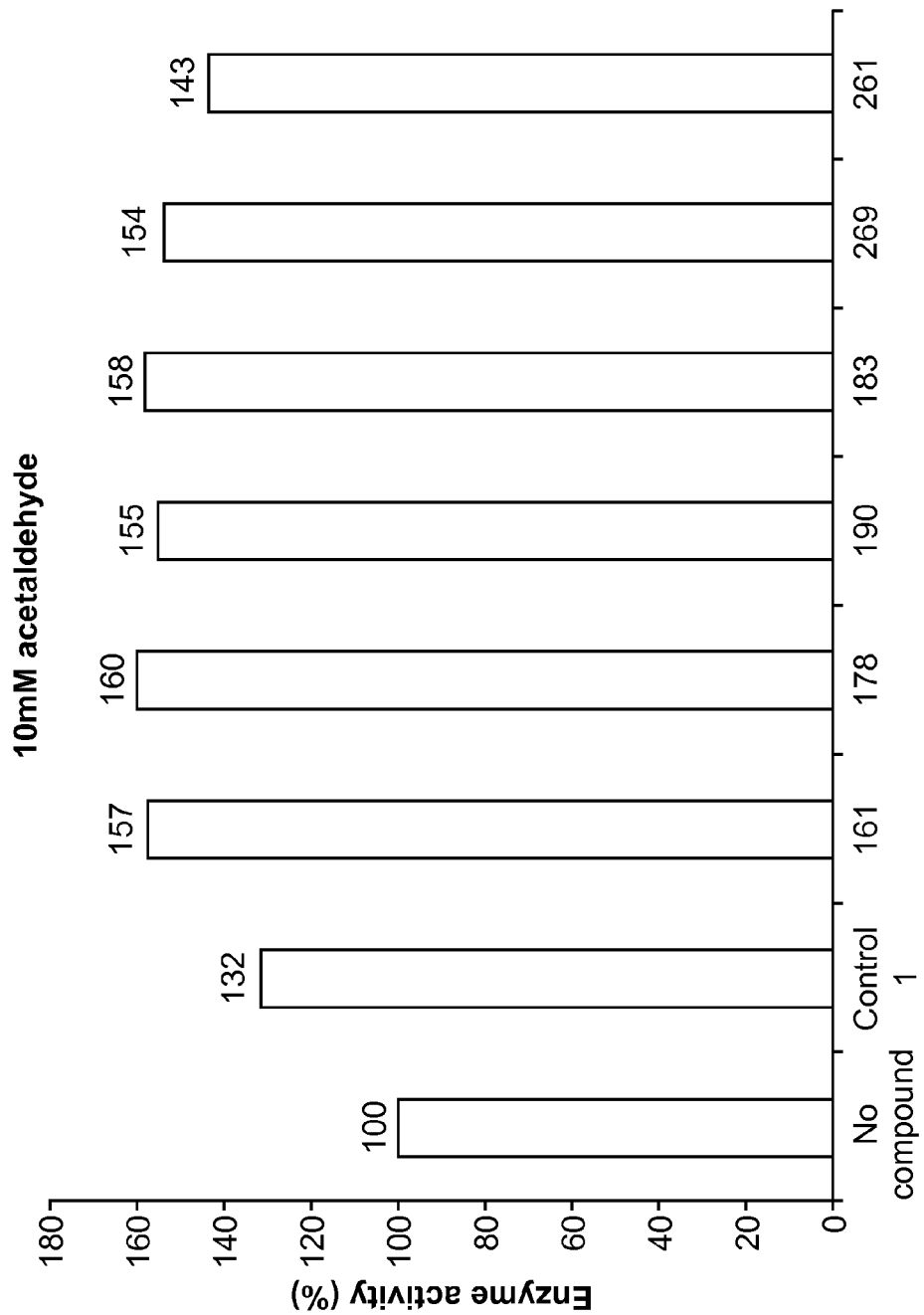
FIG. 1 is a graph showing the enzymatic activity (%) for compounds of the present disclosure tested in 10 mM acetaldehyde assay.

The present disclosure relates to a compound of formula:

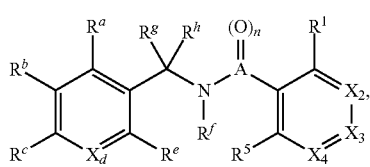

(I)

or a pharmaceutically acceptable salt, solvate, or prodrug thereof, wherein

A is selected from C and S;

$X_2$ is selected from $CR^2$, N, and NO;

$X_3$ is selected from $CR^3$, N, and NO;

$X_4$ is selected from $CR^4$, N, and NO;

$X_d$ is selected from $CR^d$, N, and NO;

$R^a$, $R^b$, $R^c$, $R^d$, and $R^e$ are independently selected from hydrogen, halogen, OH, $C_1$-$C_6$ alkyl, $C_1$-$C_6$ alkoxy, $NH_2$, $NO_2$, $NHR^6$, $NR^6R^6$, $S(O)_pR^6$, $C(O)R^6$, $C(O)OR^6$, $CF_3$, $CF_2H$, $CFH_2$, $OCF_3$, $OCF_2H$, and $OCFH_2$;

alternatively, $R^b$ and $R^c$ together form a 3-14 membered saturated, partially saturated, or unsaturated heterocycle containing one or more heteroatoms selected from N, O, and S; wherein the heterocycle is optionally substituted with one or more $R^8$;

$R^f$, $R^g$, and $R^h$ are independently selected from hydrogen and $C_1$-$C_6$ alkyl;

$R^1$, $R^2$, $R^3$, $R^4$, and $R^5$ are independently selected from hydrogen, halogen, OH, $C_1$-$C_6$ alkyl, $C_1$-$C_6$ alkoxy, $OR^7$, $NH_2$, $NO_2$, $NHR^7$, $NR^7R^7$, $S(O)_qR^7$, $C(O)R^7$, $C(O)OR^7$, $CF_3$, $CF_2H$, $CFH_2$, $OCF_3$, $OCF_2H$, and $OCFH_2$;

$R^6$ is selected from hydrogen and $C_1$-$C_6$ alkyl;

$R^7$ is selected from (a) hydrogen, (b) $C_1$-$C_6$ alkyl, (c) $C_2$-$C_6$ alkenyl, (d) $C_2$-$C_6$ alkynyl, (e) 3-14 membered saturated, partially saturated, or unsaturated carbocyclic, and (f) 3-14 membered saturated, partially saturated, or unsaturated heterocycle containing one or more heteroatoms selected from N, O, and S;

wherein (b)-(f) optionally is substituted with one or more $R^8$;

$R^8$ is selected from (a) halogen, (b) OH, (c) $NO_2$, (c) $NH_2$, (d) C(O)OH, (e) $NH(C_1$-$C_6$ alkyl), (f) $N(C_1$-$C_6$ alkyl)$_2$, (g) C(O)O—($C_1$-$C_6$ alkyl), (h) $C_1$-$C_6$ alkyl, (i) $C_1$-$C_6$ alkoxy, (j) 3-14 membered saturated, partially saturated, or unsaturated carbocycle, (k) 3-14 membered saturated, partially saturated, or unsaturated heterocycle containing one or more heteroatoms selected from N, O, and S; and (l) =O wherein (e)-(k) optionally is substituted with one or more $R^9$;

$R^8$ is selected from halogen, OH, $C_1$-$C_6$ alkyl, $C_1$-$C_6$ alkoxy, C(O)OH, $NH_2$, $NH(C_1$-$C_6$ alkyl), $N(C_1$-$C_6$ alkyl)$_2$, $NO_2$, and $S(O)_q$—($C_1$-$C_6$ alkyl);

n is 1 or 2;

p is 1 or 2;

q is 0, 1, or 2;

provided that

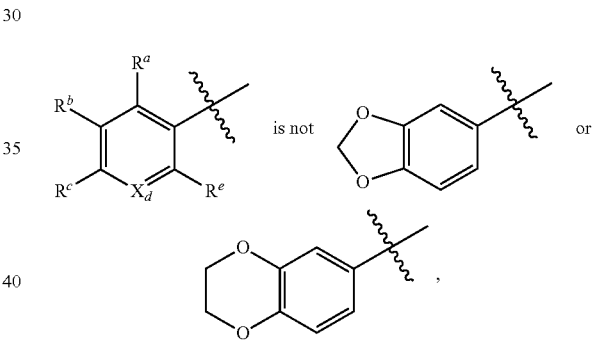

and provided that the compound is not selected from:

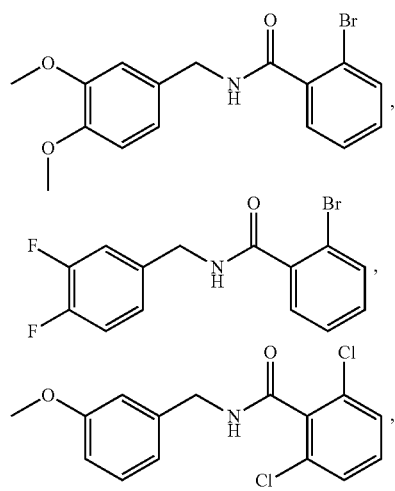

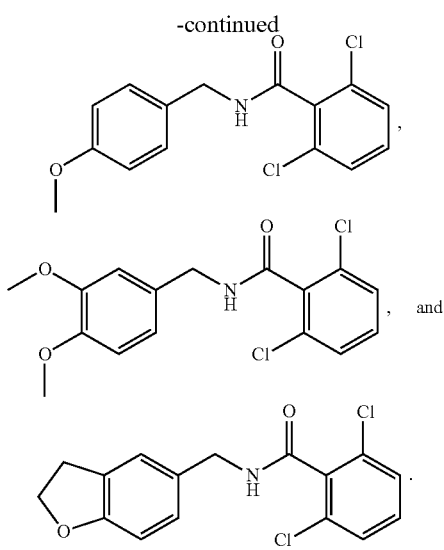

In one embodiment, the present disclosure relates to a compound of formula II:

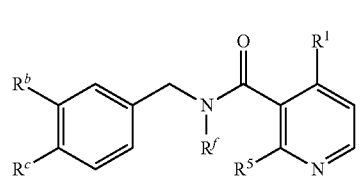
(II)

or a pharmaceutically acceptable salt, solvate, or prodrug thereof.

In one embodiment, the present disclosure relates to a compound of formula III:

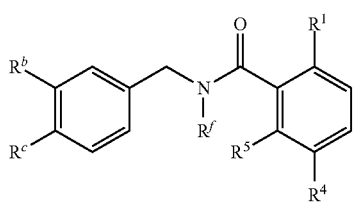
(III)

or a pharmaceutically acceptable salt, solvate, or prodrug thereof.

In one embodiment, the present disclosure relates to a compound of formula IV:

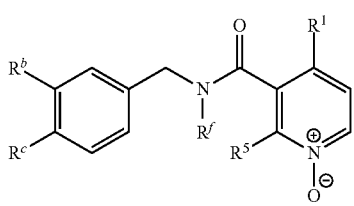
(IV)

or a pharmaceutically acceptable salt, solvate, or prodrug thereof.

In one embodiment, the present disclosure relates to a compound of formulae I, II, III or IV, wherein $R^b$ is halogen, OH, or $C_1$-$C_6$ alkoxy. In another embodiment, $R^b$ is halogen.

In one embodiment, the present disclosure relates to a compound of formulae I, II, III or IV, wherein $R^c$ is halogen, OH, or $C_1$-$C_6$ alkoxy. In another embodiment, $R^c$ is $C_1$-$C_6$ alkoxy. In another embodiment, $R^c$ is methoxy or ethoxy.

In one embodiment, the present disclosure relates to a compound of formula IIa:

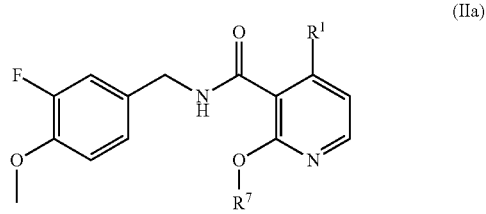
(IIa)

or a pharmaceutically acceptable salt, solvate, or prodrug thereof.

In one embodiment, the present disclosure relates to a compound of formula IIIa:

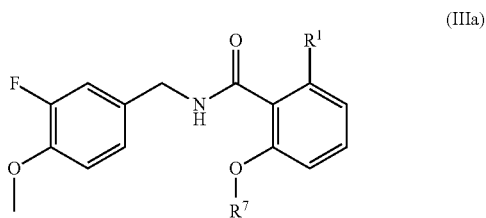
(IIIa)

or a pharmaceutically acceptable salt, solvate, or prodrug thereof.

In one embodiment, the present disclosure relates to a compound of formula IVa:

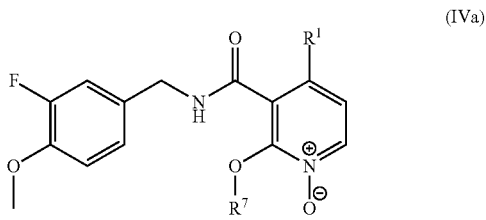
(IVa)

or a pharmaceutically acceptable salt, solvate, or prodrug thereof.

In one embodiment, the present disclosure relates to a compound of formula IIb:

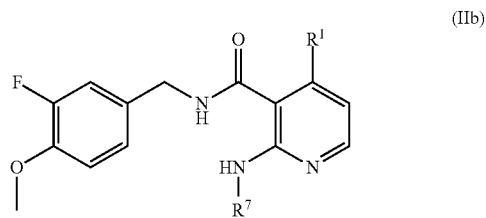
(IIb)

or a pharmaceutically acceptable salt, solvate, or prodrug thereof.

In one embodiment, the present disclosure relates to a compound of formula IIIb:

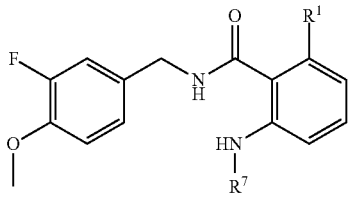

(IIIb)

or a pharmaceutically acceptable salt, solvate, or prodrug thereof.

In one embodiment, the present disclosure relates to a compound of formula IVb:

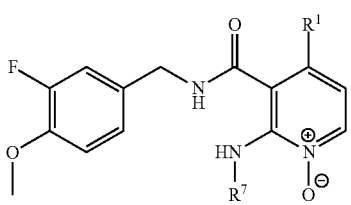

(IVb)

or a pharmaceutically acceptable salt, solvate, or prodrug thereof.

In one embodiment, the present disclosure relates to a compound of formulae I, II, III, IV, IIa, IIIa, IVa, IIb, IIIb, or IVb, wherein $R^1$ is halogen. In another embodiment, $R^1$ is F, Cl, or Br.

In one embodiment, the present disclosure relates to a compound of formulae I, II, III, IV, IIa, IIIa, IVa, IIb, IIIb, or IVb, wherein $R^7$ is $C_1$-$C_6$ alky or 3-14 membered saturated, partially saturated, or unsaturated carbocycle; wherein the alkyl and carbocycle are optionally substituted with $R^8$. In another embodiment, $R^7$ is $C_1$-$C_6$ alkyl optionally substituted with $R^8$.

In one embodiment, the present disclosure relates to a compound of formulae I, II, III, IV, IIa, IIIa, IVa, IIb, IIIb, or IVb, wherein $R^8$ is selected from (a) 3-14 membered saturated, partially saturated, or unsaturated carbocycle, and (b) 3-14 membered saturated, partially saturated, or unsaturated heterocycle containing one or more heteroatoms selected from N, O, and S; wherein the carbocycle and heterocycle are optionally substituted with $R^9$. In one embodiment, $R^9$ is selected from halogen, OH, and $C_1$-$C_6$ alkoxy.

In one embodiment, the present disclosure relates to a compound of formula IIc:

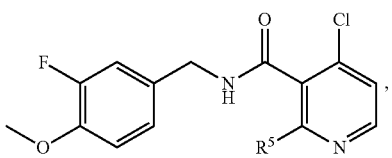

(IIc)

wherein
$R^5$ is selected from halogen, $C_1$-$C_6$ alkyl, $OR^7$, and $NHR^7$,
$R^7$ is selected from $C_1$-$C_6$ alkyl optionally substituted with $R^8$,
$R^8$ is 3-14 membered saturated, partially saturated, or unsaturated carbocycle optionally substituted with $R^9$, and
$R^9$ is $C_1$-$C_6$ alkyl,
or a pharmaceutically acceptable salt, solvate, or prodrug thereof.

In one embodiment, the present disclosure relates to a compound of formula IIIc:

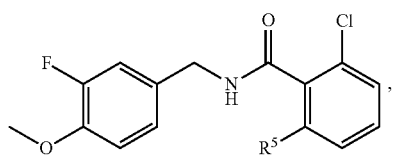

(IIIc)

wherein
$R^5$ is selected from halogen, $C_1$-$C_6$ alkyl, $OR^7$, and $NHR^7$,
$R^7$ is selected from $C_1$-$C_6$ alkyl optionally substituted with $R^8$,
$R^8$ is 3-14 membered saturated, partially saturated, or unsaturated carbocycle optionally substituted with $R^9$, and
$R^9$ is $C_1$-$C_6$ alkyl,
or a pharmaceutically acceptable salt, solvate, or prodrug thereof.

In one embodiment, the present disclosure relates to a compound of formula IVc:

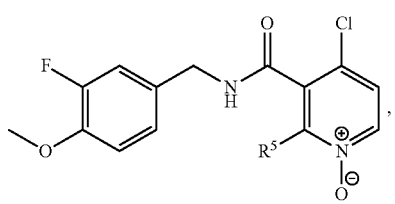

(IVc)

$R^5$ is selected from halogen, $C_1$-$C_6$ alkyl, $OR^7$, and $NHR^7$,
$R^2$ is selected from $C_1$-$C_6$ alkyl optionally substituted with $R^8$,
$R^8$ is 3-14 membered saturated, partially saturated, or unsaturated carbocycle optionally substituted with $R^9$, and
$R^9$ is $C_1$-$C_6$ alkyl,
or a pharmaceutically acceptable salt, solvate, or prodrug thereof.

In one embodiment, the present disclosure relates to a compound selected from Table 1, and a pharmaceutically acceptable salt, solvate, or prodrug thereof.

In one embodiment, the present disclosure relates to a compound of formula (V):

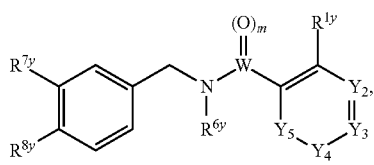

(V)

or a pharmaceutically acceptable salt, solvate, or prodrug thereof, wherein
W is selected from C and S;
$Y_2$ is selected from $CR^{2y}$, N, and NO;
$Y_3$ is selected from $CR^{3y}$, N, and NO;
$Y_4$ is selected from $CR^{4y}R^{4y}$ and $NR^{4y}$;
$Y_5$ is selected from $CR^{5y}R^{5y}$ and $NR^{5y}$;

$R^{1y}$, $R^{2y}$, $R^{3y}$, $R^{4y}$, and $R^{5y}$ are independently selected from (a) hydrogen, (b) halogen, (c) OH, (d) $C_1$-$C_6$ alkyl, (e) $C_1$-$C_6$ alkoxy, (f) $OR^{9y}$, (g) $NH_2$, (h) $NO_2$, (i) $NHR^{9y}$, (j) $NR^{9y}R^{9y}$, (k) $S(O)_tR^{9y}$, (l) $C(O)R^{9y}$, (m) $C(O)OR^{9y}$, (n) $CF_3$, (o) $CF_2H$, (p) $CFH_2$, (q) $OCF_3$, (r) $OCF_2H$, (s) $OCFH_2$, (t) $(CH_2)_u$-3-14 membered saturated, partially saturated, or unsaturated carbocycle, and (u) $(CH_2)_v$-3-14 membered saturated, partially saturated, or unsaturated heterocycle containing one or more heteroatoms selected from N, O, and S;

wherein (t)-(u) optionally is substituted with $R^{10y}$;
alternatively, two $R^{4y}$ or two $R^{5y}$ together form a =O;
$R^{6y}$ is selected from hydrogen and $C_1$-$C_6$ alkyl;
$R^{7y}$ and $R^{8y}$ are independently selected from halogen, OH, $NO_2$, $NH_2$, C(O)OH, $NH(C_1$-$C_6$ alkyl), $N(C_1$-$C_6$ alkyl)$_2$, C(O)O—($C_1$-$C_6$ alkyl), $C_1$-$C_6$ alkyl, $C_1$-$C_6$ alkoxy, $CF_3$, $CF_2H$, $CFH_2$, $OCF_3$, $OCF_2H$, and $OCFH_2$;
$R^{9y}$ is selected from halogen, OH, $C_1$-$C_6$ alkyl, $C_1$-$C_6$ alkoxy, C(O)OH, $NH_2$, $NH(C_1$-$C_6$ alkyl), $N(C_1$-$C_6$ alkyl)$_2$, $NO_2$, and $S(O)_t$—$C_1$-$C_6$ alkyl);
$R^{10y}$ is selected from halogen, OH, $C_1$-$C_6$ alkyl, $C_1$-$C_6$ alkoxy, C(O)OH, $NH_2$, $NH(C_1$-$C_6$ alkyl), $N(C_1$-$C_6$ alkyl)$_2$, $NO_2$, $CF_3$, $CF_2H$, $CFH_2$, $OCF_3$, $OCF_2H$, and $OCFH_2$ m is 1 or 2;
t is 0, 1, or 2;
u is 0, 1, 2, 3, 4, 5, or 6; and
v is 0, 1, 2, 3, 4, 5, or 6.

In one embodiment, the present disclosure relates to a compound of formula Va:

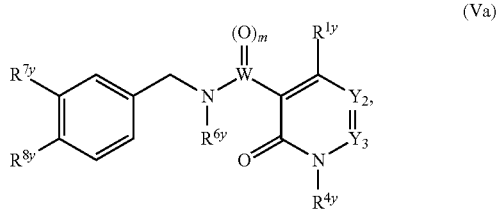

(Va)

or a pharmaceutically acceptable salt, solvate, or prodrug thereof.

In one embodiment, the present disclosure relates to a compound of formula Vb:

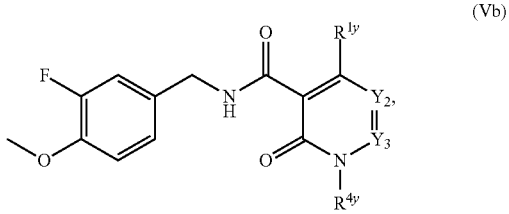

(Vb)

or a pharmaceutically acceptable salt, solvate, or prodrug thereof.

In one embodiment, the present disclosure relates to a compound of formula V, Va, and Vc, wherein $R^{4y}$ is selected from hydrogen, $(CH_2)_u$-3-14 membered saturated, partially saturated, or unsaturated carbocycle, or $(CH_2)_v$-3-14 membered saturated, partially saturated, or unsaturated heterocycle containing one or more heteroatoms selected from N, O, and S. In another embodiment, $R^{4y}$ is selected from $(CH_2)_u$-3-14 membered saturated, partially saturated, or unsaturated carbocycle.

In one embodiment, the present disclosure relates to a compound of formula Vc:

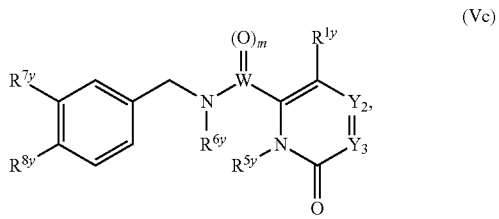

(Vc)

or a pharmaceutically acceptable salt, solvate, or prodrug thereof.

In one embodiment, the present disclosure relates to a compound of formula Vd:

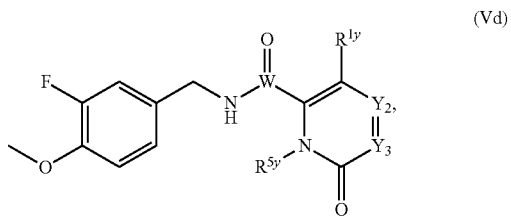

(Vd)

or a pharmaceutically acceptable salt, solvate, or prodrug thereof.

In one embodiment, the present disclosure relates to a compound of formulae V, Vc, and Vd, wherein $R^{5y}$ is selected from hydrogen, $(CH_2)_u$-3-14 membered saturated, partially saturated, or unsaturated carbocycle, or $(CH_2)_v$-3-14 membered saturated, partially saturated, or unsaturated heterocycle containing one or more heteroatoms selected from N, O, and S. In another embodiment, $R^{5y}$ is selected from $(CH_2)_u$-3-14 membered saturated, partially saturated, or unsaturated carbocycle.

In one embodiment, the present disclosure relates to a pharmaceutical composition comprising a compound of the present disclosure and a pharmaceutical acceptable excipient.

In one embodiment, the present disclosure relates a method of treating or preventing alcohol intolerance, alcohol addiction, an alcohol abuse disorder, alcohol intoxication, alcohol dependence, alcohol poisoning, or symptoms of alcohol consumption, the method comprising administering to a subject an effective amount of a compound or pharmaceutical composition of the present disclosure. In one embodiment, the alcohol poisoning is methanol poisoning. In one embodiment, the alcohol poisoning is acute alcohol poisoning. In one embodiment, the alcohol intoxication is acute alcohol intoxication. In one embodiment, the symptom of alcohol consumption is a hangover symptom. In another embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the method of treating or preventing alcohol intolerance, alcohol addiction, an alcohol abuse disorder, alcohol intoxication, alcohol dependence, alcohol poisoning, or symptoms of alcohol consumption further comprises administering an opioid receptor antagonist. In one embodiment, the opioid receptor antagonist is naltrexone.

In one embodiment, the present disclosure relates to a method of sequestering aldehyde in a subject exposed to alcohol or aldehyde, comprising administering to the subject an effective amount of a compound or pharmaceutical composition of the present disclosure.

In one embodiment, the present disclosure relates to a method of reducing a level of an aldehyde present at a toxic level in a subject to below the toxic level, the method comprising administering to the subject an effective amount of a compound or pharmaceutical composition of the present disclosure, wherein the aldehyde is a biogenic aldehyde or a xenogenic aldehyde. In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (HNE). In one embodiment, the xenogenic aldehyde is an environmental aldehyde that is ingested or inhaled.

In one embodiment, the present disclosure relates to a method of treating or preventing an acute or a chronic free-radical associated disease in a subject, the method comprising administering to the subject an effective amount of a compound or pharmaceutical composition of the present disclosure. In one embodiment, the acute free-radical associated disease is selected from seizures and photo-damage to the skin.

In one embodiment, the present disclosure relates to a method of treating or preventing an ocular disorder in a subject, the method comprising administering to the subject an effective amount of a compound or pharmaceutical composition of the present disclosure. In one embodiment, the ocular disorder is selected from age-related cataracts, secondary cataracts, traumatic cataracts, congenital cataracts, age-related macular degeneration, and radiation cataracts.

In one embodiment, the present disclosure relates to a method of treating or preventing radiation-induced damage to epithelial cells in a subject, the method comprising administering to the subject a compound or pharmaceutical composition of the present disclosure. In one embodiment, the radiation-induced damage results in radiation dermatitis. In one embodiment, the compound or pharmaceutical composition is administered before the subject is exposed to ionizing radiation. In one embodiment, the compound or pharmaceutical composition is administered after the subject is exposed to ionizing radiation. In one embodiment, the compound or pharmaceutical composition is administered both before and after the subject is exposed to ionizing radiation. In one embodiment, the radiation-induced damage results in mucositis. In one embodiment, the compound or pharmaceutical composition is administered to a mucosal surface in the subject.

In one embodiment, the present disclosure relates to a method of reducing the likelihood that a subject will develop head and neck cancer, the method comprising administering to the subject an effective amount of a compound or composition of the present disclosure. In one embodiment, the subject is a habitual use of betel quid. In one embodiment, the composition is a toothpaste, a tooth gel, a tooth powder, a mouth rinse, a chewing gum, or a lozenge.

In one embodiment, the present disclosure relates to a method of treating or preventing cancer in a subject, the method comprising administering: a) a compound or pharmaceutical composition of the present disclosure; and b) a cancer chemotherapeutic agent or ionizing radiation, wherein the compound or composition and the cancer chemotherapeutic agent, or compound or composition and the ionizing radiation, are administered in combined effective amounts to treat or prevent the cancer. In one embodiment, the chemotherapeutic agent is selected from an alkylating agent, a nitrosourea, an antimetabolite, an antitumor antibiotic, a plant (vinca) alkaloid, and a steroid hormone. In one embodiment, the ionizing radiation is administered via external beam radiation therapy or brachytherapy. In one embodiment, the administration of the compound or pharmaceutical composition reduces the amount of the chemotherapeutic agent or the ionizing radiation required to treat or prevent the cancer.

In one embodiment, the present disclosure relates to a method of reducing the likelihood that a subject will develop oral cancer or lung cancer, the method comprising administering to the subject an effective amount of a compound or pharmaceutical composition of the present disclosure. In one embodiment, the compound or pharmaceutical composition is administered by a route selected from intramuscular, intravenous, subcutaneous, oral, and topical.

In one embodiment, the present disclosure relates to a method of synthesizing a compound of the present disclosure, or a pharmaceutically acceptable salt, solvate, or prodrug thereof.

In one embodiment, the present disclosure relates to a use of a compound or pharmaceutical composition as disclosed above for the manufacture of a medicament for treating or preventing alcohol intolerance, alcohol addiction, an alcohol abuse disorder, alcohol intoxication, alcohol dependence, alcohol poisoning, or symptoms of alcohol consumption.

In one embodiment, the alcohol poisoning is methanol poisoning.

In one embodiment, the alcohol poisoning is acute alcohol poisoning.

In one embodiment, the alcohol intoxication is acute alcohol intoxication.

In one embodiment, the symptom of alcohol consumption is a hangover symptom.

In one embodiment, the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

In one embodiment, the use further comprises administering an opioid receptor antagonist.

In one embodiment, the opioid receptor antagonist is naltrexone.

In one embodiment, the present disclosure relates to a use of a compound or pharmaceutical composition as disclosed above for the manufacture of a medicament for sequestering aldehyde in a subject exposed to alcohol or aldehyde.

In one embodiment, the present disclosure relates to a use of a compound or pharmaceutical composition as disclosed above for the manufacture of a medicament for reducing a level of an aldehyde present at a toxic level in a subject to below the toxic level, wherein the aldehyde is a biogenic aldehyde or a xenogenic aldehyde.

In one embodiment, the biogenic aldehyde is acetaldehyde, malondialdehyde (MDA), 3,4-dihydroxypheylacetaldehyde (DOPAL), 3,4-dihydroxyphenylglycolaldehye (DOPEGAL), hexanal, acrolein, glyoxal, crotonaldehyde, trans-2-nonenal, 4-oxo-2-nonenal, or 4-hydroxy-2-nonenal (HNE).

In one embodiment, the xenogenic aldehyde is an environmental aldehyde that is ingested or inhaled.

In one embodiment, the present disclosure relates to a use of a compound or pharmaceutical composition as disclosed above for the manufacture of a medicament for treating or preventing an acute or a chronic free-radical associated disease in a subject.

In one embodiment, the acute free-radical associated disease is selected from seizures and photo-damage to the skin.

In one embodiment, the present disclosure relates to a use of a compound or pharmaceutical composition as disclosed above for the manufacture of a medicament for treating or preventing an ocular disorder in a subject.

In one embodiment, the ocular disorder is selected from age-related cataracts, secondary cataracts, traumatic cataracts, congenital cataracts, age-related macular degeneration, and radiation cataracts.

In one embodiment, the present disclosure relates to a use of a compound or pharmaceutical composition as disclosed above for the manufacture of a medicament for treating or preventing radiation-induced damage to epithelial cells in a subject.

In one embodiment, the radiation-induced damage results in radiation dermatitis.

In one embodiment, the compound or pharmaceutical composition is administered before the subject is exposed to ionizing radiation.

In one embodiment, the compound or pharmaceutical composition is administered after the subject is exposed to ionizing radiation.

In one embodiment, the compound or pharmaceutical composition is administered both before and after the subject is exposed to ionizing radiation.

In one embodiment, the radiation-induced damage results in mucositis.

In one embodiment, the compound or pharmaceutical composition is administered to a mucosal surface in the subject.

In one embodiment, the present disclosure relates to a use of a compound or pharmaceutical composition as disclosed above for the manufacture of a medicament for reducing the likelihood that a subject will develop head and neck cancer.

In one embodiment, the subject is a habitual use of betel quid.

In one embodiment, the composition is a toothpaste, a tooth gel, a tooth powder, a mouth rinse, a chewing gum, or a lozenge.

In one embodiment, the present disclosure relates to a use of a compound or pharmaceutical composition as disclosed above for the manufacture of a medicament for treating or preventing cancer in a subject, the use further comprises a cancer chemotherapeutic agent or ionizing radiation, wherein the compound or composition and the cancer chemotherapeutic agent, or compound or composition and the ionizing radiation, are administered in combined effective amounts to treat or prevent the cancer.

In one embodiment, the chemotherapeutic agent is selected from an alkylating agent, a nitrosourea, an antimetabolite, an antitumor antibiotic, a plant (vinca) alkaloid, and a steroid hormone.

In one embodiment, the alkylating agent is selected from nitrogen mustards, nitrosoureas, ethylenimine derivatives, alkyl sulfonates, and triazenes, including, but not limited to, mechlorethamine, cyclophosphamide, melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

In one embodiment, the ionizing radiation is administered via external beam radiation therapy or brachytherapy.

In one embodiment, the administration of the compound or pharmaceutical composition reduces the amount of the chemotherapeutic agent or the ionizing radiation required to treat or prevent the cancer.

In one embodiment, the present disclosure relates to a use of a compound or pharmaceutical composition as disclosed above for the manufacture of a medicament for reducing the likelihood that a subject will develop oral cancer or lung cancer.

In one embodiment, the compound or pharmaceutical composition is administered by a route selected from intramuscular, intravenous, subcutaneous, topical, and oral.

Representative compounds of the present disclosure include compounds listed in Table 1.

TABLE 1

| Compound no. | Structure |
| --- | --- |
| 100 | 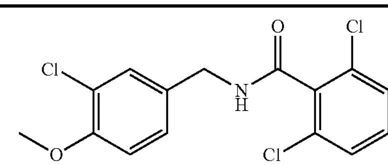 |
| 101 | 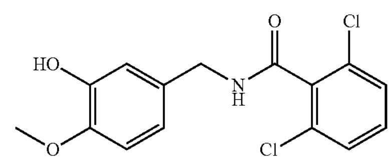 [SMILES: COc1ccc(CNC(=O)c2c(Cl)cccc2Cl)cc1O] |
| 102 | 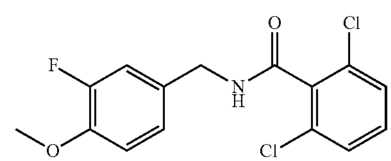 [SMILES: COc1ccc(CNC(=O)c2c(Cl)cccc2Cl)cc1F] |
| 103 | 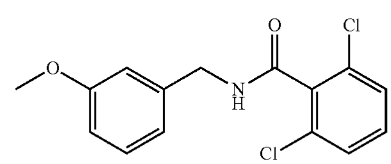 [SMILES: COc1cccc(CNC(=O)c2c(Cl)cccc2Cl)c1] |
| 104 | 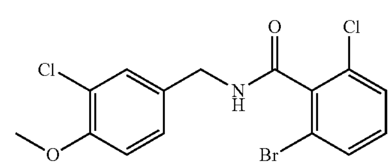 [SMILES: COc1ccc(CNC(=O)c2c(Cl)cccc2Br)cc1Cl] |
| 105 | 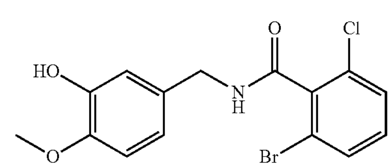 [SMILES: COc1ccc(CNC(=O)c2c(Cl)cccc2Br)cc1O] |

TABLE 1-continued
| Compound no. | Structure |
|---|---|
| 106 | 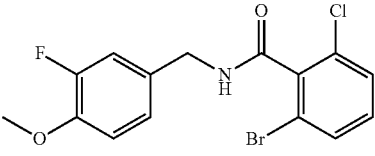 |
| 107 | 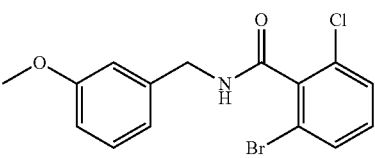 [SMILES: COc1cccc(CNC(=O)c2c(Cl)cccc2Br)c1] |
| 108 | 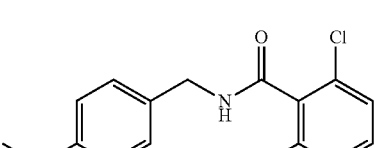 |
| 109 | 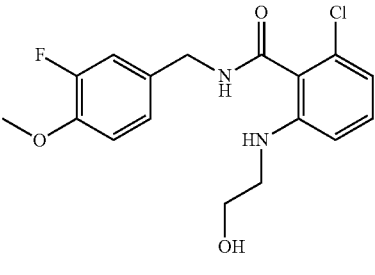 [SMILES: COc1ccc(CNC(=O)c2c(Cl)cccc2NCCO)cc1F] |
| 110 | 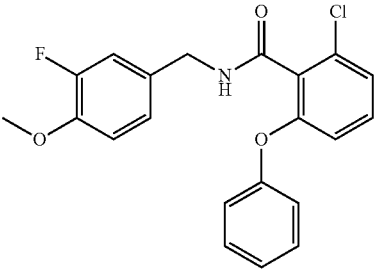 |
| 111 | 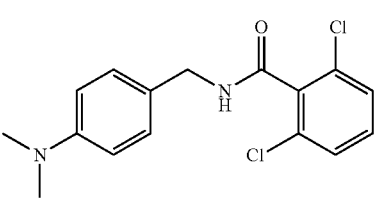 [SMILES: CN(C)c1ccc(CNC(=O)c2c(Cl)cccc2Cl)cc1] |
| 112 | 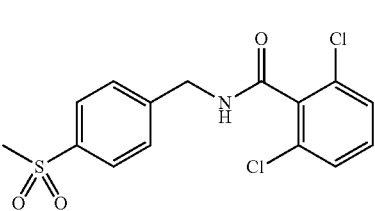 [SMILES: CS(=O)(=O)c1ccc(CNC(=O)c2c(Cl)cccc2Cl)cc1] |
| 113 | 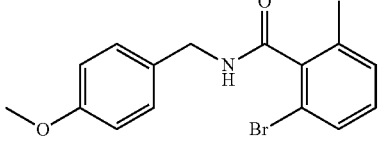 |
| 114 | 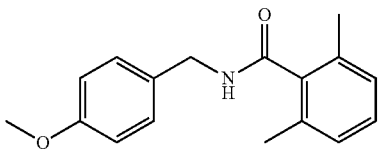 [SMILES: COc1ccc(CNC(=O)c2c(C)cccc2C)cc1] |
| 115 | 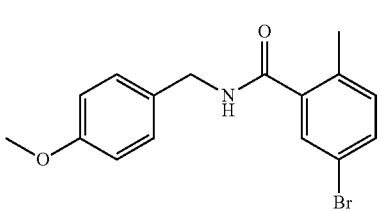 [SMILES: COc1ccc(CNC(=O)c2cc(Br)ccc2C)cc1] |
| 116 | 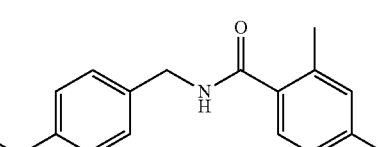 |
| 117 | 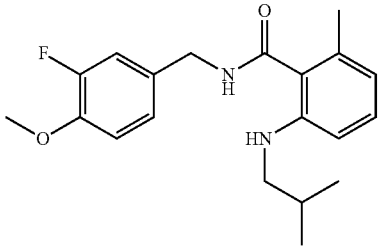 [SMILES: COc1ccc(CNC(=O)c2c(C)cccc2NCC(C)C)cc1F] |
| 118 | 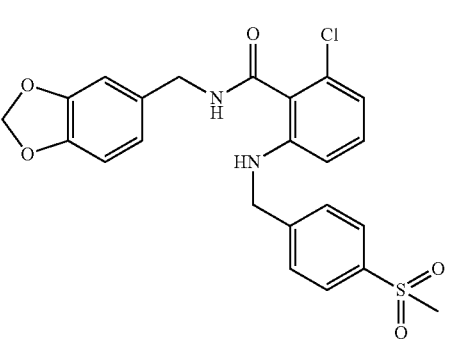 [SMILES: CS(=O)(=O)c1ccc(CNc2cccc(Cl)c2C(=O)NCc2ccc3c(c2)OCO3)cc1] |
| 119 | 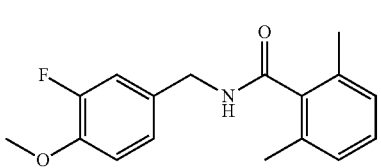 [SMILES: COc1ccc(CNC(=O)c2c(C)cccc2C)cc1F] |

TABLE 1-continued

| Compound no. | Structure |
|---|---|
| 120 | 3-fluoro-4-methoxybenzyl 2,6-bis(2-hydroxyethylamino)benzamide |
| 121 | N-(3-fluoro-4-methoxybenzyl)-2-chlorobenzamide |
| 122 | N-(3-fluoro-4-methoxybenzyl)-2-chloro-6-(isopentyloxy)benzamide |
| 123 | N-(3-fluoro-4-methoxybenzyl)-5-bromo-2-methylbenzamide |
| 124 | N-(3-fluoro-4-methoxybenzyl)-4-bromo-2-methylbenzamide |
| 125 | N-(3-fluoro-4-methoxybenzyl)-2-bromo-6-methylbenzamide |
| 126 | methyl 4-((2-bromo-6-chlorobenzamido)methyl)benzoate |
| 127 | 4-((2-bromo-6-chlorobenzamido)methyl)benzoic acid |
| 128 | 2-bromo-6-chloro-N-(4-nitrobenzyl)benzamide |
| 129 | 2-chloro-N-(3-fluoro-4-methoxybenzyl)-6-((3-methylbenzyl)amino)benzamide |
| 130 | 2-chloro-N-(3-fluoro-4-methoxybenzyl)-6-((4-chlorobenzyl)amino)benzamide |
| 131 | 2-chloro-N-(3-fluoro-4-methoxybenzyl)-6-(m-tolyloxy)benzamide |
| 132 | 2-chloro-N-(3-fluoro-4-methoxybenzyl)-6-(p-tolyloxy)benzamide |

TABLE 1-continued
| Compound no. | Structure |
|---|---|
| 133 | 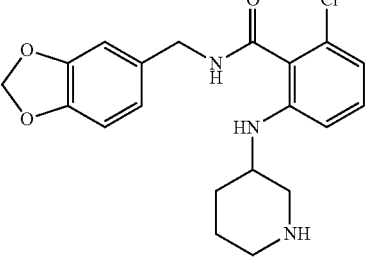 |
| 134 | 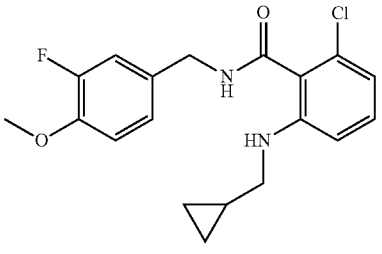 |
| 135 | 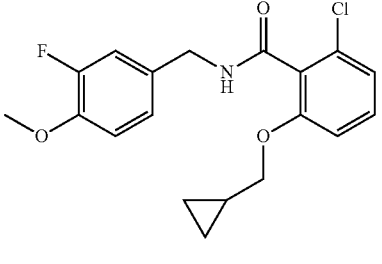 [SMILES: COc1ccc(CNC(=O)c2c(Cl)cccc2OCC2CC2)cc1F] |
| 136 | 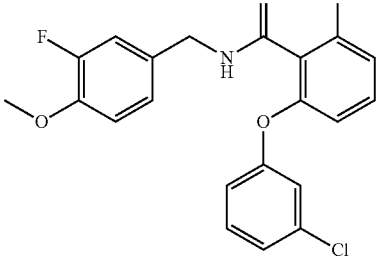 |
| 137 | 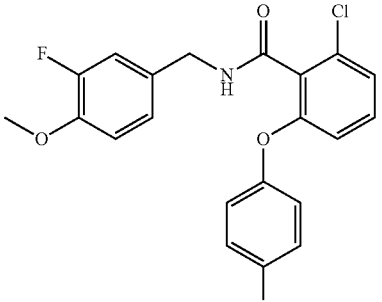 |
| 138 | 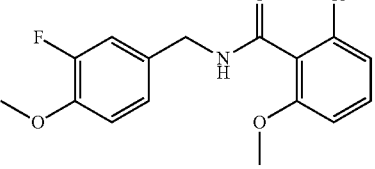 |
| 139 | 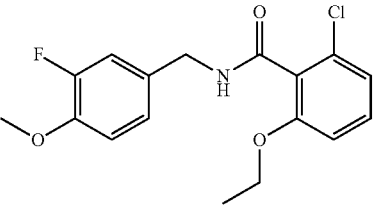 [SMILES: CCOc1cccc(Cl)c1C(=O)NCc1ccc(OC)c(F)c1] |
| 140 | 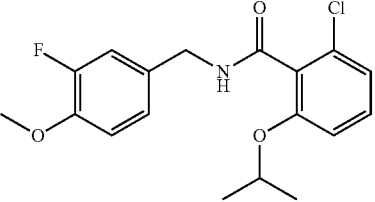 [SMILES: COc1ccc(CNC(=O)c2c(Cl)cccc2OC(C)C)cc1F] |
| 141 | 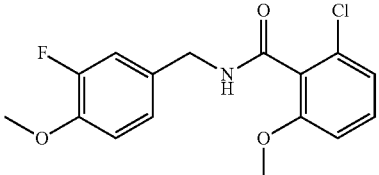 |
| 142 | 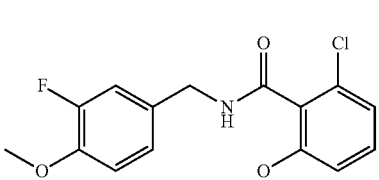 |
| 143 | 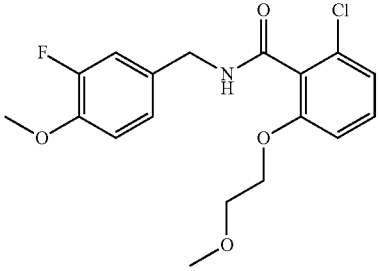 [SMILES: COCCOc1cccc(Cl)c1C(=O)NCc1ccc(OC)c(F)c1] |

TABLE 1-continued

| Compound no. | Structure |
|---|---|
| 144 | (structure) |
| 145 | (structure) |
| 146 | (structure) |
| 147 | (structure) |
| 148 | (structure) |
| 149 | (structure) |
| 150 | (structure) |
| 151 | (structure) |
| 152 | (structure) |
| 153 | (structure) |
| 154 | (structure) |
| 155 | (structure) |
| 156 | (structure) |

TABLE 1-continued

| Compound no. | Structure |
|---|---|
| 157 | (structure) |
| 158 | (structure) |
| 159 | (structure) |
| 160 | (structure) |
| 161 | (structure) |
| 162 | (structure) |
| 163 | (structure) |
| 164 | (structure) |
| 165 | (structure) |
| 166 | (structure) |
| 167 | (structure) |
| 168 | (structure) |

TABLE 1-continued

| Compound no. | Structure |
|---|---|
| 169 | 3-fluoro-4-methoxybenzyl N-substituted 4-chloro-2-(cyclopropylmethoxy)pyridine-3-carboxamide N-oxide |
| 170 | 3-fluoro-4-methoxybenzyl N-substituted 2-chloro-4-(cyclopropylmethoxy)pyridine-3-carboxamide |
| 171 | 3-methoxy-4-fluorobenzyl N-substituted 2,4-dichloropyridine-3-carboxamide |
| 172 | 3-methoxy-4-fluorobenzyl N-substituted 4-chloro-2-(cyclopropylmethoxy)pyridine-3-carboxamide |
| 173 | 4-fluoro-3-methoxy-5-fluorobenzyl N-substituted 2,4-dichloropyridine-3-carboxamide |
| 174 | 2,3-difluoro-4-methoxybenzyl N-substituted 2,4-dichloropyridine-3-carboxamide |
| 175 | 3-fluoro-4-trifluoromethoxybenzyl N-substituted 2,4-dichloropyridine-3-carboxamide |
| 176 | 2,5-difluoro-4-methoxybenzyl N-substituted 2,4-dichloropyridine-3-carboxamide |
| 177 | 3-fluoro-4-isopropoxybenzyl N-substituted 2,4-dichloropyridine-3-carboxamide |
| 178 | 3-fluoro-4-methoxybenzyl N-substituted 4-chloro-2-((1-methylcyclopropyl)methoxy)pyridine-3-carboxamide |
| 179 | 2,3-difluoro-4-methoxybenzyl N-substituted 4-chloro-2-(cyclopropylmethoxy)pyridine-3-carboxamide |
| 180 | 3,4-difluorobenzyl N-substituted 4-chloro-2-(cyclopropylmethoxy)pyridine-3-carboxamide |
| 181 | 3-fluoro-4-methoxybenzyl N-substituted 4-chloro-2-((cyclopropylmethyl)amino)pyridine-3-carboxamide |

TABLE 1-continued
| Compound no. | Structure |
|---|---|
| 182 | 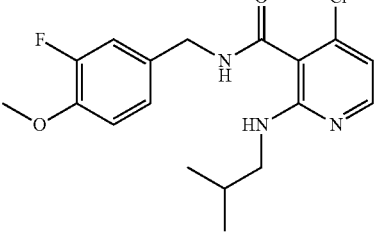 |
| 183 | 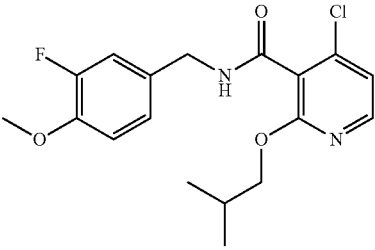 [SMILES: COc1ccc(CNC(=O)c2c(Cl)ccnc2OCC(C)C)cc1F] |
| 184 | 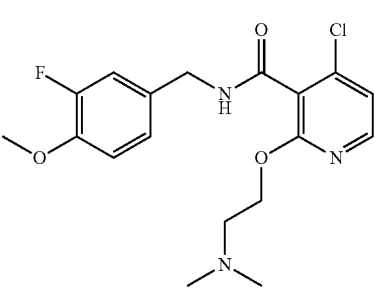 [SMILES: COc1ccc(CNC(=O)c2c(Cl)ccnc2OCCN(C)C)cc1F] |
| 185 | 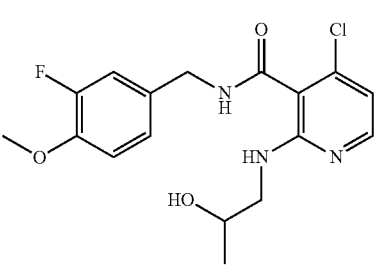 [SMILES: COc1ccc(CNC(=O)c2c(Cl)ccnc2NCC(C)O)cc1F] |
| 186 | 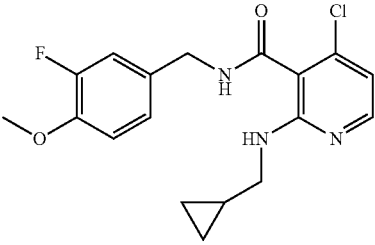 [SMILES: COc1ccc(CNC(=O)c2c(Cl)ccnc2NCC2CC2)cc1F] |
| 187 | 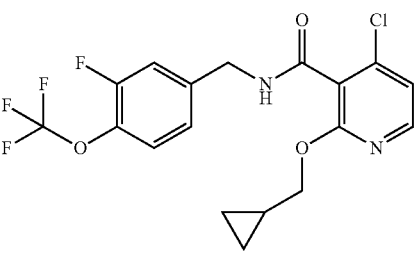 |
| 188 | 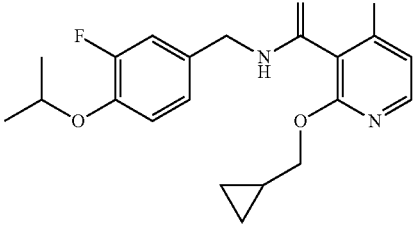 |
| 189 | 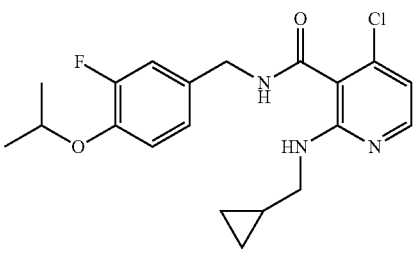 [SMILES: CC(C)Oc1ccc(CNC(=O)c2c(Cl)ccnc2NCC2CC2)cc1F] |
| 190 | 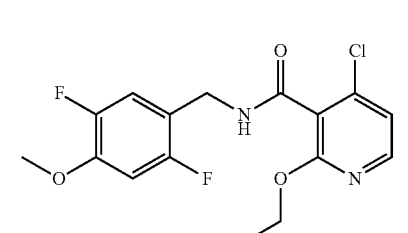 |
| 191 | 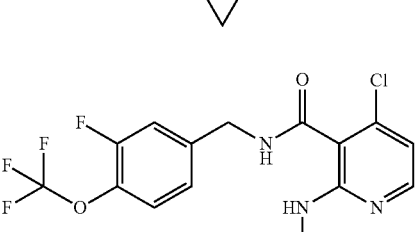 |
| 192 | 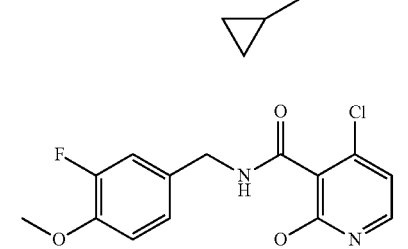 |
| 193 | 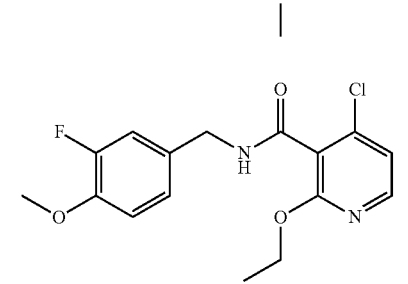 |

TABLE 1-continued

| Compound no. | Structure |
|---|---|
| 194 | 4-chloro-N-(3-fluoro-4-methoxybenzyl)-2-propoxynicotinamide |
| 195 | 4-chloro-N-(3-fluoro-4-methoxybenzyl)-2-isopropoxynicotinamide |
| 196 | 4-chloro-2-cyclopropoxy-N-(3-fluoro-4-methoxybenzyl)nicotinamide |
| 197 | 4-chloro-2-cyclobutoxy-N-(3-fluoro-4-methoxybenzyl)nicotinamide |
| 198 | 4-chloro-2-(cyclobutylmethoxy)-N-(3-fluoro-4-methoxybenzyl)nicotinamide |
| 199 | 4-chloro-2-(cyclopentyloxy)-N-(3-fluoro-4-methoxybenzyl)nicotinamide |
| 200 | 4-chloro-2-(cyclopentylmethoxy)-N-(3-fluoro-4-methoxybenzyl)nicotinamide |
| 201 | 4-chloro-N-(3-fluoro-4-methoxybenzyl)-2-(pentan-3-yloxy)nicotinamide |
| 202 | 2-(sec-butoxy)-4-chloro-N-(3-fluoro-4-methoxybenzyl)nicotinamide |
| 203 | 4-chloro-N-(3-fluoro-4-methoxybenzyl)-2-(neopentyloxy)nicotinamide |
| 204 | 4-chloro-N-(3-fluoro-4-methoxybenzyl)-2-(pyrrolidin-2-ylmethoxy)nicotinamide |
| 205 | 4-chloro-N-(3-fluoro-4-methoxybenzyl)-2-(pyrrolidin-3-ylmethoxy)nicotinamide |

TABLE 1-continued

| Compound no. | Structure |
|---|---|
| 206 | 3-fluoro-4-methoxybenzyl 4-chloro-2-phenoxynicotinamide |
| 207 | 3-fluoro-4-methoxybenzyl 4-chloro-2-(4-chlorophenoxy)nicotinamide |
| 208 | 3-fluoro-4-methoxybenzyl 4-chloro-2-(methylamino)nicotinamide |
| 209 | 3-fluoro-4-methoxybenzyl 4-chloro-2-(ethylamino)nicotinamide |
| 210 | 3-fluoro-4-methoxybenzyl 4-chloro-2-(propylamino)nicotinamide |
| 211 | 3-fluoro-4-methoxybenzyl 4-chloro-2-(isopropylamino)nicotinamide |
| 212 | 3-fluoro-4-methoxybenzyl 4-chloro-2-(sec-butylamino)nicotinamide |
| 213 | 3-fluoro-4-methoxybenzyl 4-chloro-2-(methylthio)nicotinamide |
| 214 | 3-fluoro-4-methoxybenzyl 4-chloro-2-(ethylthio)nicotinamide |
| 215 | 3-fluoro-4-methoxybenzyl 4-chloro-2-(propylthio)nicotinamide |
| 216 | 3-fluoro-4-methoxybenzyl 4-chloro-2-(isopropylthio)nicotinamide |
| 217 | 3-fluoro-4-methoxybenzyl 4-chloro-2-(sec-butylthio)nicotinamide |

TABLE 1-continued

| Compound no. | Structure |
|---|---|
| 218 | 4-chloro-N-(3-fluoro-4-methoxybenzyl)-2-(isobutylthio)nicotinamide |
| 219 | 4-chloro-N-(3-fluoro-4-methoxybenzyl)-2-(methylsulfonyl)nicotinamide |
| 220 | 4-chloro-2-(ethylsulfonyl)-N-(3-fluoro-4-methoxybenzyl)nicotinamide |
| 221 | 4-chloro-N-(3-fluoro-4-methoxybenzyl)-2-(propylsulfonyl)nicotinamide |
| 222 | 4-chloro-N-(3-fluoro-4-methoxybenzyl)-2-(isopropylsulfonyl)nicotinamide |
| 223 | 2-(sec-butylsulfonyl)-4-chloro-N-(3-fluoro-4-methoxybenzyl)nicotinamide |
| 224 | 4-chloro-N-(3-fluoro-4-methoxybenzyl)-2-(isobutylsulfonyl)nicotinamide |
| 225 | 2-(cyclopropylmethoxy)-N-(3-fluoro-4-methoxybenzyl)-4-(trifluoromethyl)nicotinamide |
| 226 | N-(3-fluoro-4-methoxybenzyl)-2-isobutoxy-4-(trifluoromethyl)nicotinamide |
| 227 | N-(3-fluoro-4-methoxybenzyl)-2-isopropoxy-4-(trifluoromethyl)nicotinamide |
| 228 | 2-(pentan-3-yloxy)-N-(3-fluoro-4-methoxybenzyl)-4-(trifluoromethyl)nicotinamide |
| 229 | 2-(cyclobutylmethoxy)-N-(3-fluoro-4-methoxybenzyl)-4-(trifluoromethyl)nicotinamide |

TABLE 1-continued

| Compound no. | Structure |
|---|---|
| 230 | 3-fluoro-4-methoxybenzyl N-{[4-(trifluoromethyl)-2-(cyclopentylmethoxy)pyridin-3-yl]carboxamide} |
| 231 | 3-fluoro-4-methoxybenzyl N-{[4-methyl-2-(cyclopropylmethoxy)pyridin-3-yl]carboxamide} |
| 232 | 3-fluoro-4-methoxybenzyl N-{[4-methyl-2-isobutoxypyridin-3-yl]carboxamide} |
| 233 | 3-fluoro-4-methoxybenzyl N-{[4-methyl-2-isopropoxypyridin-3-yl]carboxamide} |
| 234 | 3-fluoro-4-methoxybenzyl N-{[4-methyl-2-(pentan-3-yloxy)pyridin-3-yl]carboxamide} |
| 235 | 3-fluoro-4-methoxybenzyl N-{[4-methyl-2-(cyclobutylmethoxy)pyridin-3-yl]carboxamide} |
| 236 | 3-fluoro-4-methoxybenzyl N-{[4-methyl-2-(cyclopentylmethoxy)pyridin-3-yl]carboxamide} |
| 237 | 3-fluoro-4-methoxybenzyl N-{[4-methyl-2-(pyrrolidin-3-ylmethoxy)pyridin-3-yl]carboxamide} |
| 238 | 3-fluoro-4-methoxybenzyl N-{[4-methyl-2-cyclobutoxypyridin-3-yl]carboxamide} |
| 239 | 3-fluoro-4-methoxybenzyl N-{[5-chloro-3-(cyclopropylmethoxy)pyridine carboxamide} |
| 240 | 3-fluoro-4-methoxybenzyl N-{[5-chloro-3-isobutoxypyridine carboxamide} |
| 241 | 3-fluoro-4-methoxybenzyl N-{[4-chloro-2-(cyclobutylmethoxy)pyridin-3-yl]carboxamide} |

TABLE 1-continued

| Compound no. | Structure |
|---|---|
| 242 | 3-fluoro-4-methoxybenzyl, cyclopentylmethoxy variant |
| 243 | 3,5-difluoro-4-methoxybenzyl, cyclopropylmethoxy variant |
| 244 | chroman-6-ylmethyl, cyclopropylmethoxy variant |
| 245 | 2,3-dihydrobenzofuran-5-ylmethyl, cyclopropylmethoxy variant |
| 246 | (5-fluoro-6-methoxypyridin-3-yl)methyl, cyclopropylmethoxy variant |
| 247 | N-methyl-3-fluoro-4-methoxybenzyl, cyclopropylmethoxy variant |
| 248 | 3-fluoro-4-hydroxybenzyl, cyclopropylmethoxy variant |
| 249 | 1-(3-fluoro-4-methoxyphenyl)ethyl, cyclopropylmethoxy variant |
| 250 | 3-fluoro-4-methoxybenzyl, isopentyl variant |
| 251 | 3-fluoro-4-methoxybenzyl, 4-methoxy, cyclopropylmethoxy variant |
| 252 | 3-fluoro-5-methoxybenzyl (alt), isobutoxy variant |
| 253 | 3-fluoro-4-(methylsulfonyl)benzyl, cyclopropylmethoxy variant |

TABLE 1-continued

| Compound no. | Structure |
|---|---|
| 254 | 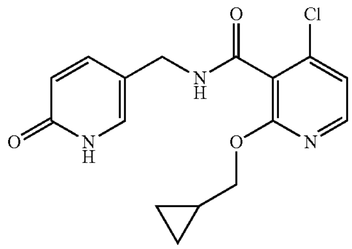 [SMILES: O=C(NCc1ccc(=O)[nH]c1)c1c(Cl)ccnc1OCC1CC1] |
| 255 | 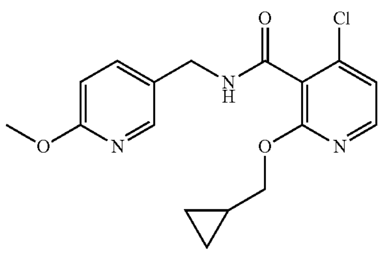 [SMILES: COc1ccc(CNC(=O)c2c(Cl)ccnc2OCC2CC2)cn1] |
| 256 | 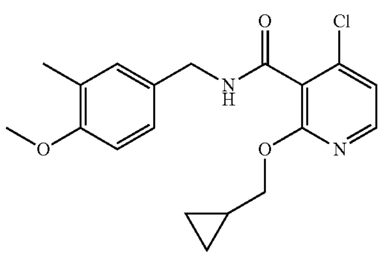 |
| 257 | 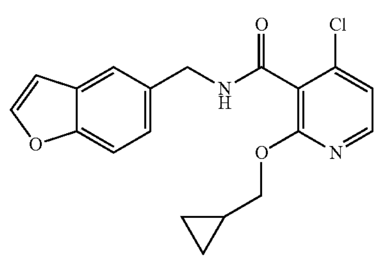 [SMILES: O=C(NCc1ccc2occc2c1)c1c(Cl)ccnc1OCC1CC1] |
| 258 | 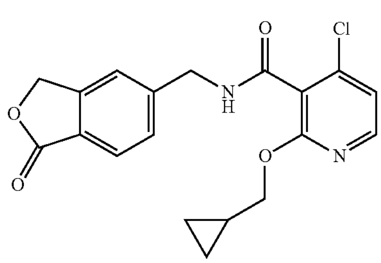 [SMILES: O=C1OCc2cc(CNC(=O)c3c(Cl)ccnc3OCC3CC3)ccc21] |
| 259 | 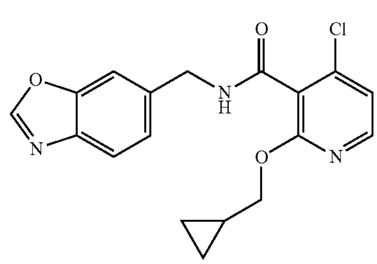 [SMILES: O=C(NCc1ccc2ncsc2c1)c1c(Cl)ccnc1OCC1CC1] |
| 260 | |
| 261 | |
| 262 | |
| 263 | |
| 264 | |
| 265 | |

TABLE 1-continued

| Compound no. | Structure |
|---|---|
| 266 | (structure) |
| 267 | (structure) |
| 268 | (structure) |
| 269 | (structure) |
| 270 | (structure) |
| 271 | (structure) |
| 272 | (structure) |
| 273 | (structure) |
| 274 | (structure) |
| 275 | (structure) |
| 276 | (structure) |
| 277 | (structure) |

The compounds of the disclosure can function as modulators of mitochondrial aldehyde dehydrogenase-2 (ALDH2) activity; and pharmaceutical compositions comprising the compounds. Agonists of ALDH2 are useful for treating or preventing a variety of disorders, including, e.g., conditions involving ischemic stress, chronic free-radical associated diseases, acute free-radical associated diseases, insensitivity to nitroglycerin (e.g., in angina and heart failure), hypertension, diabetes, osteoporosis, Fanconi anemia, Alzheimer disease, and Parkinson's disease. Agonists of ALDH2 are also useful for reducing the level in a subject of a compound such as ethanol, methanol, ethylene glycol monomethyl ether, polyvinyl chloride, xenogenic aldehydes, and biogenic aldehydes. Agonists of ALDH2 are also useful for reducing the level in a subject of a compound that, when ingested, absorbed, or inhaled, gives rise to an aldehyde substrate for ALDH2. Antagonists of ALDH2 are useful for treating or preventing disorders such as cancer, where the ALDH2 antagonist is used as an adjuvant to a standard cancer therapy. Antagonists of ALDH2 are also useful for treating or preventing alcoholism. Antagonists of ALDH2 are also useful for treating or preventing narcotic addiction. The present disclosure provides therapeutic methods involving administering a subject compound, or a subject pharmaceutical composition. The present disclosure further provides assays for identifying agonists of ALDH2.

In some embodiments, subjects to be treated are humans. In some embodiments, a human to be treated according to a subject method is one that has two "wild-type" ALDH2 alleles, e.g., the ALDH2 encoded by the two wild-type ALDH2 alleles has a glutamic acid at position 487. In other embodiments, a human to be treated according to a subject method is one that has one or two "ALDH2*2" alleles, e.g., the ALDH2 encoded by one or both ALDH2 alleles comprises a lysine as amino acid position 487. Sec US 2011/0105602 for details of the amino acid sequence. The E487K polymorphism is a semidominant polymorphism, and results in an ALDH2 tetramer that has significantly lower enzymatic activity than "wild-type" ALDH2. Thus, subjects who are heterozygous or homozygous for the ALDH2*2 allele have much lower in vivo ALDH2 activity levels than subjects who are homozygous for the "wild-type" ALDH2 allele. Subjects who are heterozygous or homozygous for the ALDH2*2 allele are expected to benefit from treatment with a compound of the present disclosure, because the level of ALDH2 activity in such subjects is particularly low, and any increase of ALDH2 activity levels would be expected to provide a therapeutic effect. Any increase in ALDH2 activity would be beneficial in treating conditions such as ischemic disorders, in increasing the responsiveness of such subjects to nitroglycerin, etc.

The use of ALDH2 variants, such as an E487K ALDH2 variant, in screening methods to identify ALDH2 activators (agonists) is also provided. Because the E487K ALDH2 variant has lower enzymatic activity than the "wild-type" ALDH2, the readout for agonist activity of a test compound is more sensitive.

In some embodiments, a compound that modulates ALDH2 activity modulates a dehydrogenase activity of ALDH2, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, a compound that modulates ALDH2 activity modulates an esterase activity of ALDH2. In other embodiments, a compound that modulates ALDH2 activity modulates a reductase activity of ALDH2. For example, ALDH2 can convert nitroglycerin to nitric oxide (NO) via its reductase activity.

In some embodiments, a compound that modulates ALDH2 activity modulates a dehydrogenase activity of ALDH2, e.g., in oxidizing an aldehyde (e.g., a xenogenic aldehyde, a biogenic aldehyde, or an aldehyde produced from a compound that is ingested, inhaled, or absorbed) to the corresponding acid. A variety of compounds can give rise to aldehyde substrates for ALDH2. Non-limiting examples of compounds that can give rise to aldehyde substrates for ALDH2 include ethanol; a variety of insecticides; industrial toxins such as vinyl chlorides (e.g., polyvinyl chloride); and pyruvate. For example, a compound is ingested, absorbed (e.g., through the skin), or inhaled, by a mammal and is subsequently converted in the mammal into an aldehyde substrate for ALDH2.

Biogenic aldehydes include aldehydes that are produced by a mammal, e.g., are produced metabolically by a mammal. Non-limiting examples of biogenic aldehydes include .omega.-6 polyunsaturated fatty acids, such as malondialdehyde (MDA); hexanal; acrolein; glyoxal; crotonaldehyde; trans-2-nonenal; 4-oxo-2-nonenal; and 4-hydroxy-2-nonenal (HNE) (sec e.g., Ellis, Pharmacology & Therapeutics (2007) 115:13, Picklo and Montine (2007) J Alzheimers Dis. 12:185); 3-aminopropanal (3-AP), a product of polyamine oxidase; and aldehyde products of tyrosine, serine and threonine (see Wood et al, Brain Res (2006)1095; 190).

Xenogenic aldehydes include aldehydes ingested, absorbed, or inhaled by a mammal from source outside the mammal. Xenogenic aldehydes include, e.g., formaldehyde and glutaraldehyde (e.g., McGregor et al., Crit. Rev Toxicol (2006) 36:821 and Pandey et al Hum Exp. Toxicol. (2000) 19:360); chloroacetaldehyde (see e.g., Richardson et al., Mutat. Research (2007) 636:178); and reactive aldehydes present in cigarette smoke (see Smith et al., Inhal. Toxicol. (2006) 18:667).

Non-limiting examples of compounds that are substrates for mitochondrial ALDH2 include 3,4-dihydroxypheylacetaldehyde (DOPAL); formaldehyde; acetaldehyde; propionaldehyde; n-butyraldehyde; capronaldehyde; heptaldehyde; pentaldehyde; octylaldehyde; decylaldehyde; retinaldehyde; 3-hydroxybenzaldehyde; 2,5-dihydroxybenzaldehyde; phenylacetaldehyde; 3-phenylpropionaldehyde (see, e.g., Want et al. (2002) Drug Metabolism and Disposition 30:69); cinnamoyl and hydrocinnamoyl aldehydes and their derivative aldehydes (e.g. p-nitrocinnamaldehyde, p-(dimethylamino)cinnamaldehyde, hydrocinnamaldehyde, .alpha.-phenylpropionaldehyde); benzaldehyde and its derivative aldehydes (e.g. 2,4-dinitro-benzaldehyde, o-nitro-benzaldehyde, p-nitro-benzaldehyde, p-methyl-benzaldehyde, m-methyl-benzaldehyde, p-methoxy-benzaldehyde, p-(dimethylamino)-benzaldehyde, m-methoxy-benzaldehyde, m-hydroxy-benzaldehyde, 3,4-dimethoxy-benzaldehyde, o-methoxy-benzaldehyde); naphthaldehyde and its derivative aldehydes (e.g. 5-bromo-1-naphthaldehyde, 5-nitro-1-naphthaldehyde, 6-[O—(CH2)5-COOH]-2-naphthaldehyde, 6-(dimethylamino)-2-naphthaldehyde); coumarin-4-carboxaldehyde and its derivative aldehydes (e.g. 7-acetoxy-coumarin-4-carboxaldehyde, 7-(dimethylamino)-coumarin-4-carboxaldehyde, 7-methoxy-coumarin-4-carboxaldehyde, 6,7-dimethoxy-coumarin-4-carboxaldehyde); quinoline, quinolinonecarboxaldehyde, and their derivative aldehydes (e.g. quinoline-3-carboxaldehyde, 7-(dimethylamino)-2-quinolinone-4-carboxaldehyde, quinoline-4-carboxaldehyde, 6-methoxy-2-quinolinone-4-carboxaldehyde); phenanthrene-9-carboxaldehyde; indole-3-aldehyde, indole-3-acetaldehyde; 5-methoxyindole-3-carboxaldehyde; 3-pyridinecarboxaldehyde; fluorene-2-carboxaldehyde (see, e.g., Klyosov, (1996) Biochemstry 35:4457); 4-hydroxynonenal; malondialdehyde; 3,4-dihydroxyphenylacetaldehyde; and 5-hydroxylindole-3-acetaldehyde. See, also, e.g., Williams et al. (2005) Anal. Chem. 77:3383; Marchitti et al. (2007) Pharmacol. Rev. 59:125; and Hoffman and Maser (2007) Drug Metab. Rev. 39:87.

The present disclosure provides ALDH2 agonists (also referred to as "activators"); and pharmaceutical compositions comprising ALDH2 agonists. Agonists of ALDH2 are useful for treating or preventing a variety of disorders, including, e.g., conditions involving ischemic stress, chronic free-radical associated diseases, acute free-radical associated diseases, insensitivity to nitroglycerin (e.g., in angina and heart failure), hypertension, diabetes, and osteoporosis. Agonists are also useful in the detoxification of alcohol abuse, methanol poisoning, ethylene glycol monomethyl ether poisoning, and poisoning due to other xenogenic or biogenic aldehyde compounds.

Whether a compound is an ALDH2 agonist can be readily ascertained. Assays for dehydrogenase activity of ALDH2 are known in the art, and any known assay can be used. Examples of dehydrogenase assays are found in various publications, including, e.g., Sheikh et al. ((1997) J. Biol. Chem. 272:18817-18822); Vallari and Pictruszko (1984) J. Biol. Chem. 259:4922; and Farres et al. ((1994) J. Biol. Chem. 269:13854-13860).

As an example of an assay for dehydrogenase activity, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes NAD+ (e.g., 0.8 mM NAD+, or higher, e.g., 1 mM, 2 mM, or 5 mM NAD+) and an aldehyde substrate such as 14 µM propionaldehyde. Reduction of NAD+ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide (NAD+) to its reduced form, NADH, at 340 nm, as described in US 2005/0171043; and WO 2005/057213. In an exemplary assay, the reaction is carried out at 25° C. in 0.1 NaPPi buffer, pH 9.5, 2.4 mM NAD+ and 10 mM acetaldehyde as the substrate. Enzymatic activity is measured by a reductive reaction of NAD+ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH2 enzymatic activity.

Whether a compound increases an esterase activity of ALDH2 can be determined using any known assay for esterase activity. For example, esterase activity of ALDH2 can be determined by monitoring the rate of p-nitrophenol formation at 400 nm in 25 mM N,N-Bis(2-hydroxyethyl)-2-amino ethanesulfonic acid (BES) (pH 7.5) with 800 µM p-nitrophenyl acetate as the substrate at room temperature in the absence or presence of added NAD+. A pH-dependent molar extinction coefficient of 16 mM-1 cm-1 at 400 nm for nitrophenol can be used. See, e.g., Larson et al. (2007) J. Biol. Chem. 282:12940). Esterase activity of ALDH2 can be determined by measuring the rate of p-nitrophenol formation at 400 nm in 50 mM Pipes (pH 7.4) with 1 mM p-nitrophenylacetate as the substrate. A molar extinction coefficient of 18.3×103 M-1 cm-1 at 400 nm for p-nitrophenolate can be used for calculating its rate of formation. See, e.g., Ho et al. (2005) Biochemistry 44:8022).

Whether a compound increases a reductase activity of ALDH2 can be determined using any known assay for reductase activity. A reductase activity of ALDH2 can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 ml in ethanol for subsequent TLC separation and scintillation counting. See, e.g., Zhang and Stamler (2002) Proc. Natl. Acad. Sci. USA 99:8306.

The present disclosure provides ALDH2 antagonists (also referred to as "ALDH2 inhibitors"), and pharmaceutical compositions comprising ALDH2 antagonists. In some embodiments, ALDH2 antagonists are useful for treating or preventing alcohol addiction. In other embodiments, ALDH2 antagonists increase the sensitivity of a cancerous cell to a cancer chemotherapeutic agent. Thus, in some embodiments, ALDH2 antagonists are useful as adjuvants to standard cancer therapies, in the treatment or prevention of cancer.

Whether a compound is an ALDH2 antagonist can be readily ascertained. Assays for ALDH2 are known in the art, and any known assay can be used. Examples of assays are found in various publications, including, e.g., Sheikh et al. ((1997) J. Biol. Chem. 272:18817-18822) and Farres et al. ((1994) J. Biol. Chem. 269:13854-13860). For example, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes NAD+(e.g., 0.8 mM NAD+, or higher, e.g., 1 mM, 2 mM, or 5 mM NAD+) and a substrate such as 14 µM propionaldehyde. Reduction of NAD+ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide (NAD+) to its reduced form, NADH, at 340 nm, as described in US 2005/0171043; and WO 2005/057213. In an exemplary assay, the reaction is carried out at 25° C. in 0.1 NaPPi buffer, pH 9.5, 2.4 mM NAD+ and 10 mM acetaldehyde as the substrate. Enzymatic activity is measured by a reductive reaction of NAD+ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH2 enzymatic activity.

The term "compounds of the present disclosure" refers to a compound according to formula I, II, III, IV, IIa, IIIa, IVa, IIb, IIIb, IVb, IIc, IIIc, IVc, V, Va, Vb, Vc, or Vc.

With respect to the chemical compounds useful in the present disclosure, the following terms can be applicable:

The term "substituted," as used herein, means that any one or more hydrogens on the designated atom is replaced with a selection from the indicated group, provided that the designated atoms normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When any variable (e.g., R1) occurs more than one time in any constituent or formula for a compound, its definition at each occurrence is independent of its definition at every other occurrence. Thus, for example, if a group is shown to be substituted with 0-2 R1 moieties, then the group may optionally be substituted with up to two R1 moieties and R1 at each occurrence is selected independently from the definition of R1. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present disclosure that contain nitrogens can be converted to N-oxides by treatment with an oxidizing agent (e.g., 3-chloroperoxybenzoic acid (m-CPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or N+—O—). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-6 alkyl, C1-6 alkenyl, C1-6 alkynyl, C3-14 carbocycle, or 3-14-membered heterocycle) derivatives.

When an atom or chemical moiety is followed by a subscripted numeric range (e.g., $C_{1-6}$), the present disclosure is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, C1-6 alkyl is intended to include C1, C2, C3, C4, C5, and C6 alkyl groups. Examples of alkyl include, but are not limited to, methyl, ethyl, n-propyl, i-propyl, n-butyl, s-butyl, t-butyl, n-pentyl, s-pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., C1-C6 for straight chain, C3-C6 for branched chain), and in another embodiment, a straight chain or branched chain alkyl has four or fewer carbon atoms. Likewise, cycloalkyls have from three to eight carbon atoms in their ring structure, and in another embodiment, cycloalkyls have five or six carbons in the ring structure.

"Substituted alkyls" refers to alkyl moieties having substituents replacing one or more hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonyl amino, carbamoyl and ureido), amidino, imino, sulthydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., C2-C6 for straight chain, C3-C6 for branched chain). Likewise, cycloalkenyl groups may have from three to eight carbon atoms in their ring structure, and in one embodiment, cycloalkenyl groups have five or six carbons in the ring structure. The term "C2-C6" includes alkenyl groups containing two to six carbon atoms. The term "C3-C6" includes alkenyl groups containing three to six carbon atoms.

"Substituted alkenyls" refers to alkenyl moieties having substituents replacing one or more hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., C2-C6 for straight chain, C3-C6 for branched chain). The term "C2-C6" includes alkynyl groups containing two to six carbon atoms. The term "C3-C6" includes alkynyl groups containing three to six carbon atoms.

"Substituted alkynyls" refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl aryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

The term "haloalkyl" refers to both branched and straight-chain saturated aliphatic hydrocarbon groups having the specified number of carbon atoms, substituted with 1 or more halogen (for example —CvFw wherein v=1 to 3 and w=1 to (2v+1)). Examples of haloalkyl include, but are not limited to, trifluoromethyl, trichloromethyl, pentafluoroethyl, and pentachloroethyl.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a C3-14 carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctalienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when a covalent bond or one or more carbon atoms link two non-adjacent carbon atoms in a ring. In one embodiment, bridge rings are one or two carbon atoms. It is noted that a bridge always converts a monocyclic ring into a bicyclic ring. When a ring is bridged, the substituents recited for the ring may also be present on the bridge. Fused (e.g., naphthyl and tetrahydronaphthyl) and Spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and S(O)p, where p=1 or 2). When a nitrogen atom is included in the ring it is either N or NH, depending on whether or not it is attached to a double bond in the ring (i.e., a hydrogen is present if needed to maintain the trivalency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when a covalent bond or one or more atoms (i.e., C, O, N, or S) link two non-adjacent carbon or nitrogen atoms in a ring. Bridges include, but are not limited to, one carbon atom, two carbon atoms, one nitrogen atom, two nitrogen atoms, and a carbon-nitrogen group. It is noted that a bridge always converts a monocyclic ring into a bicyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and S(O)p, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "hydroxy" or "hydroxyl" includes groups with an —OH or —O—.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H2O, such combination being able to form one or more hydrate.

"Tautomers" refers to compounds whose structures differ markedly in arrangement of atoms, but which exist in easy and rapid equilibrium. It is to be understood that the compounds of the present disclosure may be depicted as different tautomers. It should also be understood that when compounds have tautomeric forms, all tautomeric forms are intended to be within the scope of the present disclosure, and the naming of the compounds does not exclude any tautomer form.

Some compounds of the present disclosure can exist in a tautomeric form which are also intended to be encompassed within the scope of the present disclosure.

The compounds, salts and prodrugs of the present disclosure can exist in several tautomeric forms, including the enol and imine form, and the keto and enamine form and geometric isomers and mixtures thereof. All such tautomeric forms are included within the scope of the present disclosure. Tautomers exist as mixtures of a tautomeric set in solution. In solid form, usually one tautomer predominates. Even though one tautomer may be described, the present disclosure includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including topical, oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this present disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the present disclosure are capable of further forming salts. All of these forms are also contemplated within the scope of the present disclosure.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present disclosure can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present disclosure.

The compounds of the present disclosure can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present disclosure can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present disclosure can be delivered in prodrug form. Thus, the present disclosure is intended to cover prodrugs of the presently claimed compounds, methods of delivering the same and compositions containing the same. "Prodrugs" are intended to include any covalently bonded carriers that release an active parent drug of the present disclosure in vivo when such prodrug is administered to a subject. Prodrugs the present disclosure are prepared by modifying functional groups present in the compound in such a way that the modifications are cleaved, either in routine manipulation or in vivo, to the parent compound. Prodrugs include compounds of the present disclosure wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl)N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p. 1-92, Elesevier, New York-Oxford (1985).

As used herein, the term "mitochondrial aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an NAD+-dependent reaction. For example, ALDH2 oxidizes aldehydes derived from the breakdown of compounds, e.g., toxic compounds that are ingested, that are absorbed, that are inhaled, or that are produced during normal metabolism.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms; (2) relieving the disease state, i.e., causing temporary or permanent regression of the disease state or its clinical symptoms; or (3) reducing or lessening the symptoms of the disease state.

"Preventing" includes any effect in, e.g., causing the clinical symptoms of the disease state not to develop in a subject that may be exposed to or predisposed to the disease state, but does not yet experience or display symptoms of the disease state.

The term "ALDH2" encompasses ALDH2 from various species. Amino acid sequences of ALDH2 from various species are publicly available. For example, a human ALDH2 amino acid sequence is found under GenBank Accession Nos. AAII02967 and NP_000681; a mouse ALDH2 amino acid sequence is found under GenBank Accession No. NP_033786; and a rat ALDH2 amino acid sequence is found under GenBank Accession No. NP_115792. The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of human ALDH2 or at a position corresponding to amino acid 487 of human ALDH2. This mutation is referred to as the "E487K mutation"; the "E487K variant"; or as the "Glu504Lys polymorphism". See, e.g., Larson et al. (2005) J. Biol. Chem. 280:30550; and Li et al. (2006) J. Clin. Invest. 116:506. An ALDH2 variant retains at least about 1% of the enzymatic activity of a corresponding wild-type ALDH2 enzyme.

In the specification, the singular forms also include the plural, unless the context clearly dictates otherwise. Unless defined otherwise, all technical and scientific terms used herein have the same meaning as commonly understood by one of ordinary skill in the art to which this present disclosure belongs. In the case of conflict, the present specification will control.

All percentages and ratios used herein, unless otherwise indicated, are by weight.

2. Synthesis of Compounds

General Procedure:

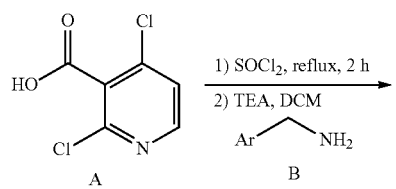

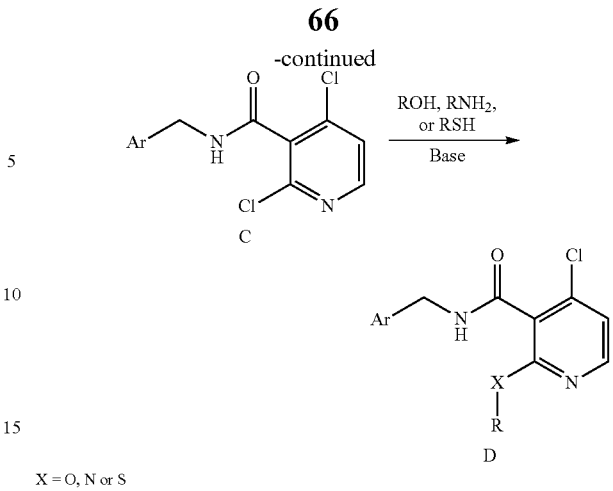

X = O, N or S

Carboxylic acid A is reacted with SOCl$_2$ to form the corresponding acyl chloride then reacting with benzyl amine B to form the corresponding intermediate amide C, followed by nucleophilic aromatic substitution by addition of alcohols, amines, or thiols with base to provide the product D

3. Methods of Treatment and Prevention

The present disclosure provides various treatment and prevention methods, generally involving administering to a subject an effective amount of a compound of the present disclosure. Diseases and conditions associated with ALDH2 include ischemic stress, chronic free-radical associated diseases, acute free-radical associated diseases, insensitivity to nitroglycerin (e.g., in angina and heart failure), hypertension, diabetes, osteoporosis, cancer, alcoholism, alcohol intolerance, alcohol addiction, an alcohol abuse disorder, alcohol intoxication, alcohol dependence, alcohol poisoning, symptoms of alcohol consumption, and narcotic addition.

Methods of Treating or Preventing Alcohol-Related Diseases or Conditions

The present disclosure provides a method of treating or preventing alcohol intolerance, alcohol addiction, an alcohol abuse disorder, alcohol intoxication, alcohol dependence, alcohol poisoning, or symptoms of alcohol consumption, the method comprising administering to a subject an effective amount of a compound or pharmaceutical composition of the present disclosure. A compound of the present disclosure can be administered to a subject on a regular basis to treat or prevent alcohol addiction. For example, in some embodiments, a compound of the present disclosure is administered to a subject twice daily, daily, every other day, twice weekly, once per week, or twice per month. A compound of the present disclosure can be administered in the form of a transdermal "patch" to treat or prevent alcohol addiction. "Treating alcohol addiction," as used herein, includes achieving one or more of the following: a reduction in the amount of alcohol consumed; a reduction in the frequency at which alcohol is consumed; a reduction in the craving for alcohol; and a reduction in one or more of the symptoms of excessive alcohol consumption. "Alcohol," as used herein in the context of alcohol addiction, refers to ethanol, e.g., beverages containing 2%, 3%, 4% 5%, or more, by volume, ethanol, e.g., wine, beer, vodka, whiskey, and the like.

Subjects suitable for treatment with a compound of the present disclosure include subjects who have alcohol addiction, including subjects who are considered to be alcoholics (e.g., subject having a primary, chronic disease characterized by one or more of: impaired control over drinking alcohol, preoccupation with the drug alcohol, use of alcohol despite adverse consequences, and distortions in thinking following consumption of alcohol); subjects suffering from withdrawal symptoms following cessation of alcohol consumption; subjects experiencing alcohol dependence (e.g., alcohol abuse combined with tolerance, withdrawal, and an uncontrollable urge to drink alcohol); and the like.

Alcohol intoxication (also known as drunkenness or inebriation) refers to the physiological state of a subject induced by the consumption of alcohol, when it builds up in the bloodstream faster than it can be metabolized by the liver. Common effects are euphoria and lowered social inhibitions. Common symptoms of alcohol intoxication include slurred speech, euphoria, impaired balance, loss of muscle coordination (ataxia), flushed face, dehydration, vomiting, reddened eyes, reduced inhibitions, and erratic behavior. Sufficiently high levels of blood-borne alcohol will cause coma and death from the depressive effects of alcohol upon the central nervous system.

Compounds of the present disclosure can also treat or prevent alcohol poisoning, such as acute alcohol poisoning, which refers to a high concentration of alcohol in the blood, e.g., high enough to induce coma or respiratory depression. Acute alcohol poisoning is considered a medical emergency. Symptoms of acute alcohol poisoning include e.g., severe confusion, unpredictable behavior, stupor, sudden lapses into and out of unconsciousness or semi-consciousness (with later alcoholic amnesia), vomiting while unconscious or semi-conscious seizures, respiratory depression (fewer than eight breaths a minute), and pale, bluish, cold and clammy skin due to insufficient oxygen.

In one embodiment, treatment or prevention of alcohol intoxication or alcohol poisoning comprises of administering a compound of the present disclosure to a subject in an emergency room. In another embodiment, compounds of the present disclosure can be used to treat or prevent symptoms of alcohol intoxication, alcohol poisoning, or alcohol consumption in subject. Some examples of symptoms of alcohol intoxication and alcohol poisoning are listed above. Symptoms as a result of alcohol consumption include e.g., hangover. Hangover (also known as veisalgia) is the experience of various unpleasant physiological effects following the consumption of alcohol. Characteristics of a hangover include e.g., headache, nausea, sensitivity to light and noise, lethargy, dysphoria, diarrhea and thirst, typically after the intoxicating effect of the alcohol begins to wear off. While a hangover can be experienced at any time, generally a hangover is experienced the morning after a night of heavy drinking. In addition to the physical symptoms, a hangover may also induce psychological symptoms including heightened feelings of depression and anxiety.

Hangover symptoms may persist for several days after alcohol was last consumed. Some aspects of a hangover are viewed as symptoms of acute ethanol withdrawal. An alcohol hangover is associated with a variety of symptoms that may include dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor functions (including tremor), trouble sleeping, severe hunger, halitosis, and lack of depth perception. Some subjects may also be repulsed by the thought, taste or smell of alcohol during a hangover. The symptoms vary significantly from subject to subject.

The present disclosure provides methods of providing maintenance for a subject with an ALDH2 deficiency gene to remove acetaldehyde in the subject, comprising administering to the subject an effective amount of a compound of the present disclosure before, after, or contemporaneous with alcohol consumption. In some embodiments, the subject has two "wild-type" ALDH2 alleles, e.g., the ALDH2 encoded by the two wild-type ALDH2 alleles has a glutamic acid at position 487. In other embodiments, the subject has one or two "ALDH2*2" alleles, e.g., the ALDH2 encoded by one or both ALDH2 alleles comprises a lysine as amino acid position 487. The E487K polymorphism is a semidominant polymorphism, and results in an ALDH2 tetramer that has significantly lower enzymatic activity than "wild-type" ALDH2. Thus, subjects who are heterozygous or homozygous for the ALDH2*2 allele have much lower in vivo ALDH2 activity levels than subjects who are homozygous for the "wild-type" ALDH2 allele. The subjects with such an ALDH2 deficiency gene, e.g., heterozygous or homozygous for the ALDH2*2 allele, are expected to benefit from treatment with a compound of the present disclosure, because the level of ALDH2 activity in such subject is particularly low, and any increase of ALDH2 activity levels would be expected to provide a therapeutic effect.

Approximately 40% of the East Asian population carries the semidominant ALDH2*2 allele. Such subjects can be characterized by a response to ethanol consumption that includes one or more of facial flushing, nausea, and tachycardia. Subjects who are heterozygous or homozygous for the ALDH2*2 allele are suitable for treatment with a subject method involving administration of a compound of the present disclosure.

The compounds of the present disclosure can be used to sequester aldehydes in a subject exposed to alcohol or aldehyde. The compounds of the present disclosure can be used as aldehyde sequestering agents. The sequestering agent can be administered before, after, or contemporaneous with alcohol consumption and/or aldehyde exposure. A compound of the present disclosure can sequester the aldehyde in a subject by e.g., binding or reacting with the aldehyde to form a stable and non-toxic form, and thus preventing the aldehyde from causing damaging effects in the subject.

In some embodiments, the compounds of the present disclosure can be administered in combination with an opioid receptor antagonist to treat or prevent alcohol-related diseases and/or conditions. The opioid antagonist include e.g., naltrexone, which is a competitive antagonists that binds to the opioid receptors with higher affinity than agonists but do not activate the receptors.

This effectively blocks the receptor, preventing the body from responding to opiates and endorphins. Naltrexone is also a partial inverse agonist, which can be used for the treatment or prevention of opioid addiction.

Methods of Detoxification

The present disclosure provides methods of reducing the levels of a toxic compound in a subject, the methods generally involving administering to a subject an effective amount of a compound of the present disclosure. The present disclosure provides methods of treating or preventing a disorder associated with or resulting from a toxic level of a compound (e.g., a xenogenic aldehyde; a biogenic aldehyde; or a compound that, when ingested, absorbed, or inhaled, gives rise to an aldehyde substrate for ALDH2), the methods generally involving administering to subject an effective amount of a compound of the present disclosure, where the level of the compound in the subject is reduced to a non-toxic level.

Toxic compounds whose levels can be reduced in a subject using a subject method include, but are not limited to, ethanol, methanol, ethylene glycol monomethyl ether, xenogenic aldehydes, biogenic aldehydes, and an aldehyde produced by in vivo metabolism of a compound that is ingested, absorbed, or inhaled. A compound of the present disclosure is administered in an amount that is effective, when administered in one or more doses, to reduce a toxic level of a compound such as ethanol, methanol, ethylene glycol monomethyl ether, xenogenic aldehydes, biogenic aldehydes, or an aldehyde produced by in vivo metabolism of a compound that is ingested, absorbed, or inhaled. In some embodiments, the aldehyde is acetaldehyde.

The present disclosure provides methods of reducing aldehyde toxicity, the methods generally involving administering an effective amount of a compound of the present disclosure. In some embodiments, an effective amount of a compound of the present disclosure is an amount that is effective to reduce one or more symptoms of aldehyde toxicity. For example, in some embodiments, an effective amount of a compound of the present disclosure is an amount that is effective to reduce one or more symptoms of excess ethanol consumption, where such symptoms include, e.g., headache, dehydration, fatigue, nausea, vomiting, diarrhea, weakness, anxiety, irritability, photophobia, phonophobia, etc.

Subjects suitable for treatment with a compound of the present disclosure include subjects who have toxic levels of an aldehyde, e.g., via ingestion of a toxic compound, via inhalation of a toxic compound, via ingestion or inhalation of toxic levels of a compound, or via production of the aldehyde during normal metabolism. Such subjects include, but are not limited to, subjects who have ingested or inhaled ethanol, methanol, ethylene glycol monomethyl ether, or other xenogenic or biogenic aldehyde compounds. For example, such subjects include subjects who have ingested or inhaled pesticides, fungicides, or other such compounds; subjects who have consumed excessive levels of ethanol; and the like.

Methods of Treating or Preventing Conditions Involving Ischemic Stress

The present disclosure provides methods for treating or preventing conditions involving ischemic stress, including prophylactic methods, in a subject, the methods generally involving administering to a subject an effective amount of a compound of the present disclosure. Conditions involving ischemic stress include ischemic conditions, ischemic events, conditions that can give rise to ischemia, and conditions that result from an ischemic event. Conditions involving ischemic stress that are amenable to treatment with a subject method include ischemia that result from any condition or event, including, but not limited to, myocardial infarct (e.g., acute myocardial infarction), cardiac surgery, brain trauma, cerebrovascular disease, stroke, spinal cord injury, subarachnoid hemorrhage, major surgery in which ischemia to variety of organs occur, organ transplantation, peripheral artery disease, limb ischemia (e.g., resulting from Type 1 or Type 2 diabetes), and the like.

In some embodiments, the agent is administered before a predicted or anticipated ischemic event, e.g., from about 1 hour to about 1 week before the ischemic event. Pretreatment with an active agent is desirable under certain circumstances, for example, when a subject has already experienced a stroke, when a subject is about to undergo cardiac surgery, etc. For example, a patient who has already experienced a stroke will have an increased probability of experiencing a second stroke. Subjects who are susceptible to transient ischemic attacks also have an increased risk of a stroke. Subjects who suffer a subarachnoid hemorrhage may experience further ischemic events induced by vasospasms that constrict the blood vessels. Subjects who experience trauma to organs such as the brain are also susceptible to an ischemic event. Subjects undergoing surgery over an extended period of time are also susceptible to an ischemic event. The above situations exemplify circumstances when a subject would benefit from pretreatment with a compound of the present disclosure.

In some embodiments, a compound of the present disclosure is administered after an ischemic event. For example, a compound of the present disclosure is effective in reducing the adverse effects of an ischemic event such as cardiac ischemia, reperfusion injury, cerebrovascular disease, acute myocardial infarction, subarachnoid hemorrhage, and trauma. In some embodiments, a compound of the present disclosure is administered within 1 minute to within 15 hours. In some embodiments, an increased concentration of a compound of the present disclosure is maintained in the plasma for at least several hours to several days following the ischemic event.

For example, in some embodiments, a compound of the present disclosure is administered to a subject who has suffered an acute myocardial infarction (AMI) within 1 minute to within 15 hours.

Methods of Treating or Preventing Chronic and Acute Free-Radical Associated Diseases The present disclosure provides methods for treating or preventing acute and chronic free-radical associated diseases in a subject, the methods generally involving administering to a subject an effective amount of a compound of the present disclosure.

Acute free radical-associated disorders that are amenable to treatment with a subject method include seizures (Patel et al. (2001) Journal of Neurochemistry 79:1065-1069); skin damage resulting from UV exposure, and photodamage of skin (e.g., "sunburn") (Aldini et al. (2007) Chem Res Toxicol. 20(3):416-23); acute thermal skin burn injury (Pintaudi et al. (2000) Free Radic Res. 33(2): 139-46); and tissue hyperoxia (e.g., hyperoxia-induced chronic lung disease; and bronchopulmonary dysplasia) (Xu et al. (2006) Am J Physiol Lung Cell Mol. Physiol. 291(5):L966-75).

The present disclosure provides methods for treating or preventing sunburn in a subject, the methods generally involving administering to a subject an effective amount of a compound of the present disclosure. In some embodiments, a subject method for treating or preventing sunburn comprises topically applying a formulation comprising a compound of the present disclosure to an area of the skin affected by sunburn.

The present disclosure provides methods for treating or preventing a seizure in a subject, the methods generally involving administering to a subject an effective amount of a compound of the present disclosure. In some embodiments, a compound of the present disclosure is administered after a seizure has occurred, e.g., within from about 1 minute to about 5 minutes following a seizure. In other embodiments, a compound of the present disclosure is administered prophylactically, e.g., a compound of the present disclosure is administered to a subject who has experienced a seizure in the past, to reduce the likelihood that another seizure will occur. In some embodiments, an effective amount of a compound of the present disclosure is an amount that is effective to reduce at least one of the severity of a seizure, the frequency of seizures, and the duration of a seizure.

The present disclosure provides methods for treating or preventing chronic free-radical associated diseases in a subject, the methods generally involving administering to a subject an effective amount of a compound of the present disclosure. Chronic free radical-associated disorders that are amenable to treatment with a subject method include neurodegenerative diseases such as Parkinson's Disease and Alzheimer's Disease (Burke et al. (2003) Neurol. Dis. 2(2): 143; and Ohta and Ohsawa (2006) J. Alzheimer's Disease 9(2): 155); amyotrophic lateral sclerosis (ALS); cancer such as esophageal cancer (Chen et al. (2006) Int J Cancer 2119(12):2827-31); upper aerodigestive tract cancer (Hashibe et al. (2006) Cancer Epidemiol Biomarkers Prev. 15(4):696-703); head and neck squamous cell carcinoma (Hashimoto et al. (2006) Tumour Biol. 27(6):334-8; Yokoyama et al. (2005) Alcohol. 35(3): 175-85); Fanconi anemia (Langevin et al. (2011) Nature. 475(7354): 53; and Garaycoechea et al. (2012) Nature. 489(7417): 571); cardiovascular diseases such as atherosclerosis (Narita et al. (2003) Ultrasound in Medicine and Biology 29(10):1415-1419); and the like. In some embodiments, a chronic free radical-associated disease is treated or prevented by chronic (e.g., daily) treatment with a compound of the present disclosure.

The present disclosure provides a method for treating or preventing Alzheimer's Disease (AD) in a subject suffering from AD, the method generally involving administering to the subject an effective amount of a compound of the present disclosure. In some embodiments, an "effective amount" of a compound of the present disclosure is an amount that is effective to at least slow the decline in cognitive function in the subject.

The present disclosure provides a method for treating or preventing Parkinson's Disease in a subject, the method generally involving administering to the subject an effective amount of a compound of the present disclosure.

Methods of Treating or Preventing Heart Conditions

The present disclosure provides methods of treating or preventing disorders such as angina, heart failure, insensitivity to nitroglycerin in angina and heart failure (Li et al. (2006) J. Clin. Invest. 116:506-511), hypertension (Asselin et al. (2006) Free Radical Biol. and Med. 41:97), and heart disease. The methods generally involve administering to a subject an effective amount of a compound of the present disclosure.

In some embodiments, a compound of the present disclosure is administered to a subject in conjunction with nitroglycerin treatment. A compound of the present disclosure and the nitroglycerin can be administered by the same route of administration (e.g., oral, sublingual, transdermal, translingual, etc.). In the alternative, a compound of the present disclosure and the nitroglycerin can be administered by different routes of administration. For example, in some embodiments, nitroglycerin is administered sublingually, translingually, transdermally, or orally; and a compound of the present disclosure is administered via a different route of administration (e.g., intravenous, intramuscular, etc.). A compound of the present disclosure can be administered before, during, or after administration of the nitroglycerin.

In some embodiments, an effective amount of a compound of the present disclosure is an amount that is effective to treat or prevent hypertension, e.g., to reduce one or more symptoms or indications of hypertension in a subject. For example, in some embodiments, an effective amount of a compound of the present disclosure is an amount that is effective to reduce blood pressure in the subject by at least about 5%, at least about 10%, at least about 15%, at least about 20%, or at least about 25%, or more, or to bring the blood pressure of the subject to within a normal range.

In some embodiments, an effective amount of a compound of the present disclosure is an amount that is effective to treat or prevent heart disease, e.g., to reduce one or more symptoms or indications of heart disease in a subject. Whether a given compound of the present disclosure is effective to treat or prevent heart disease can be determined using standard methods of assessing heart function, e.g., electrocardiogram, angiogram, and the like.

Methods of Reducing Salsolinol Levels

The present disclosure provides methods of reducing salsolinol levels in a subject, the methods generally involving administering to the subject an effective amount of a compound of the present disclosure. Salsolinol (1-methyl-6,7-dihydroxy-1,2,3,4-tetrahydroisoquionoline) is a condensation product of dopamine with acetaldehyde. Acetaldehyde is a metabolic product of ethanol. Plasma salsolinol levels are higher in alcoholic compared to non-alcoholics. Reduction of salsolinol levels is useful in reducing alcohol addiction.

In some embodiments, an effective amount of a compound of the present disclosure is administered to a subject following excessive alcohol (e.g., ethanol) consumption; where the effective amount provides for a reduction in the levels of salsolinol in the subject compared to the salsolinol levels in the subject before treatment with a compound of the present disclosure. In some embodiments, an effective amount of a compound of the present disclosure is administered to a subject at any time (e.g., not necessarily following excessive alcohol consumption). In some of these embodiments, the subject is one who has been diagnosed with alcoholism. Symptoms and diagnosis of alcoholism are described in, e.g., Enoch and Goldman (2002) American Family Physician 65:441.

Methods of Treating or Preventing Cancer

The present disclosure provides methods of treating or preventing cancer in a subject. The methods generally involve administering to a subject an effective amount of a compound of the present disclosure in conjunction with a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

The present disclosure provides methods for increasing the susceptibility of a solid tumor to ischemic damage by decreasing the level and/or activity of ALDH2. The methods generally involve administering to a subject having a solid tumor an effective amount of an agent that reduces a level and/or activity of ALDH2.

In some embodiments, an agent that decreases a level and/or activity of ALDH2 is administered as adjuvant therapy to a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan®), melphalan (L-sarcolysin), carmustine lomustine (CCNU), semustine (methyl-CCNU), streptozocin, chlorozotocin, uracil mustard, chlormethine, ifosfamide, chlorambucil, pipobroman, triethytenemelamine, triethylenethiophosphoramine, busulfan, dacarbazine, and temozolomide.

Antimetabolite as include folic acid analogs, pyrimidine analogs, purine analogs, and adenosine deaminase inhibitors, including, but not limited to, cytarabine (CYTOSAR-U), cytosine arabinoside, fluorouracil (5-EU), floxuridine (FudR), 6-thioguanine, 6-mercaptopurine (6-MP), pentostatin, 5-fluorouracil methotrexate, 10-propargyl-5,8-dideazafolate (PDDF, CB3717), 5,8-dideazatetrahydrofolic acid leucovorin, fludarabine phosphate, pentostatine, and gemeitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, epothilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglulethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL®, TAXOTERE® (a formulation of docetaxel), 10-desacetyl analogs of paclitaxel and 3N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere® docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in international Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/8288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists: (5) interleukin-2; (6) IFN-.alpha.; (7) IFN-.gamma.; (8) colony-stimulating factors: (9) inhibitors of angiogenesis; and (10) antagonists of tumor necrosis factor.

A subject method is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, an "effective amount" of an agent that decreases a level and/or activity of ALDH2 is an amount sufficient to reduce a tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample, e.g., blood; and the like.

Subjects suitable for treatment with a subject agent and/or a subject method, where the agent increases a level and/or activity of ALDH2, include subjects who are scheduled to undergo cardiac surgery or who have undergone cardiac surgery; subjects who have experienced a stroke; subjects who have suffered brain trauma; subjects who have prolonged surgery; and subjects who will be subjected to organ transplantation.

Subjects suitable for treatment with a subject agent and/or a subject method, where the agent decreases a level and/or activity of ALDH2, include subjects having a solid tumor. Solid tumors include, but are not limited to, histiocytic lymphoma, cancers of the brain, genitourinary tract, lymphatic system, stomach, larynx and lung, including lung adenocarcinoma and small cell lung cancer.

Diabetes

The present disclosure provides methods of treating or preventing diabetes, the methods generally involving administering to a subject an effective amount of a compound of the present disclosure. In some embodiments, a subject method of treating or preventing diabetes provides for treatment or prevention of a disorder that is a result of diabetes, e.g., diabetic nephropathy, diabetic neuropathy, and the like.

In some embodiments, a compound of the present disclosure is administered in an amount that is effective to reduce a blood glucose level in a subject when compared to the blood glucose levels in the absence of treatment with the compound of the present disclosure. In some embodiments, an effective amount of a compound of the present disclosure is an amount that is effective to reduce blood glucose levels to a normal range.

In some embodiments, a subject treatment method comprises administering a compound of the present disclosure, and co-administering at least a second therapeutic agent (e.g., insulin) for the treatment or prevention of diabetes. Insulin that is suitable for use herein includes, but is not limited to, regular insulin, semilente, NPH, lente, protamine zinc insulin (PZI), ultralente, insuline glargine, insulin aspart, acylated insulin, monomeric insulin, superactive insulin, hepatoselective insulin, and any other insulin analog or derivative, and mixtures of any of the foregoing. Insulin that is suitable for use herein includes, but is not limited to, the insulin forms disclosed in U.S. Pat. Nos. 4,992,417; 4,992,418; 5,474,978; 5,514,646; 5,504,188; 5,547,929; 5,650,486; 5,693,609; 5,700,662; 5,747,642; 5,922,675; 5,952,297; and 6,034,054; and published PCT applications WO 00/121197; WO 09/010,645; and WO 90/12814. Insulin analogs include, but are not limited to, superactive insulin analogs, monomeric insulins, and hepatospecific insulin analogs.

Osteoporosis

The present disclosure provides methods of treating or preventing osteoporosis, the methods generally involving administering to a subject an effective amount of a compound of the present disclosure. In some embodiments, an "effective amount" of a compound of the present disclosure is an amount effective to increase bone density in the subject. In other embodiments, an "effective amount" of a compound of the present disclosure is an amount that is effective to reduce the rate of bone density loss.

4. Pharmaceutical Compositions

The present disclosure provides pharmaceutical compositions comprising a compound of the present disclosure. The compound of the present disclosure can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public In the subject methods, a subject ALDH2 activity modulator (also referred to below as "active agent") may be administered to the host using any convenient means capable of resulting in the desired reduction in autoimmune disease. Thus, a subject ALDH2 activity modulator can be incorporated into a variety of formulations for therapeutic administration. More particularly, a subject ALDH2 activity modulator can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject active agent may be administered in the form of their pharmaceutically acceptable salts, or a subject active agent may be used alone or in appropriate association, as well as in combination, with other pharmaceutically active compounds. The following methods and excipients are merely exemplary and are in no way limiting.

For oral preparations, a subject active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject active agent can be utilized in aerosol formulation to be administered via inhalation. A subject active agent can be formulated into pressurized acceptable propellants such as dichlorodifluoromethane, propane, nitrogen and the like.

Furthermore, a subject active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for a subject active agent depend on the particular compound employed and the effect to be achieved, and the pharmacodynamics associated with each compound in the host.

A subject active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, a subject ALDH2 activity modulator can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present disclosure. Similarly, unit dosage forms for injection or intravenous administration may comprise the compound(s) in a composition as a solution in sterile water, normal saline or another pharmaceutically acceptable carrier.

In some embodiments, multiple doses of a subject compound are administered. The frequency of administration of a subject compound can vary depending on any of a variety of factors, e.g., severity of the symptoms, etc. For example, in some embodiments, a subject compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, a subject compound is administered continuously.

The duration of administration of a subject compound, e.g., the period of time over which a subject compound is administered, can vary, depending on any of a variety of factors, e.g., patient response, etc. For example, a subject compound can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, a subject compound is administered for the lifetime of the subject.

A subject ALDH2 activity modulator is administered to a subject using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, rectal, nasal, oral, and other enteral and parenteral routes of administration. Routes of administration may be combined, if desired, or adjusted depending upon the agent and/or the desired effect. The compound can be administered in a single dose or in multiple doses.

An active agent can be administered to a host using any available conventional methods and routes suitable for delivery of conventional drugs, including systemic or localized routes. In general, routes of administration contemplated by the present disclosure include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

5. General Assays

Assays used to study the efficacy the compounds of the present disclosure may be carried out using methods known in the art.

Enzymatic Assay

ALDH2 catalyzes the oxidative reaction of substrate acetaldehyde to acetic acid using $NAD^+$ as a cofactor. Enzymatic activity, or catalytic rate, of aldehyde dehydrogenase (ALDH2) can be measured spectrophotometrically at UV wavelength λ340 nm by the accumulation of reduced product NADH derived from $NAD^+$. Absorbance at λ340 nm is quantitatively proportional to the amount of NADH being produced over time (6.22 O.D. unit=1 mmole of NADH, measured in a 1-cm width standard cuvette). This method is well-established in the literature [e.g. D. K. Rex, W. F. Bosron, J. E. Smialek, T. K. Li, *Alcohol Clin Exp Res* 9, 147 (1985)].

Cloning, Expression and Purification of Human ALDH2 Wild Type and ALDH2*2 Recombinant Mutant Enzymes Full-length wild type human ALDH2 cDNA may be purchased from ATCC (No. MGC-1806. GenBank ID: BC002967). The 18-amino acid mitochondria transport signal sequence may be removed by PCR and cloned into the NheI/HindIII sites of a His-tag vector, pTrcHis, using standard molecular cloning techniques. The human ALDH2* cDNA construct containing the Asian E487K mutation can be obtained by site-directed mutagenesis to create the E487K substitution of the wild type ALDH2. Both human clones may be designed to express a recombinant protein with the His-tag at the N-terminus of the protein. For the co-expression experiments of human ALDH2 wild type and ALDH2*2 heterotetramers, a wild type ALDH2 gene and a ALDH2 E487K gene may be inserted separately into the two multiple cloning sites of pETDuet-1 vector. (Novagen, CA, USA). All the vectors may be transformed into BL21 *E. coli* host cells and subjected to 0.5 mM IPTG induction for protein expression at 30° C. Purifications of the recombinant proteins by affinity nickel columns (HisTrap, GE Healthy Science, USA) may be carried out using standard protocols according to manufacturer's instructions (Novagen, USA).

6. Examples

Example 1: Synthesis of Compounds

Preparation of Intermediate 3

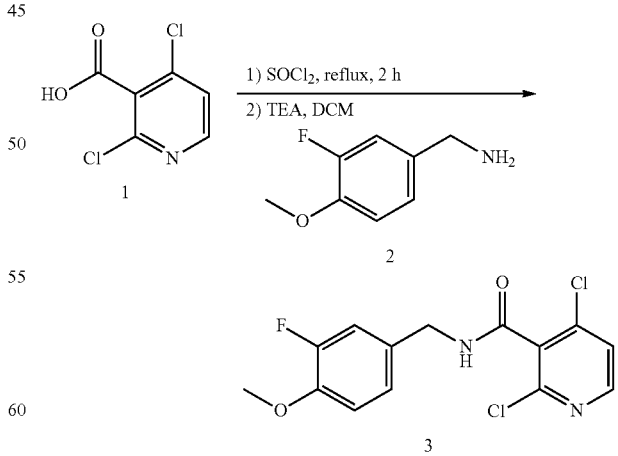

A solution of compound 1 (13.6 g, 70 mmol) in $SOCl_2$ was refluxed for 2 h. Then concentrated and re-dissolved in dichloromethane (20 mL), which was added to another solution of the amine 2 (8.5 g, 55 mmol) and TEA (7.0 g, 70 mmol) in dichloromethane (150 mL) at 0° C. After stirring overnight at room temperature, the reaction mixture was then poured into water and extracted with dichloromethane. The combined organic extracts were washed with brine, water and dried over Na$_2$SO$_4$, filtered and evaporated in vacuum. The resulting yellow solid was purified by flash column chromatography to provide the title compound 3 as a pale white solid (17 g). $^1$H NMR (400 MHz, DMSO-d6): δ 9.26 (t, J=5.6 Hz, 1H), 8.42 (d, J=5.6 Hz, 1H), 7.68 (d, J=5.2 Hz, 1H), 7.20-7.13 (m, 3H), 4.41 (d, J=6.0 Hz, 2H), 3.81 (s, 3H); m/z (ESI) (M+H)$^+$=329.10.

Preparation of Ether Substituted Compounds

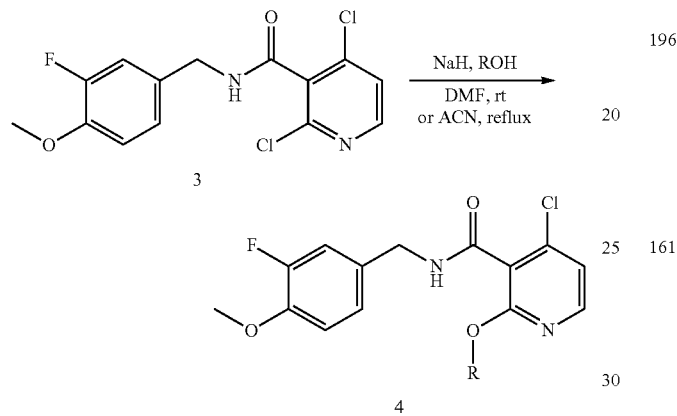

The compound 3 and alcohol were dissolved in DMF, and then 60% NaH was added to the solution. The mixture was stirred over night at room temperature. Then the mixture was diluted with EtOAc, and washed with H$_2$O and brine. The organic phase was separated and dried with Na$_2$SO$_4$, concentrated under reduced pressure and the residue was purified with thin-layer chromatography (Ether:EtOAc=3:2) to afford compound 4.

Below are illustrative examples of compound 4 prepared according to the process described above.

| Compound no. | ROH | Analytical Data |
|---|---|---|
| 192 | —OH | $^1$H NMR (400 MHz, CDCl3): δ 8.29 (d, J = 6.0 Hz, 1H), 7.15 (dd, J1 = 12.0 Hz, J2 = 2.0 Hz, 1H), 7.09 (d, J = 8.0 Hz, 1H), 6.93 (t, J = 8.0 Hz, 1H), 6.83 (d, J = 5.6 Hz, 1H), 6.05-5.95 (m, 1H), 4.60 (d, J = 6.0 Hz, 2H), 3.93 (s, 3H), 3.89 (s, 3H); m/z (ESI) (M + H)+ = 325.10; HPLC tR = 6.03 min. |
| 193 | ethyl-OH | $^1$H NMR (400 MHz, CDCl3): δ 8.25 (d, J = 5.6 Hz, 1H), 7.15 (dd, J1 = 12.0 Hz, J2 = 2.0 Hz, 1H), 7.08 (d, J = 8.0 Hz, 1H), 6.93 (t, J = 8.0 Hz, 1H), 6.79 (d, J = 5.6 Hz, 1H), 6.08-5.98 (m, 1H), 4.60 (d, J = 6.0 Hz, 2H), 4.15 (q, J = 7.2 Hz, 2H), 3.88 (s, 3), 1.46 (t, J = 7.2 Hz, 3H); m/z (ESI+) (M + H)+ = 339.15; HPLC tR = 6.33 min. |
| 194 | propyl-OH | |
| 195 | isopropyl-OH | $^1$H NMR (400 MHz, CDCl3): δ 8.23 (d, J = 5.6 Hz, 1H), 7.16 (dd, J1 = 12.0 Hz, J2 = 2.0 Hz, 1H), 7.08 (d, J = 8.4 Hz, 1H), 6.92 (t, J = 8.4 Hz, 1H), 6.78 (d, J = 5.6 Hz, 1H), 6.05-5.95 (m, 1H), 4.68-4.64 (m, 1H), 4.60 (d, J = 6.0 Hz, 2H), 3.88 (s, 3H), 1.3 (d, J = 6.0 Hz, 6H); m/z (ESI+) (M + H)+ = 353.15; HPLC tR = 6.51 min. |
| 196 | cyclopropyl-OH | $^1$H NMR (400 MHz, CD3OD): δ 8.29 (d, J = 5.6 Hz, 1H), 7.44 (d, J = 5.6 Hz), 7.15-7.02 (m, 3H), 4.46 (s, 2H), 4.04-4.00 (m, 1H), 3.86 (s, 3H), 0.90-0.86 (m, 2H), 0.78-0.74 (m, 2H); m/z (ESI+) (M + H)+ = 351.15; HPLC tR = 6.44 min. |
| 161 | cyclopropylmethyl-OH | $^1$H NMR (400 MHz, DMSO-d6): δ 8.97 (t, J = 6 Hz, 1H), 8.25 (d, J = 6.0 Hz, 1H), 7.21-7.07 (m, 4H), 4.38 (d, J = 5.6 Hz, 2H), 3.97 (d, J = 6.8 Hz, 2H), 3.79 (s, 3H), 1.20-1.16 (m, 1H), 0.55 (Apparent ABq, J = 6.4, 6.0 Hz, 2H), 0.30 (Apparent ABq, J = 5.6, 4.8 Hz, 2H); m/z (ESI+) (M + H)+ = 365.10. |
| 197 | cyclobutyl-OH | $^1$H NMR (400 MHz, CDCl3): δ 8.21 (d, J = 5.6 Hz, 1H), 7.17 (dd, J1 = 12.0 Hz, J2 = 2.4 Hz, 1H), 7.09 (d, J = 8.4 Hz, 1H), 6.92 (t, J = 8.4 Hz, 1H), 6.65 (d, J = 6.0 Hz, 1H), 6.05-6.00 (m, 1H), 4.73-4.70 (m, 1H), 4.61 (d, J = 5.6 Hz, 2H), 3.88 (s, 3H), 2.48-2.44 (m, 2H), 2.24-2.21 (m, 2H), 1.92-1.89 (m, 1H), 1.56-1.53 (m, 1H); m/z (ESI+) (M + H)+ = 365.15; HPLC tR = 6.75 min. |
| 198 | cyclobutylmethyl-OH | $^1$H NMR (400 MHz, CDCl3): δ 8.23 (d, J = 6.0 Hz, 1H), 7.13 (dd, J1 = 11.2 Hz, J2 = 2.0 Hz, 1H), 7.07 (d, J = 8.4 Hz, 1H), 6.90 (t, J = 8.4 Hz, 1H), 6.78 (d, J = 6.0 Hz, 1H), 6.08-6.04 (m, 1H), 4.58 (d, J = 6.4 Hz, 2H), 4.01 (d, J = 6.4 Hz, 2H), 3.87 (s, 3H), 2.78-2.73 (m, 1H), 2.11-2.09 (m, 2H), 1.95-1.78 (m, 4H); m/z (ESI+) (M + H)+ = 379.20; HPLC tR = 7.04 min. |
| 199 | cyclopentyl-OH | $^1$H NMR (400 MHz, CDCl3): δ 8.23 (d, J = 6.0 Hz, 1H), 7.14 (dd, J1 = 12.0 Hz, J2 = 1.6 Hz, 1H), 7.08 (d, J = 7.2 Hz, 1H), 6.92 (t, J = 8.4 Hz, 1H), 6.79 (d, J = 5.6 Hz, 1H), 6.00-5.96 (m, 1H), 4.84-4.82 (m, 1H), 4.58 (d, J = 5.6 Hz, 2H), 3.88 (s, 3H), 1.9-1.60 (m, 8H); m/z (ESI+) (M + H)+ = 379.20; HPLC tR = 6.92 min. |

-continued

| Compound no. | ROH | Analytical Data |
|---|---|---|
| 200 | cyclopentylmethanol | $^1$H NMR (400 MHz, CDCl3): δ 8.23 (d, J = 6.0 Hz, 1H), 7.13 (dd, J1 = 11.2 Hz, J2 = 2.0 Hz, 1H), 7.09 (d, J = 8.0 Hz, 1H), 6.90 (t, J = 8.4 Hz, 1H), 6.78 (d, J = 6.0 Hz, 1H), 6.05-6.04 (m, 1H), 4.59 (d, J = 6.4 Hz, 2H), 3.92 (d, J = 7.2 Hz, 2H), 3.88 (s, 3H, 2.36-2.32 (m, 1H), 1.79-1.72 (m, 2H), 1.62-1.56 (m, 4H), 1.29-1.26 (m, 2H); m/z (ESI+) (M + H)+ = 393.20; HPLC tR = 7.27 min. |
| 201 | pentan-3-ol | $^1$H NMR (400 MHz, CDCl3): δ 8.19 (d, J = 5.6 Hz, 1H), 7.14 (dd, J1 = 12.0 Hz, J2 = 2.0 Hz, 1H), 7.07 (d, J = 8.0 Hz, 1H), 6.91 (t, J = 8.0 Hz, 1H), 6.74 (d, J = 5.6 Hz, 1H), 6.12-6.06 (m, 1H), 4.57 (d, J = 5.4 Hz, 2H), 4.26-4.21 (m, 1H), 3.87 (s, 3H), 1.68 (q, J = 7.6 Hz, 4H), 0.89 (t, J = 7.6 Hz, 6H); m/z (ESI+) (M + H)+ = 381.25; HPLC tR = 7.08 min. |
| 202 | butan-2-ol | $^1$H NMR (400 MHz, CDCl3): δ 8.16 (d, J = 6.0 Hz, 1H), 7.13 (dd, J1 = 11.2 Hz, J2 = 2.0 Hz, 1H), 7.06 (d, J = 8.0 Hz, 1H), 6.90 (t, J = 8.0 Hz, 1H), 6.74 (d, J = 6.4 Hz, 1H), 6.24-6.18 (m, 1H), 4.56 (d, J = 5.6 Hz, 2H), 4.40-4.36 (m, 1H), 3.86 (s, 3H), 1.771.60 (m, 2H), 1.30 (d, J = 6.0 Hz, 3H), 0.91 (t, J = 7.2 Hz, 3H); m/z (ESI+) (M + H)+ = 367.15; HPLC tR = 6.76 min. |
| 183 | isobutanol | $^1$H NMR (400 MHz, DMSO-d6): δ 8.98 (t, J = 6.0 Hz, 1H), 8.25 (d, J = 6.0 Hz, 1H), 7.17-7.06 (m, 4H), 4.36 (d, J = 5.6 Hz, 2H), 3.86 (d, J = 6.8 Hz, 2H), 3.80 (s, 3H), 1.97-1.91 (m, 1H), 0.87 (d, J = 7.2 Hz, 6H); m/z (ESI+) (M + H)+ = 365.10. |
| 178 | cyclopropylmethanol | |
| 203 | neopentyl alcohol | |
| 204 | (pyrrolidin-2-yl)methanol | $^1$H NMR (400 MHz, CDCl3): δ 8.20 (d, J = 5.6 Hz, 1H), 7.15 (d, J = 12 Hz, 1H), 7.08 (d, J = 8.8 Hz, 1H), 6.90 (t, J = 8.4 Hz, 1H), 6.77 (d, J = 2.4 Hz, 1H), 4.66-4.62 (m, 1H), 4.45-4.40 (m, 1H), 4.08-4.06 (m, 1H), 3.98-3.94 (m, 1H), 3.87 (s, 3H), 3.56-3.54 (m, 1H), 2.95-2.85 (m, 2H), 1.96-1.91 (m, 1H), 1.85-1.75 (m, 2H), 1.56-1.52 (m, 1H); m/z (ESI+) (M + H)+ = 394.25; HPLC tR = 5.24 min. |
| 205 | (pyrrolidin-3-yl)methanol | $^1$H NMR (400 MHz, CD3OD): δ 8.30 (d, J = 6.0 Hz, 1H), 7.18-7.05 (m, 4H), 4.65 (s, 1H), 4.48 (s, 2H), 4.27-4.16 (m, 2H), 3.86 (s, 3H), 3.43-3.38 (m, 1H), 3.29-3.23 (m, 2H), 3.10-3.07 (m, 1H), 2.85-2.81 (m, 1H), 2.18-2.13 (m, 1H), 1.86-1.80 (m, 1H); m/z (ESI) (M + H)+ = 394.20; HPLC tR = 8.45 min. |
| 206 | phenol | $^1$H NMR (400 MHz, CDCl3): δ 8.18 (d, J = 5.6 Hz, 1H), 7.45 (t, J = 8.0 Hz, 2H), 7.30 (t, J = 8.0 Hz, 1H), 7.16-7.09 (m, 4H), 6.89 (t, J = 8.4 Hz, 1H), 6.61 (d, J = 4.8 Hz, 1H), 6.20-6.17 (m, 1H), 4.62 (d, J = 5.6 Hz, 2H), 3.87 (s, 3H); m/z (ESI+) (M + H)+ = 87.20; HPLC tR = 6.90 min. |
| 207 | 4-chlorophenol | $^1$H NMR (400 MHz, CDCl3): δ 8.21 (d, J = 5.2 Hz, 1H), 7.41 (d, J = 8.8 Hz, 2H), 7.14-7.04 (m, 4H), 6.89 (t, J = 8.4 Hz, 1H), 6.61 (d, J = 5.2 Hz, 1H), 6.23-6.21 (m, 1H), 4.61 (d, J = 6.0 Hz, 2H), 3.87 (s, 3H); m/z (ESI+) (M + H)+ = 421.20; HPLC tR = 7.25 min. |

Preparation of Amine Substituted Compounds

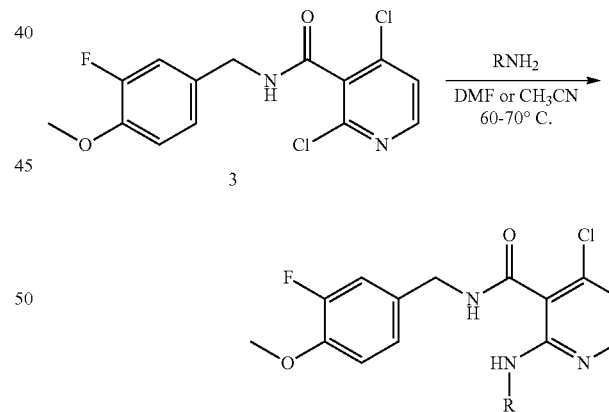

The compound 3 and Amine were dissolved in DMF or acetonitrile, and then K$_2$CO$_3$ was added to the solution, the result suspension was stirred overnight at room temperature. TLC or HPLC monitor the reaction was completed, the mixture was diluted with EtOAc and H$_2$O, separated, dried, concentrated. The crude solid was crystallization with EtOAc/ether to get the desire product 5.

Below are illustrative examples of compound 5 prepared according to the process described above.

| Compound no. | RNH₂ | Structure | Analytical Data |
|---|---|---|---|
| 208 | —NH₂ | (structure) | 1H NMR (400 MHz, CDCl3): δ 8.04 (d, J = 5.6 Hz, 1H), 7.54-7.50 (m, 1H), 7.19-7.17 (m, 1H), 7.10-7.07 (m, 2H), 6.92 (t, J = 8.0 Hz, 1H), 6.56 (d, J = 6.0 Hz, 1H), 4.52 (d, J = 5.6 Hz, 2H), 3.88 (s, 3H), 2.95 (s, 3H); m/z (ESI+) (M + H)+ = 324.10; HPLC tR = 5.20 minT |
| 209 | (ethylamine) | (structure) | |
| 210 | (propylamine) | (structure) | |
| 211 | (isopropylamine) | (structure) | ¹H NMR (400 MHz, CDCl3): δ 7.96 (d, J = 6.4 Hz, 1H), 7.12-7.09 (m, 2H), 6.92 (t, J = 8.4 Hz, 1H), 6.50 (d, J = 6.0 Hz, 1H), 6.15-6.13 (m, 1H), 4.54 (d, J = 5.6 Hz, 2H), 3.88 (s, 3H), 3.00 (s, 6H); m/z (ESI+) (M + H)+ = 338.05; HPLC tR = 5.34 min |
| 212 | (sec-butylamine) | (structure) | |
| 182 | (isobutylamine) | (structure) | |

| Compound no. | RNH₂ | Structure | Analytical Data |
|---|---|---|---|
| 186 |  | 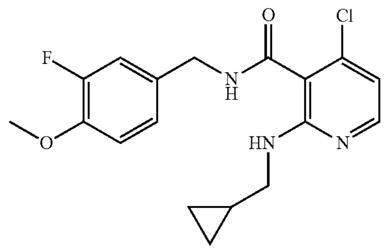 [SMILES: COc1ccc(CNC(=O)c2c(Cl)ccnc2NCC2CC2)cc1F] | 1H NMR (400 MHz, CDCl3): δ 8.01 (d, J = 5.6 Hz, 1H), 7.46-7.44 (m, 1H), 7.12-7.06 (m, 3H), 6.93 (t, J = 8.0 Hz, 1H), 6.53 (d, J = 5.2 Hz, 1H), 4.55 (d, J = 5.2 Hz, 2H), 3.88 (s, 3H), 3.07 (d, J = 6.8 Hz, 2H), 1.10-1.06 (m, 1H), 0.66-0.61 (m, 2H), 0.31-0.27 (m, 2H); m/z (ESI+) (M + H)+ = 364.10; HPLC tR = 5.72 min |

Preparation of Thioether Substituted Compounds

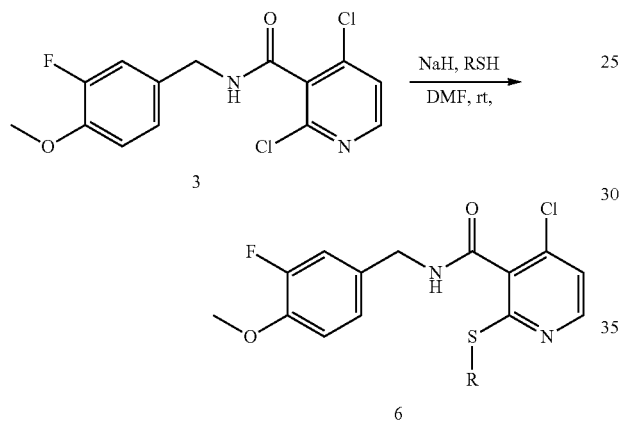

The compound 3 and mercaptan were dissolved in DMF, and then K₂CO₃ was added to the solution, the result suspension was stirred overnight at room temperature. TLC or HPLC monitor the reaction was completed, the mixture was diluted with EtOAc and H₂O, separated, dried, concentrated. The crude solid was crystallization with EtOAc/ether to get the desire product 6.

Below are illustrative examples of compound 6 prepared according to the process described above.

| Compound no. | RSH | Analytical Data |
|---|---|---|
| 213 | —SH | ¹H NMR (400 MHz, CDCl3): δ 8.23 (d, J = 5.6 Hz, 1H), 7.15 (dd, J1 = 12.0 Hz, J2 = 2.0 Hz, 1H), 7.12 (d, J = 8.8 Hz, 1H), 7.04 (d, J = 5.6 Hz, 1H), 6.93 (t, J = 8.4 Hz, 1H), 6.08-6.05 (m, 1H), 4.60 (d, J = 6.0 Hz, 2H), 3.87 (s, 3H), 2.50 (s, 3H); m/z (ESI) (M + H)+ = 341.10; HPLC tR = 6.41 min. |
| 214 |  | ¹H NMR (400 MHz, CDCl3): δ 8.20 (d, J = 5.6 Hz, 1H), 7.17 (dd, J1 = 12.0 Hz, J2 = 2.0 Hz, 1H), 7.11 (d, J = 8.0 Hz, 1H), 7.06 (d, J = 5.2 Hz, 1H), 6.93 (t, J = 8.4 Hz, 1H), 6.08-6.02 (m, 1H), 4.60 (d, J = 6.0 Hz, 2H), 3.88 (s, 3H), 3.01 (q, J = 7.6 Hz, 2), 1.39 (t, J = 7.6 Hz, 3H); m/z (ESI+) (M + H)+ = 355.10; HPLC tR = 6.05 min. |

| Compound no. | RSH | Analytical Data |
|---|---|---|
| 215 | ⌇⌇SH (propyl) | ¹H NMR (400 MHz, CDCl3): δ 8.19 (d, J = 5.6 Hz, 1H), 7.18 (dd, J1 = 11.6 Hz, J2 = 2.0 Hz, 1H), 7.11 (d, J = 8.4 Hz, 1H), 7.06 (d, J = 5.6 Hz, 1H), 6.93 (t, J = 8.4 Hz, 1H), 6.06-6.03 (m, 1H), 4.61 (d, J = 6.0 Hz, 2H), 3.88 (s, 3H), 2.95 (t, J = 7.6 Hz, 2H), 1.75 (q, J = 7.2 Hz, 2H), 1.07 (t, J = 7.2 Hz, 3H); m/z (ESI+) (M + H)+ = 369; HPLC tR = 6.92 min. |
| 216 | isopropyl-SH | ¹H NMR (400 MHz, CDCl3): δ 8.20 (d, J = 5.6 Hz, 1H), 7.19 (dd, J1 = 12.0 Hz, J2 = 2.0 Hz, 1H), 7.13-7.10 (m, 2H), 6.91 (t, J = 8.0 Hz, 1H), 6.06-6.02 (m, 1H), 4.60 (d, J = 6.0 Hz, 2H), 3.88 (s, 3H), 3.61-3.56 (m, 1H), 1.38 (d, J = 6.0 Hz, 6H); m/z (ESI+) M + H)+ = 369.10; HPLC tR = 6.91 min. |
| 217 | sec-butyl-SH | ¹H NMR (400 MHz, CDCl3): δ 8.20 (d, J = 5.6 Hz, 1H), 7.20 (dd, J1 = 11.2 Hz, J2 = 2.0 Hz, 1H), 7.13-7.10 (m, 2H), 6.93 (t, J = 8.4 Hz, 1H), 6.02-6.00 (m, 1H), 4.62-4.59 (m, 2H), 3.88 (s, 3H), 3.41-3.36 (m, 1H), 1.75-1.63 (m, 2H), 1.37 (d, J = 6.8 Hz, 3H), 1.03 (t, J = 7.6 Hz, 3H); m/z (ESI+) (M + H)+ = 383.15; HPLC tR = 6.76 min. |
| 218 | isobutyl-SH | ¹H NMR (400 MHz, CDCl3): δ 8.18 (d, J = 5.6 Hz, 1H), 7.18 (dd, J1 = 11.2 Hz, J2 = 2.0 Hz, 1H), 7.12 (d, J = 8.8 Hz, 1H), 7.05 (d, J = 5.6 Hz, 1H), 6.92 (t, J = 8.4 Hz, 1H), 6.07-6.04 (m, 1H), 4.61 (d, J = 6.0 Hz, 2H), 3.88 (s, 3H), 2.85 (d, J = 7.2 Hz, 2H), 1.98-1.93 (m, 1H), 1.06 (d, J = 6.8 Hz, 6H); m/z (ESI+) (M + H)+ = 383.15; HPLC tR = 7.21 min. |

Preparation of Sulfonyl Substituted Compounds

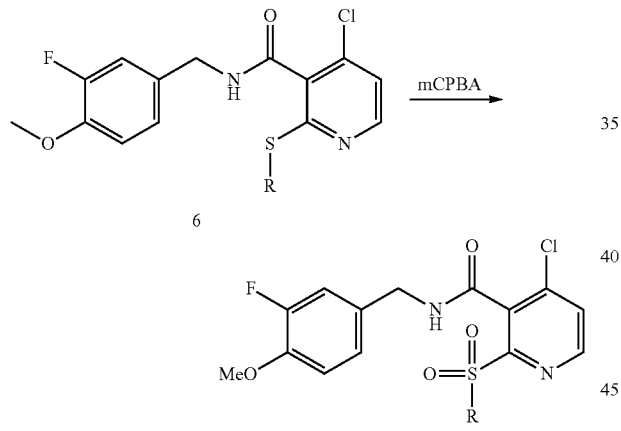

The compound 6 was dispersed in dichloromethane, then mCPBA was added to the suspension in potions at 0° C., removed the ice bath and the mixture was warmed to room temperature gradually, stiffed overnight at room temperature, TLC monitor the reaction completed, the mixture was diluted with dichloromethane and washed with aqueous NaOH organic phase was dried and concentrated, the residue was triturated in ether/EtOAc=2:1 to get the product as white crystal as compound 7.

Below are illustrative examples of compound 7 prepared according to the process described above.

| Compound no. | RSH | Analytical Data |
|---|---|---|
| 219 | —SH (methyl) | ¹H NMR (400 MHz, CDCl3): δ 8.69 (d, J = 4.8 Hz, 1H), 7.88 (d, J = 5.2 Hz, 1H), 7.20-7.13 (m, 2H), 6.93 (t, J = 8.4 Hz, 1H), 6.22-6.19 (m, 1H), 4.60 (d, J = 6.0 Hz, 2H), 3.88 (s, 3H), 3.29 (s, 3H); m/z (ESI+) (M + H)+ = 373; HPLC tR = 6.15 min. |

| Compound no. | RSH | Analytical Data |
| --- | --- | --- |
| 220 |  | ¹H NMR (400 MHz, DMSO-d6): δ 9.30-9.28 (m, 1H), 8.77 (d, J = 4.4 Hz, 1H), 7.89 (d, J = 4.8 Hz, 1H), 7.24 (dd, J1 = 12.4 Hz, J2 = 1.6 Hz, 1H), 7.18-7.09 (m, 2H), 4.41 (d, J = 6.0 Hz, 2H), 3.80 (s, 3H), 3.44 (q, J = 7.2 Hz, 2H), 1.11 (t, J = 7.2 Hz, 3H); m/z (ESI+) (M + H)+ = 387.20; HPLC tR = 6.40 min. |
| 221 |  | ¹H NMR (400 MHz, CDCl3): δ 8.66 (d, J = 4.8 Hz, 1H), 7.81 (d, J = 4.8 Hz, 1H), 7.18 (dd, J1 = 11.6 Hz, J2 = 2.0 Hz, 1H), 7.14 (d, J = 8.8 Hz, 1H), 6.93 (t, J = 8.4 Hz, 1H), 6.23-6.19 (m, 1H), 4.59 (d, J = 5.6 Hz, 2H), 3.88 (s, 3H), 3.40-3.36 (m, 2H), 1.78-1.72 (m, 2H), 1.04 (t, J = 7.2 Hz, 3H); m/z (ESI+) (M + H)+ = 401; HPLC tR = 6.76 min. |
| 222 |  | ¹H NMR (400 MHz, CDCl3): δ 8.66 (d, J = 5.2 Hz, 1H), 7.81 (d, J = 4.8 Hz, 1H), 7.18 (dd, J1 = 12.0 Hz, J2 = 2.0 Hz, 1H), 7.13 (d, J = 8.4 Hz, 1H), 6.93 (t, J = 8.4 Hz, 1H), 6.22-6.19 (m, 1H), 4.59 (d, J = 5.6 Hz, 2H), 3.88 (s, 3H), 3.79-3.77 (m, 1H), 1.29 (d, J = 6.4 Hz, 6H); m/z (ESI+) (M + H)+ = 401.10; HPLC tR = 6.78 min. |
| 223 |  | ¹H NMR (400 MHz, CDCl3): δ 8.66 (d, J = 4.8 Hz, 1H), 7.80 (d, J = 4.8 Hz, 1H), 7.18 (dd, J1 = 12.0 Hz, J2 = 1.6 Hz, 1H), 7.13 (d, J = 8.4 Hz, 1H), 6.93 (t, J = 8.4 Hz, 1H), 6.23-6.19 (m, 1H), 4.59 (d, J = 5.6 Hz, 2H), 3.88 (s, 3H), 3.60-3.56 (m, 1H), 1.90-1.80 (m, 1H), 1.59-1.54 (m, 1H), 1.26 (d, J = 7.2 Hz, 3H), 1.00 (t, J = 7.6 Hz, 3H); m/z (ESI+) (M + H)+ = 415.20; HPLC tR = 8.91 min. |
| 224 |  | ¹H NMR (400 MHz, DMSO-d6): δ 9.32-9.28 (m, 1H), 8.76 (d, J = 5.2 Hz, 1H), 7.92 (d, J = 5.2 Hz, 1H), 7.26 (dd, J1 = 12.4 Hz, J2 = 2.0 Hz, 1H), 7.18-7.08 (m, 2H), 4.40 (d, J = 5.6 Hz, 2H), 3.80 (s, 3H), 3.38-3.36 (m, 2H), 2.09-2.06 (m, 1H), 0.96 (d, J = 6.4 Hz, 6H); m/z (ESI+) (M + H)+ = 415.25; HPLC tR = 7.08 min. |

Preparation of Intermediate 9

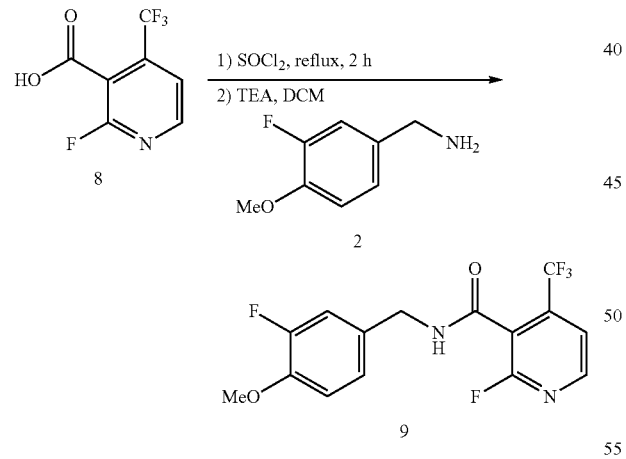

A solution of compound 8 (2.0 g, 9.6 mmol) in SOCl₂ was refluxed for 2 h. Then concentrated and re-dissolved in dichloromethane (10 mL), which was added to another solution of the amine 2 (1.2 g, 7.5 mmol) and TEA (0.96 g, 70 mmol) in dichloromethane (15 mL) at 0° C. After stirring overnight at room temperature, the reaction mixture was then poured into water and extracted with dichloromethane. The combined organic extracts were washed with brine, water and dried over Na₂SO₄, filtered and evaporated in vacuum. The resulting yellow solid was purified by flash column chromatography to provide the title compound 9 as a pale white solid (450 mg). ¹H NMR (400 MHz, CDCl3): δ 8.45 (t, J=2.8 Hz, 1H), 7.51 (d, J=5.2 Hz, 1H), 7.10-7.06 (m, 2H), 6.92 (dd, J1=11.2 Hz, J2=8.0 Hz, 1H), 4.58 (d, J=5.6 Hz, 2H), 3.89 (s, 3H); m/z (ESI+) (M+H)+=347.05.

Preparation of Ether Substituted Compounds

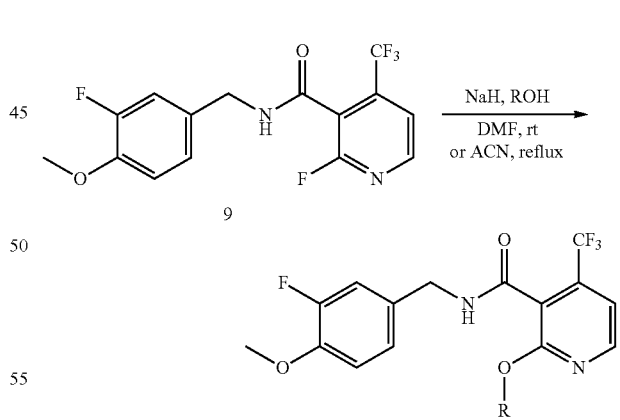

The compound 9 and alcohol were dissolved in DMF, and then 60% NaH was added to the solution. The mixture was stirred over night at room temperature. Then the mixture was diluted with EtOAc, and washed with H₂O and brine. The organic phase was separated and dried with Na₂SO₄, concentrated under reduced pressure and the residue was purified with thin-layer chromatography (Ether:EtOAc=3:2) to afford compound 10.

Below are illustrative examples of compound 10 prepared according to the process described above.

| Compound no. | ROH | Analytical Data |
|---|---|---|
| 225 | cyclopropylmethanol | $^1$H NMR (400 MHz, CDCl3): δ 8.29 (d, J = 5.2 Hz, 1H), 7.19 (dd, J1 = 11.2 Hz, J2 = 2.0 Hz, 1H), 7.12 (d, J = 5.2 Hz, 1H), 7.09 (d, J = 8.4 Hz), 6.91 (t, J = 8.4 Hz, 1H), 6.08-6.05 (m, 1H), 4.60 (d, J = 6.0 Hz, 2H), 4.21 (d, J = 8.0 Hz, 2H), 3.88 (s, 3H), 1.30-1.24 (m, 2H), 0.61-0.56 (m, 2H), 0.34-0.31 (m, 2H); m/z (ESI+) (M + H)+ = 399.25; |
| 226 | isobutanol | $^1$H NMR (400 MHz, CDCl3): δ 8.29 (d, J = 5.6 Hz, 1H), 7.15-7.05 (m, 3H), 6.91 (t, J = 8.4 Hz, 1H), 6.07-6.04 (m, 1H), 4.56 (d, J = 6.0 Hz, 2H), 4.12 (d, J = 6.8 Hz, 2H), 3.88 (s, 3H), 2.08-2.02 (m, 1H), 0.95 (d, J = 6.8 Hz, 6H); m/z (ESI+) (M + H)+ = 401.25. |
| 227 | isopropanol | $^1$H NMR (400 MHz, CDCl3): δ 8.30 (d, J = 5.6 Hz, 1H), 7.16 (dd, J1 = 12.0 Hz, J2 = 2.0 Hz, 1H), 7.10-7.07 (m, 2H), 6.92 (t, J = 8.4 Hz, 1H), 6.01-5.97 (m, 1H), 5.39-5.36 (m, 1H), 4.58 (d, J = 6.0 Hz, 2H), 3.88 (s, 3H), 1.33 (d, J = 6.0 Hz, 6H); m/z (ESI+) (M + H)+ = 387. |
| 228 | 3-pentanol | $^1$H NMR (400 MHz, CDCl3): δ 8.28 (d, J = 5.2 Hz, 1H), 7.14 (dd, J1 = 11.4 Hz, J2 = 2.4 Hz, 1H), 7.10-7.07 (m, 2H), 6.92 (t, J = 8.4 Hz, 1H), 6.01-5.97 (m, 1H), 5.15-5.11 (m, 1H), 4.57 (d, J = 6.0 Hz, 2H), 3.88 (s, 3H), 1.71-1.63 (m, 4H), 0.88 (t, J = 8.0 Hz, 6H); m/z (ESI+) (M + H)+ = 415. |
| 229 | cyclobutylmethanol | $^1$H NMR (400 MHz, CDCl3): δ 8.31 (d, J = 5.6 Hz, 1H), 7.15-7.11 (m, 2H), 7.07 (d, J = 8.4 Hz, 1H), 6.93 (t, J = 8.4 Hz, 1H), 6.02-5.98 (m, 1H), 4.57 (d, J = 6.0 Hz, 2H), 4.34 (d, J = 6.8 Hz, 2H), 3.89 (s, 3H), 2.77-2.72 (m, 1H), 2.09-2.05 (m, 2H), 1.93-1.77 (m, 4H); m/z (ESI+) (M + H)+ = 413. |
| 230 | cyclopentylmethanol | $^1$H NMR (400 MHz, CDCl3): δ 8.30 (d, J = 5.6 Hz, 1H), 7.16-7.07 (m, 3H), 6.92 (t, J = 8.4 Hz, 1H), 6.04-6.01 (m, 1H), 4.58 (d, J = 5.6 Hz, 2H), 4.23 (d, J = 7.6 Hz, 2H), 3.88 (s, 3H), 2.34-2.31 (m, 1H), 1.76-1.71 (m, 2H), 1.62-1.53 (m, 4H), 1.30-1.25 (m, 2H); m/z (ESI+) (M + H)+ = 427.30. |

Preparation of Intermediate 16

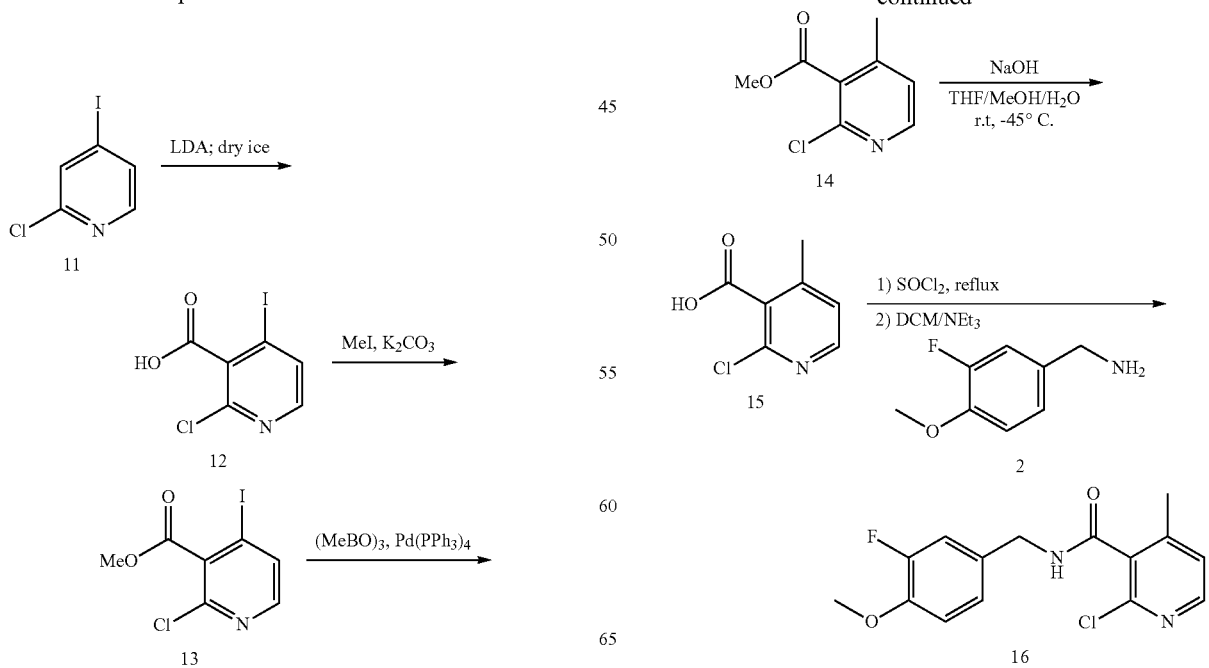

To a solution of compound 11 (5.70 g, 23.7 mmol) in THF (56 mL) was added LDA (28.4 mmol in 45 mL of THF) dropwise at −78° C. The reaction was stirred for 60 min. The resulting reaction mixture was added into a solution of dry-ice (30 g) in THF. After stirring for 1 h under $N_2$, the reaction was quenched by water and partitioned between EA (50 mL) and $Na_2CO_3$ (sol. in water). The aqueous phase was extracted with EA (keep the pH>12). The aqueous phase was concentrated under reduced pressure to give the product 12 (8.6 g containing i-$Pr_2NH$). Used directly for the next step.

To a solution of compound 12 (8.60 g) in DMF (56 mL) was added $K_2CO_3$ (6.54 g, 47.4 mmol) followed with MeI (18.0 g, 118.5 mmol). The reaction was stirred overnight. Water (100 mL) was added into the mixture. $Et_2O$ was added to extract the product, washed by water and dried over $Na_2SO_4$. Concentrated and purified by FCC (PE/EA=50:1) to afford 4.0 g of the product 13 (57% for 2 steps.)

To a solution of compound 13 (5.5 g, 18.5 mmol) in DMF (50 mL) was added $K_2CO_3$ (10.2 g, 74 mmol), trimethylboroxine (4.64 g, 3.70 mmol) and $Pd(PPh_3)_4$ (2.1 g, 1.85 mmol) in DMF under $N_2$. The reaction mixture was stirred at 110° C. for 120 min under $N_2$. After cooled down, water (100 mL) was added into the mixture. $Et_2O$ was added to extract the product, washed by water and dried over $Na_2SO_4$. Concentrated and purified by FCC (PE/EA=40:1) to afford 2.7 g of the product 14 (79%).

To a solution of compound 14 (2.7 g, 14.5 mmol) in THF-MeOH—H2O (4:4:1, 36 mL) was added NaOH (1.74 g, 43.5 mmol). The reaction mixture was stirred at 35° C. for 12 h. The mixture was concentrated to remove the organic solution. The EtOAc-HCl was added to adjust the pH value to about 3.0, and then concentrated to afford a solid. The solid was dissolved into DCM-MeOH (10:1, 50 mL). Filtered and concentrated to afford the product 15 (2.3 g, 92.7% yield).

To a solution of compound 15 (2.3 g, 13.5 mmol) in $SOCl_2$ (20 mL) was refluxed for 4 h, The mixture was concentrated and then re-dissolved in DCM (5 mL) and transferred to a solution of the amine 2 (2.7 g 17.6 mmol) and TEA (4.0 g, 40.5 mmol). The mixture was stirred at rt for 3 h. The resulting mixture was purified by FCC (PE/EA=3:1) to afford the product 16 (3.1 g, 75.3%). $^1$H NMR (400 MHz, CDCl3): δ 8.19 (d, J=4.8 Hz, 1H), 7.11-7.06 (m, 3H), 6.92 (t, J=8.8 Hz, 1H), 6.32-6.28 (m, 1H), 4.55 (d, J=6.0 Hz, 2H), 3.87 (s, 3H), 2.34 (s, 3H); m/z (ESI+) (M+H)+=309.00.

Preparation of Ether Substituted Compounds

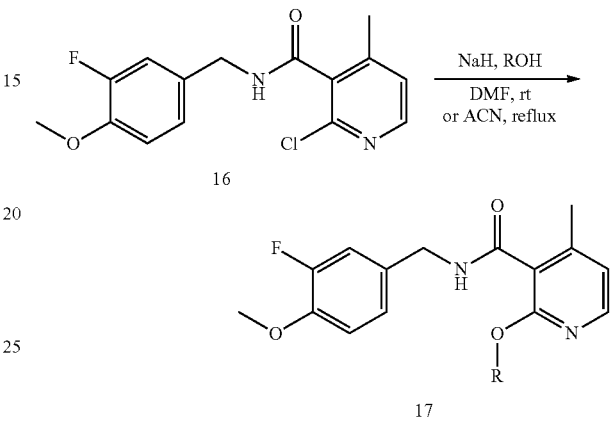

The compound 16 and alcohol were dissolved in DMF, and then 60% NaH was added to the solution. The mixture was stirred over night at room temperature. Then the mixture was diluted with EtOAc, and washed with $H_2O$ and brine. The organic phase was separated and dried with $Na_2SO_4$, concentrated under reduced pressure and the residue was purified with thin-layer chromatography (Ether:EtOAc=3:2) to afford compound 17.

Below are illustrative examples of compound 17 prepared according to the process described above.

| Compound no. | ROH | Analytical Data |
|---|---|---|
| 231 | cyclopropylmethanol | $^1$H NMR (400 MHz, CDCl3): δ 7.98 (d, J = 5.2 Hz, 1H), 7.20 (d, J = 11.6 Hz, 1H), 7.10 (d, J = 8.4 Hz, 1H), 6.91 (t, J = 8.4 Hz, 1H), 6.75 (d, J = 4.8 Hz), 6.62-6.60 (m, 1H), 4.59 (d, J = 6.0 Hz, 2H), 4.14 (d, J = 8.0 Hz, 2H), 3.88 (s, 3H), 2.43 (s, 3H), 1.25-1.20 (m, 2H), 0.55-0.52 (m, 2H), 0.28-0.26 (m, 2H); m/z (ESI+) (M + H)+ = 345.10. |
| 232 | isobutanol | $^1$H NMR (400 MHz, CDCl3): δ 7.99-7.97 (m, 1H), 7.12 (d, J = 11.6 Hz, 1H), 7.07 (d, J = 8.4 Hz, 1H), 6.92-6.88 (m, 1H), 6.75-6.72 (m, 1H), 6.49-6.47 (m, 1H), 4.55-4.53 (m, 2H), 4.07-4.04 (m, 2H), 3.88 (s, 3H), 2.39 (s, 3H), 2.01-1.98 (m, 1H), 0.92-0.89 (m, 6H); m/z (ESI+) (M + H)+ = 347.15. |
| 233 | isopropanol | $^1$H NMR (400 MHz, CDCl3): δ 7.99 (d, J = 5.2 Hz, 1H), 7.20 (dd, J1 = 11.6 Hz, J2 = 2.0 Hz, 1H), 7.10 (d, J = 8.0 Hz, 1H), 6.92 (t, J = 8.8 Hz, 1H), 6.72 (d, J = 4.8 Hz), 6.43-6.41 (m, 1H), 5.36-5.33 (m, 1H), 4.57 (d, J = 6.0 Hz, 2H), 3.88 (s, 3H), 2.40 (s, 3H), 1.29 (d, J = 6.0 Hz, 6H); m/z (ESI+) (M + H)+ = 333.10. |
| 234 | sec-pentanol | $^1$H NMR (400 MHz, CDCl3): δ 7.98 (d, J = 4.8 Hz, 1H), 7.14 (dd, J1 = 12 Hz, J2 = 2.0 Hz, 1H), 7.08 (d, J = 8.8 Hz, 1H), 6.91 (t, J = 8.4 Hz, 1H), 6.71 (d, J = 5.2 Hz), 6.43-6.41 (m, 1H), 5.12-5.09 (m, 1H), 4.55 (d, J = 6.4 Hz, 2H), 3.88 (s, 3H), 2.40 (s, 3H), 1.62 (q, J = 7.6 Hz, 4H), 0.84 (t, J = 7.6 Hz, 6H); m/z (ESI+) (M + H)+ = 361.15. |

| Compound no. | ROH | Analytical Data |
|---|---|---|
| 235 | 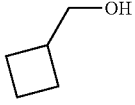 | ¹H NMR (400 MHz, CDCl3): δ 7.99 (d, J = 5.2 Hz, 1H), 7.13 (dd, J1 = 11.6 Hz, J2 = 2.0 Hz, 1H), 7.07 (d, J = 8.0 Hz, 1H), 6.92 (t, J = 8.4 Hz, 1H), 6.75 (d, J = 5.2 Hz, 6.51-6.49 (m, 1H), 4.55 (d, J = 6.0 Hz, 2H), 4.28 (d, J = 7.2 Hz, 2H), 3.89 (s, 3H), 2.70-2.66 (m, 1H), 2.43 (s, 3H), 2.04-1.72 (m, 6H); m/z (ESI+) (M + H)+ = 359.10. |
| 236 | 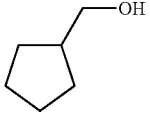 | ¹H NMR (400 MHz, CDCl3): δ 7.99 (d, J = 5.2 Hz, 1H), 7.13 (dd, J1 = 11.6 Hz, J2 = 2.0 Hz, 1H), 7.08 (d, J = 8.8 Hz, 1H), 6.91 (t, J = 8.4 Hz, 1H), 6.75 (d, J = 5.2 Hz), 6.57-6.53 (m, 1H), 4.55 (d, J = 6.0 Hz, 2H), 4.16 (d, J = 7.6 Hz, 2H), 3.88 (s, 3H), 2.41 (s, 3H), 2.26-2.23 (m, 1H), 1.68-1.63 (m, 2H), 1.59-1.50 (m, 4H), 1.26-1.22 (m, 2H); m/z (ESI+) (M + H)+ = 373.25. |
| 237 | 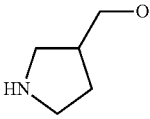 | ¹H NMR (400 MHz, CD3OD): δ 8.01 (d, J = 5.6 Hz, 1H), 7.19-7.05 (m, 3H), 6.90 (d, J = 4.8 Hz, 1H), 5.34 (t, J = 4.8 Hz, 1H), 4.59 (s, 2H), 4.48 (s, 2H), 4.48-4.29 (m, 2H), 3.86 (s, 3H), 3.40-3.35 (m, 1H), 3.28-3.23 (m, 2H), 3.13-3.09 (m, 1H), 2.83-2.79 (m, 1H), 2.20-2.13 (m, 1H), 1.86-1.80 (m, 1H); m/z (ESI+) (M + H)+ = 374.15. |
| 238 | 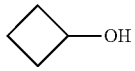 | ¹H NMR (400 MHz, CDCl3): δ 7.97 (d, J = 6.0 Hz, 1H), 7.17 (dd, J1 = 12.0 Hz, J2 = 2.4 Hz, 1H), 6.93 (t, J = 8.4 Hz, 1H), 6.74 (d, J = 4.8 Hz, 1H), 6.45-6.40 (m, 1H), 5.24-5.19 (m, 1H), 4.58 (d, J = 6.0 Hz, 2H), 3.88 (s, 3H), 2.45-2.40 (m, 2H), 2.38 (s, 3H), 2.08-2.03 (m, 2H), 1.82-1.75 (m, 1H), 1.70-1.60 (m, 1H); m/z (ESI+) (M + H)+ = 345.05. |

Preparation of Intermediate 20

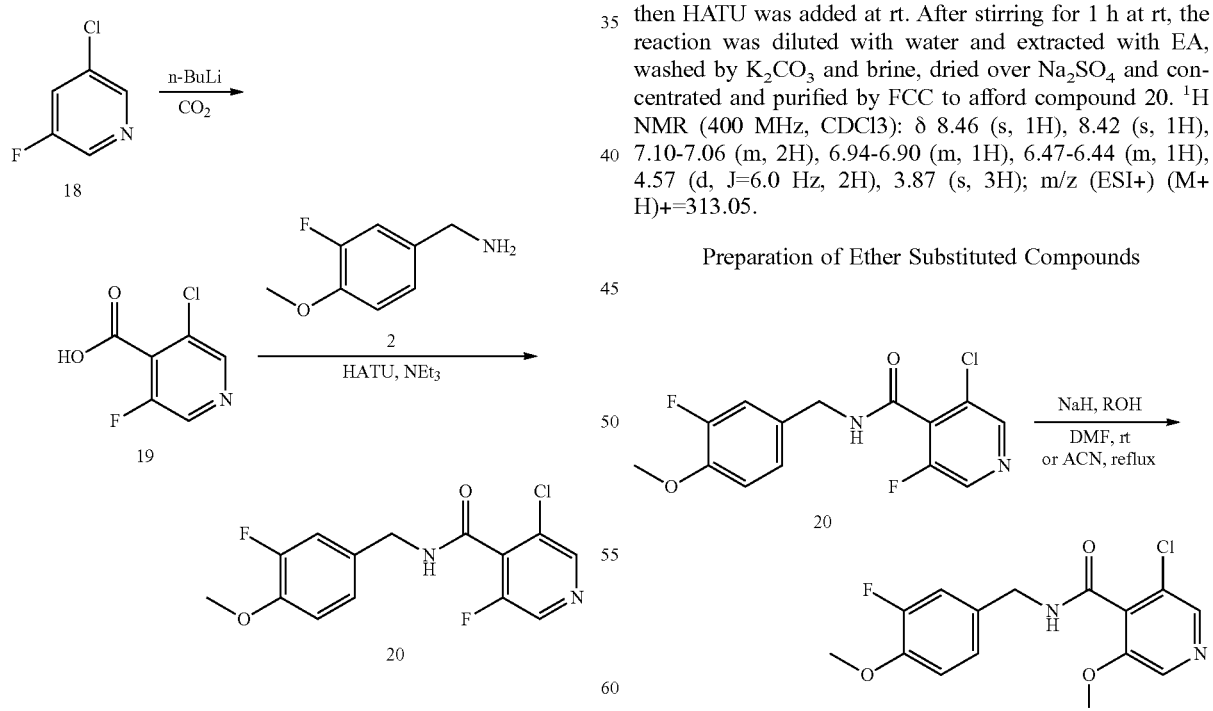

To a solution of compound 18 (2 g) in THF (20 mL), n-BuLi (7 ml) was added slowly at −78° C., with N₂ gas. The reaction was stirred for 60 min. The resulting reaction mixture was added into a solution of dry-ice. After stirring overnight under N₂, The reaction was quenched by 1N HCl until the pH value was adjusted to 1. The mixture was extracted with EA. The organic phase was dried over Na₂SO₄ and concentrated under reduced pressure to give the product 19.

To a solution of compound 2, 19 and Et₃N in DMF at rt. then HATU was added at rt. After stirring for 1 h at rt, the reaction was diluted with water and extracted with EA, washed by K₂CO₃ and brine, dried over Na₂SO₄ and concentrated and purified by FCC to afford compound 20. ¹H NMR (400 MHz, CDCl3): δ 8.46 (s, 1H), 8.42 (s, 1H), 7.10-7.06 (m, 2H), 6.94-6.90 (m, 1H), 6.47-6.44 (m, 1H), 4.57 (d, J=6.0 Hz, 2H), 3.87 (s, 3H); m/z (ESI+) (M+H)+=313.05.

Preparation of Ether Substituted Compounds

The compound 20 and alcohol were dissolved in DMF, and then 60% NaH was added to the solution. The mixture was stirred over night at room temperature. Then the mixture was diluted with EtOAc, and washed with H$_2$O and brine. The organic phase was separated and dried with Na$_2$SO$_4$, concentrated under reduced pressure and the residue was purified with thin-layer chromatography (Ether:EtOAc=3:2) to afford compound 21.

Below are illustrative examples of compound 21 prepared according to the process described above.

| Compound no. | ROH | Analytical Data |
|---|---|---|
| 239 | cyclopropylmethyl-OH | $^1$H NMR (400 MHz, CDCl3): δ 8.27 (s, 1H), 8.20 (s, 1H), 7.14 (d, J = 12 Hz, 1H), 7.20 (dd, J1 = 12.0 Hz, J2 = 2.4 Hz, 1H), 7.10 (d, J = 8.4 Hz, 1H), 6.92 (t, J = 8.4 Hz, 1H), 6.14-6.12 (m, 1H), 4.62 (d, J = 6.4 Hz, 2H), 3.95 (d, J = 6.8 Hz, 2H), 3.88 (s, 3H), 1.30-1.22 (m, 1H), 0.67-0.63 (m, 2H), 0.36-0.32 (m, 2H); m/z (ESI+) (M + H)+ = 365.15. |
| 240 | isobutyl-OH | $^1$H NMR (400 MHz, CDCl3): δ 8.26 (s, 1H), 8.20 (s, 1H), 7.14 (d, J = 12 Hz, 1H), 7.08 (d, J = 9.2 Hz, 1H), 6.91 (t, J = 8.0 Hz, 1H), 6.06-6.04 (m, 1H), 4.59 (d, J = 6.0 Hz, 2H), 3.88 (s, 3H), 3.85 (d, J = 6.8 Hz, 2H), 2.09-2.06 (m, 1H), 0.96 (d, J = 6.8 Hz, 6H); m/z (ESI+) (M + H)+ = 367.05. |
| 241 | cyclobutylmethyl-OH | $^1$H NMR (400 MHz, CDCl3): δ 8.26 (s, 1H), 8.20 (s, 1H), 7.13 (dd, J1 = 12 Hz, J2 = 2.4 Hz, 1H), 7.07 (d, J = 8.8 Hz, 1H), 6.91 (t, J = 8.4 Hz, 1H), 6.09-6.07 (m, 1H), 4.59 (d, J = 6.0 Hz, 2H), 4.06 (d, J = 6.4 Hz, 1H), 3.88 (s, 3H), 2.75-2.72 (m, 1H), 2.10-1.78 (m, 6H); m/z (ESI+) (M + H)+ = 379.15. |
| 242 | cyclopentylmethyl-OH | $^1$H NMR (400 MHz, CDCl3): δ 8.25 (s, 1H), 8.20 (s, 1H), 7.14 (dd, J1 = 12 Hz, J2 = 2.4 Hz, 1H), 7.08 (d, J = 8.4 Hz, 1H), 6.91 (t, J = 8.4 Hz, 1H), 6.11-6.09 (m, 1H), 4.58 (d, J = 6.4 Hz, 2H), 3.96 (d, J = 7.2 Hz, 1H), 3.88 (s, 3H), 3.34-3.30 (m, 1H), 1.78-1.73 (m, 2H), 1.60-1.56 (m, 4H), 1.30-1.25 (m, 2H); m/z (ESI+) (M + H)+ = 393.10. | multiple cloning sites of pETDuet-1 vector. (Novagen, CA, USA). All the vectors were transformed into BL21 *E. coli* host cells and subjected to 0.5 mM IPTG induction for protein expression at 30° C. Purifications of the recombinant proteins by affinity nickel columns (HisTrap, GE Healthy Science, USA) were carried out using standard protocols according to manufacturer's instructions (Novagen, USA).

Example 2

Enzymatic Assay:

ALDH2 catalyzes the oxidative reaction of substrate acetaldehyde to acetic acid using NAD$^+$ as a cofactor. Enzymatic activity, or catalytic rate, of aldehyde dehydrogenase (ALDH2) can be measured spectrophotometrically at UV wavelength λ340 nm by the accumulation of reduced product NADH derived from NAD$^+$. Absorbance at λ340 nm is quantitatively proportional to the amount of NADH being produced over time (6.22 O.D. unit=1 mmole of NADH, measured in a 1-cm width standard cuvette). This method is well-established in the literature [e.g. D. K. Rex, W. F. Bosron, J. E. Smialek, T. K. Li, *Alcohol Clin Exp Res* 9, 147 (1985)].

Cloning, Expression and Purification of Human ALDH2 Wild Type and ALDH2*2 Recombinant Mutant Enzymes:

Full-length wild type human ALDH2 cDNA was purchased from ATCC (No. MGC-1806. GenBank ID: BC002967). The 18-amino acid mitochondria transport signal sequence was removed by PCR and cloned into the NheI/HindIII sites of a His-tag vector, pTrcHis, using standard molecular cloning techniques. The human ALDH2* cDNA construct containing the Asian E487K mutation was obtained by site-directed mutagenesis to create the E487K substitution of the wild type ALDH2. Both human clones were designed to express a recombinant protein with the His-tag at the N-terminus of the protein. For the co-expression experiments of human ALDH2 wild type and ALDH2*2 heterotetramers, a wild type ALDH2 gene and a ALDH2 E487K gene were inserted separately into the two Control 1 is

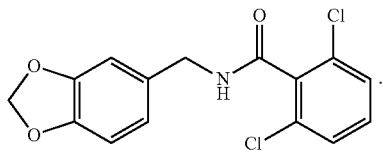 [SMILES: O=C(NCc1ccc2c(c1)OCO2)c1c(Cl)cccc1Cl]

Control 1 and compound 161 are used as benchmarks and the symbols have the following representation:

−: no activation or inhibition

+: activation less than control 1

++: activation similar to control 1, within 10%

+++: activation more than control 1 and less than control (compound 161)

++++: activation similar to compound 161, within 10%

TABLE 2

| Compound no. | Structure | ALDH2 (mutant) | ALDH2 (wild-type) |
|---|---|---|---|
| Control 1 | 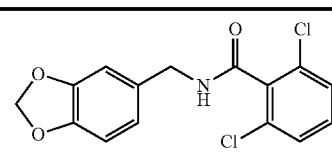 | ++ | ++ |

TABLE 2-continued

| Compound no. | Structure | ALDH2 (mutant) | ALDH2 (wild-type) |
|---|---|---|---|
| 100 | 3-Cl,4-OMe-benzyl-NH-C(O)-2,6-diCl-phenyl | + | + |
| 101 | 3-OH,4-OMe-benzyl-NH-C(O)-2,6-diCl-phenyl | + | + |
| 102 | 3-F,4-OMe-benzyl-NH-C(O)-2,6-diCl-phenyl | ++ | ++ |
| 103 | 3-OMe-benzyl-NH-C(O)-2,6-diCl-phenyl | + | + |
| 104 | 3-Cl,4-OMe-benzyl-NH-C(O)-2-Cl,6-Br-phenyl | + | + |
| 105 | 3-OH,4-OMe-benzyl-NH-C(O)-2-Cl,6-Br-phenyl | + | − |
| 106 | 3-F,4-OMe-benzyl-NH-C(O)-2-Cl,6-Br-phenyl | ++ | + |
| 107 | 3-OMe-benzyl-NH-C(O)-2-Cl,6-Br-phenyl | + | + |
| 108 | 4-OMe-benzyl-NH-C(O)-2-Cl,6-Br-phenyl | + | ++ |
| 109 | 3-F,4-OMe-benzyl-NH-C(O)-2-Cl-6-(NHCH2CH2OH)-phenyl | ++ | + |
| 110 | 3-F,4-OMe-benzyl-NH-C(O)-2-Cl-6-OPh-phenyl | ++ | + |
| 111 | 4-NMe2-benzyl-NH-C(O)-2,6-diCl-phenyl | − | − |
| 112 | 4-SO2Me-benzyl-NH-C(O)-2,6-diCl-phenyl | + | + |
| 113 | 4-OMe-benzyl-NH-C(O)-2-Me,6-Br-phenyl | + | + |
| 114 | 4-OMe-benzyl-NH-C(O)-2,6-diMe-phenyl | + | + |
| 115 | 4-OMe-benzyl-NH-C(O)-2-Me,5-Br-phenyl | + | + |
| 116 | 4-OMe-benzyl-NH-C(O)-2-Me,4-Br-phenyl | + | + |
| 117 | 3-F,4-OMe-benzyl-NH-C(O)-2-Me-6-(NH-iBu)-phenyl | ++ | + |

TABLE 2-continued

| Compound no. | Structure | ALDH2 (mutant) | ALDH2 (wild-type) |
|---|---|---|---|
| 118 | 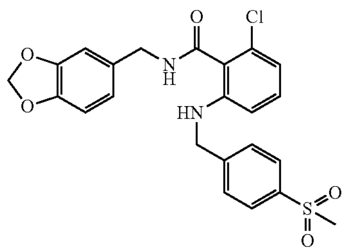 [SMILES: CS(=O)(=O)c1ccc(CNc2cccc(Cl)c2C(=O)NCc2ccc3c(c2)OCO3)cc1] | + | + |
| 119 | 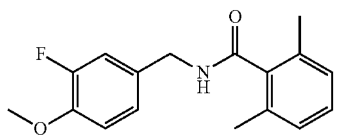 [SMILES: COc1ccc(CNC(=O)c2c(C)cccc2C)cc1F] | + | − |
| 120 | 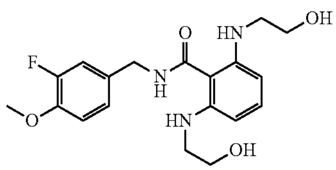 [SMILES: COc1ccc(CNC(=O)c2c(NCCO)cccc2NCCO)cc1F] | + | − |
| 121 | 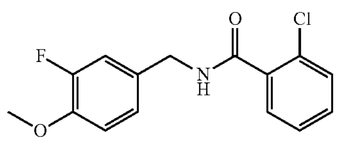 [SMILES: COc1ccc(CNC(=O)c2ccccc2Cl)cc1F] | + | + |
| 122 | 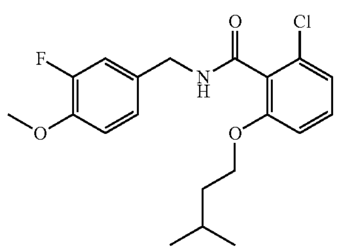 | ++ | + |
| 123 | 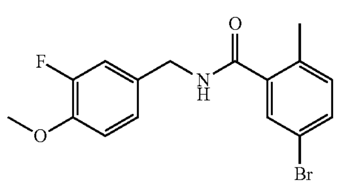 [SMILES: COc1ccc(CNC(=O)c2cc(Br)ccc2C)cc1F] | + | + |
| 124 | 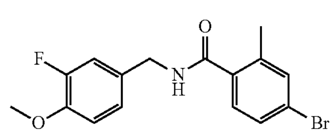 [SMILES: COc1ccc(CNC(=O)c2ccc(Br)cc2C)cc1F] | + | + |
| 125 | 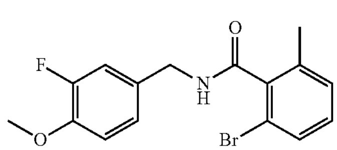 [SMILES: COc1ccc(CNC(=O)c2c(C)cccc2Br)cc1F] | + | + |
| 126 | | −− | −− |
| 127 | | + | + |
| 128 | | + | + |
| 129 | | − | − |
| 130 | | − | − |
| 131 | | + | + |
| 132 | | + | + |

TABLE 2-continued
| Compound no. | Structure | ALDH2 (mutant) | ALDH2 (wild-type) |
|---|---|---|---|
| 133 | 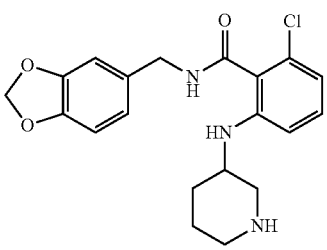 [SMILES: O=C(NCc1ccc2c(c1)OCO2)c1c(Cl)cccc1NC1CCCNC1] | + | + |
| 134 | 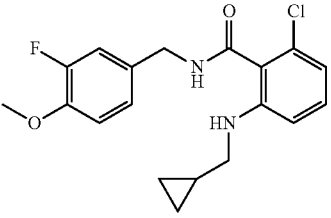 [SMILES: COc1ccc(CNC(=O)c2c(Cl)cccc2NCC2CC2)cc1F] | +++ | +++ |
| 135 | 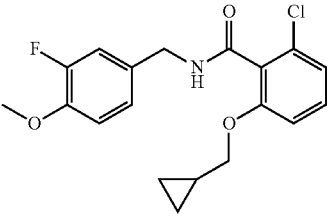 | ++++ | ++++ |
| 136 | 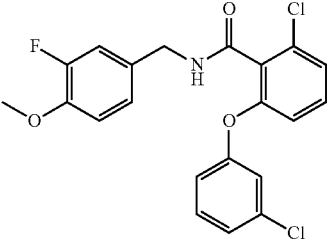 [SMILES: COc1ccc(CNC(=O)c2c(Cl)cccc2Oc2cccc(Cl)c2)cc1F] | ++ | ++ |
| 137 | 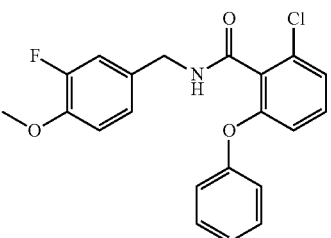 | + | ++ |
| 138 | 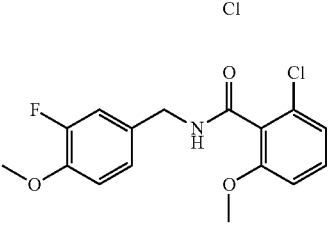 | +++ | ++ |
| 139 | 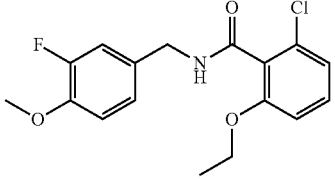 | +++ | ++ |
| 140 | 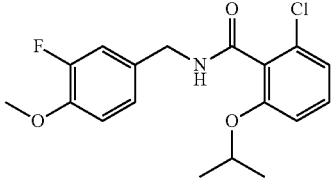 [SMILES: COc1ccc(CNC(=O)c2c(Cl)cccc2OC(C)C)cc1F] | +++ | +++ |
| 141 | 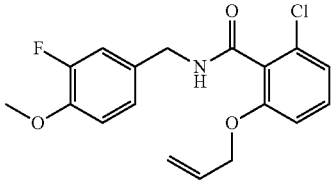 [SMILES: C=CCOc1cccc(Cl)c1C(=O)NCc1ccc(OC)c(F)c1] | +++ | ++ |
| 142 | 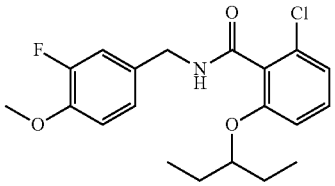 [SMILES: CCC(CC)Oc1cccc(Cl)c1C(=O)NCc1ccc(OC)c(F)c1] | +++ | ++ |
| 143 | 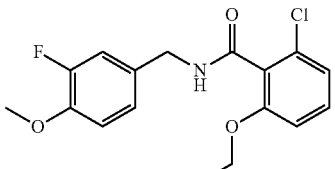 | ++ | ++ |
| 144 | 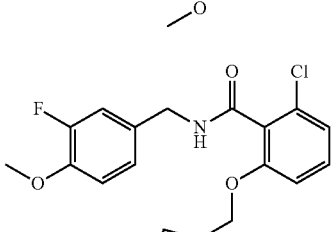 | +++ | +++ |
| 145 | 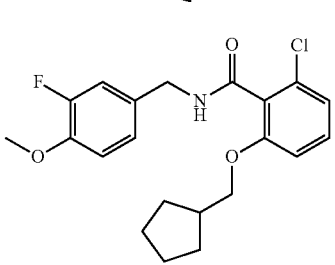 | +++ | ++ |

TABLE 2-continued

| Compound no. | Structure | ALDH2 (mutant) | ALDH2 (wild-type) |
|---|---|---|---|
| 146 | | +++ | ++ |
| 147 | | +++ | +++ |
| 148 | | + | + |
| 149 | | ++++ | ++++ |
| 150 | | ++ | +++ |
| 151 | | ++++ | ++++ |
| 152 | 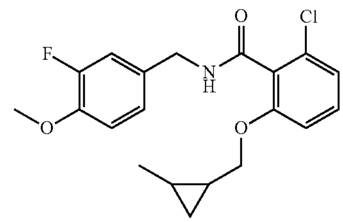 [SMILES: COc1ccc(CNC(=O)c2c(Cl)cccc2OCC2CC2C)cc1F] | +++ | +++ |
| 153 | 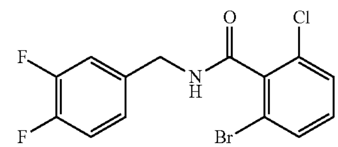 [SMILES: O=C(NCc1ccc(F)c(F)c1)c1c(Cl)cccc1Br] | + | + |
| 154 | 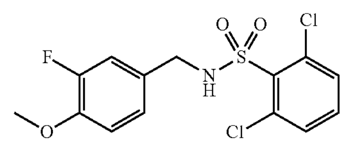 [SMILES: COc1ccc(CNS(=O)(=O)c2c(Cl)cccc2Cl)cc1F] | + | + |
| 155 | 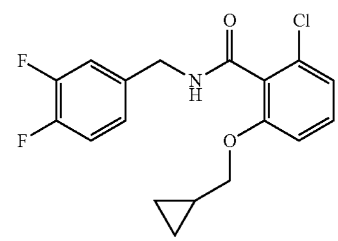 [SMILES: O=C(NCc1ccc(F)c(F)c1)c1c(Cl)cccc1OCC1CC1] | ++ | + |
| 156 | 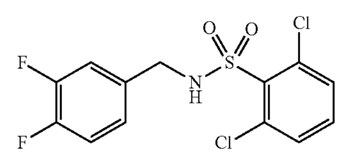 [SMILES: O=S(=O)(NCc1ccc(F)c(F)c1)c1c(Cl)cccc1Cl] | + | − |
| 157 | 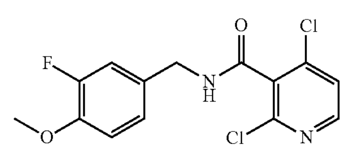 [SMILES: COc1ccc(CNC(=O)c2c(Cl)ccnc2Cl)cc1F] | ++ | ++ |
| 158 | 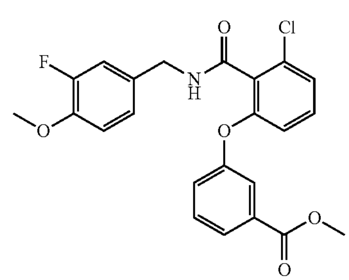 | + | ++ |

TABLE 2-continued

| Compound no. | Structure | ALDH2 (mutant) | ALDH2 (wild-type) |
|---|---|---|---|
| 159 | 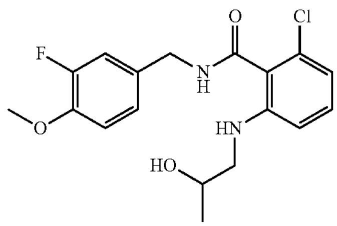 [SMILES: COc1ccc(CNC(=O)c2c(Cl)cccc2NCC(C)O)cc1F] | ++ | ++ |
| 160 | 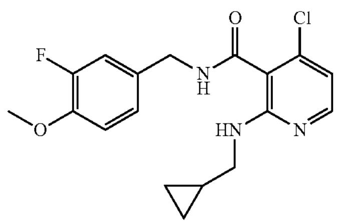 | ++ | ++ |
| 161 | 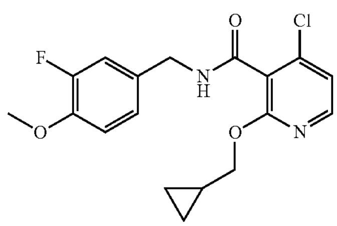 | ++++ | ++++ |
| 162 | 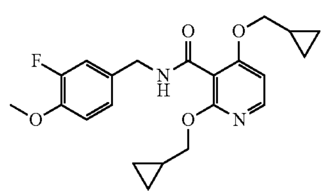 [SMILES: COc1ccc(CNC(=O)c2c(OCC3CC3)ccnc2OCC2CC2)cc1F] | ++ | + |
| 163 | 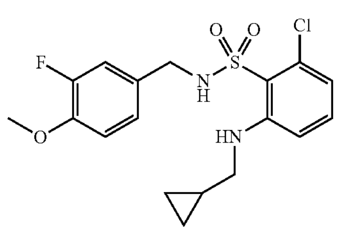 | + | + |
| 164 | 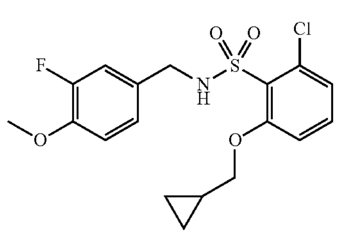 | + | + |
| 165 | 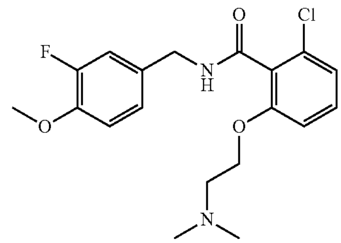 | ++ | ++ |
| 166 | 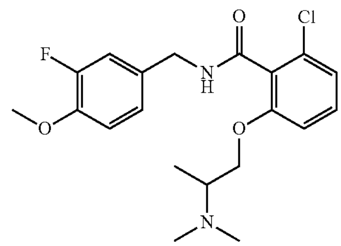 [SMILES: COc1ccc(CNC(=O)c2c(Cl)cccc2OCC(C)N(C)C)cc1F] | ++ | ++ |
| 167 | 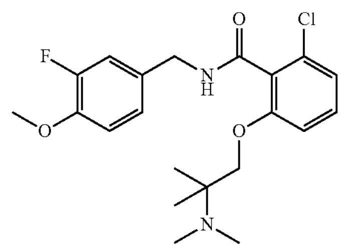 [SMILES: COc1ccc(CNC(=O)c2c(Cl)cccc2OCC(C)(C)N(C)C)cc1F] | + | + |
| 168 | 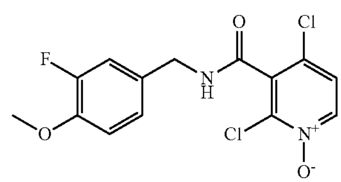 [SMILES: COc1ccc(CNC(=O)c2c(Cl)cc[n+]([O-])c2Cl)cc1F] | + | + |
| 169 | 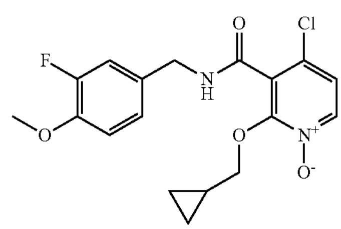 [SMILES: COc1ccc(CNC(=O)c2c(Cl)cc[n+]([O-])c2OCC2CC2)cc1F] | ++ | + |
| 170 | 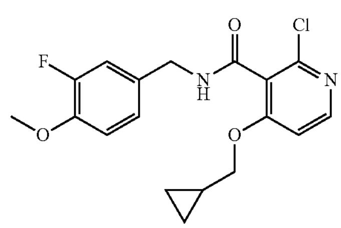 [SMILES: COc1ccc(CNC(=O)c2c(OCC3CC3)ccnc2Cl)cc1F] | +++ | ++ |
| 171 | 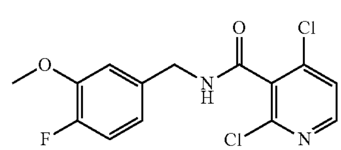 [SMILES: COc1cc(CNC(=O)c2c(Cl)ccnc2Cl)ccc1F] | − | − |

TABLE 2-continued

| Compound no. | Structure | ALDH2 (mutant) | ALDH2 (wild-type) |
|---|---|---|---|
| 172 | 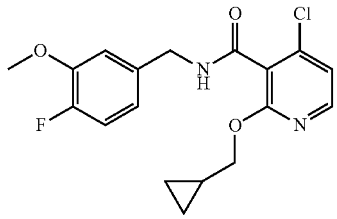 [SMILES: COc1cc(CNC(=O)c2c(Cl)ccnc2OCC2CC2)ccc1F] | + | + |
| 173 | 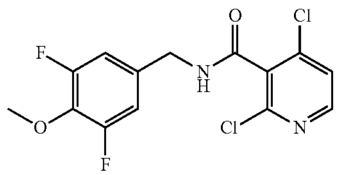 [SMILES: COc1c(F)cc(CNC(=O)c2c(Cl)ccnc2Cl)cc1F] | ++ | + |
| 174 | 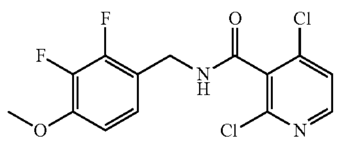 [SMILES: COc1ccc(CNC(=O)c2c(Cl)ccnc2Cl)c(F)c1F] | ++ | + |
| 175 | 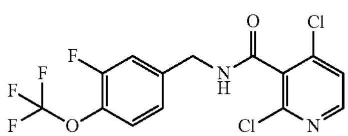 [SMILES: O=C(NCc1ccc(OC(F)(F)F)c(F)c1)c1c(Cl)ccnc1Cl] | ++ | + |
| 176 | 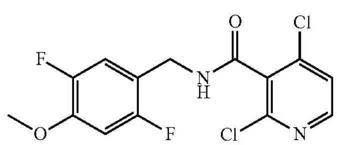 [SMILES: COc1cc(F)c(CNC(=O)c2c(Cl)ccnc2Cl)cc1F] | ++ | ++ |
| 177 | 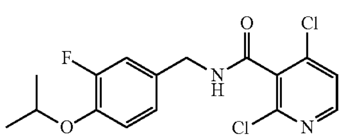 [SMILES: CC(C)Oc1ccc(CNC(=O)c2c(Cl)ccnc2Cl)cc1F] | − | − |
| 178 | 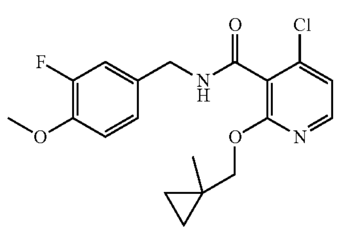 [SMILES: COc1ccc(CNC(=O)c2c(Cl)ccnc2OCC2(C)CC2)cc1F] | ++++ | ++++ |
| 179 | 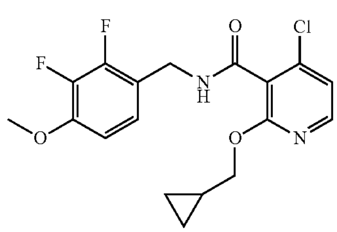 [SMILES: COc1ccc(CNC(=O)c2c(Cl)ccnc2OCC2CC2)c(F)c1F] | ++ | + |
| 180 | | + | + |
| 182 | | ++ | + |
| 183 | | ++ | ++ |
| 184 | | ++ | + |
| 185 | | + | + |
| 186 | | ++ | ++ |

TABLE 2-continued

| Compound no. | Structure | ALDH2 (mutant) | ALDH2 (wild-type) |
|---|---|---|---|
| 187 | 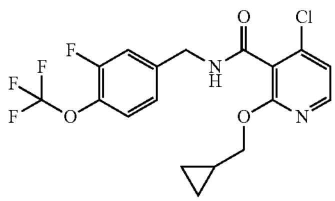 [SMILES: O=C(NCc1ccc(OC(F)(F)F)c(F)c1)c1c(Cl)ccnc1OCC1CC1] | ++ | + |
| 188 | 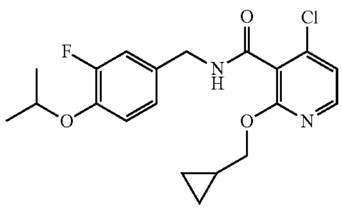 [SMILES: CC(C)Oc1ccc(CNC(=O)c2c(Cl)ccnc2OCC2CC2)cc1F] | − | − |
| 189 | 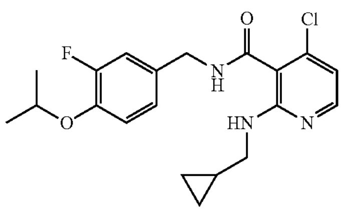 [SMILES: CC(C)Oc1ccc(CNC(=O)c2c(Cl)ccnc2NCC2CC2)cc1F] | + | − |
| 190 | 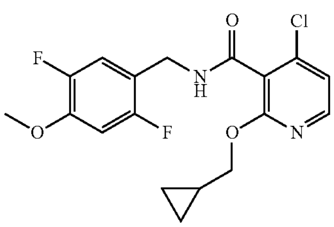 [SMILES: COc1cc(F)c(CNC(=O)c2c(Cl)ccnc2OCC2CC2)cc1F] | ++++ | ++++ |
| 191 | 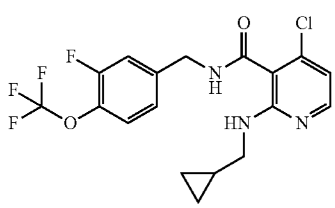 [SMILES: O=C(NCc1ccc(OC(F)(F)F)c(F)c1)c1c(Cl)ccnc1NCC1CC1] | + | + |
| 192 | 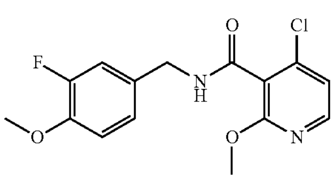 [SMILES: COc1ccc(CNC(=O)c2c(Cl)ccnc2OC)cc1F] | +++ | +++ |
| 193 | 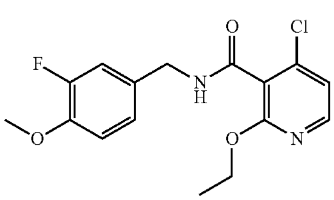 [SMILES: CCOc1nccc(Cl)c1C(=O)NCc1ccc(OC)c(F)c1] | ++ | ++ |
| 194 | | +++ | + |
| 195 | | ++ | ++ |
| 196 | | ++ | ++ |
| 197 | | ++++ | ++++ |
| 198 | | +++ | +++ |
| 199 | | ++ | ++ |
| 200 | | ++ | ++ |

TABLE 2-continued

| Compound no. | Structure | ALDH2 (mutant) | ALDH2 (wild-type) |
|---|---|---|---|
| 201 | 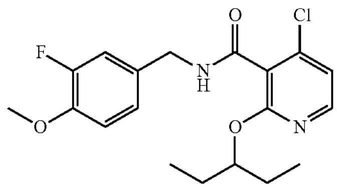 [SMILES: CCC(CC)Oc1nccc(Cl)c1C(=O)NCc1ccc(OC)c(F)c1] | ++ | ++ |
| 202 | 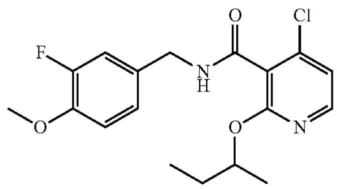 [SMILES: CCC(C)Oc1nccc(Cl)c1C(=O)NCc1ccc(OC)c(F)c1] | + | ++ |
| 203 | 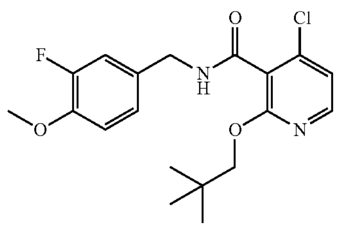 [SMILES: COc1ccc(CNC(=O)c2c(Cl)ccnc2OCC(C)(C)C)cc1F] | ++ | ++ |
| 204 | 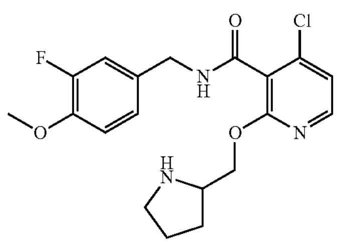 | + | + |
| 205 | 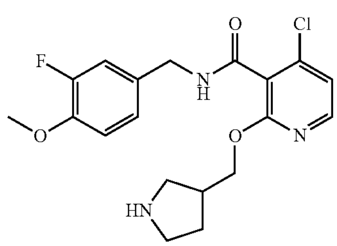 | + | + |
| 206 | 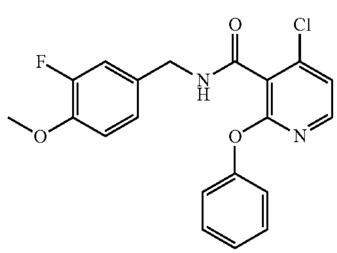 | + | ++ |
| 207 | 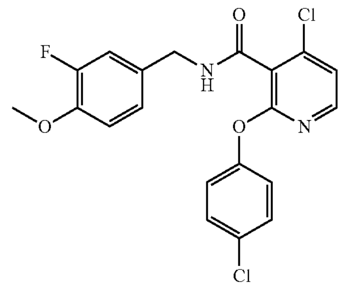 [SMILES: COc1ccc(CNC(=O)c2c(Cl)ccnc2Oc2ccc(Cl)cc2)cc1F] | + | ++ |
| 213 | 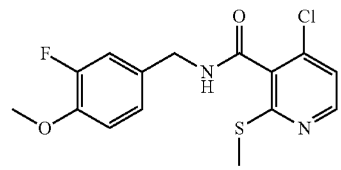 | ++ | ++ |
| 214 | 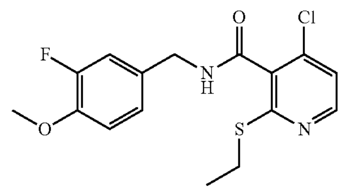 | ++ | ++ |
| 215 | 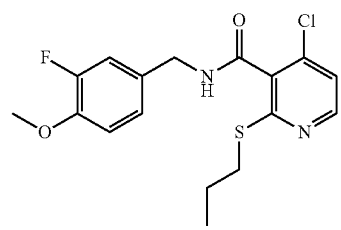 | +++ | ++++ |
| 216 | 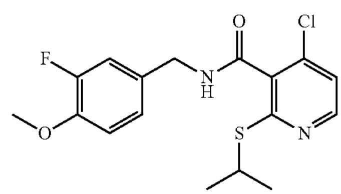 [SMILES: COc1ccc(CNC(=O)c2c(Cl)ccnc2SC(C)C)cc1F] | + | + |
| 217 | 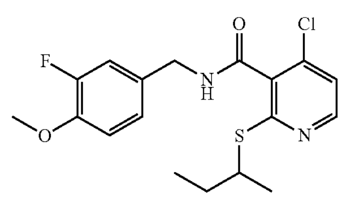 | ++ | + |
| 218 | 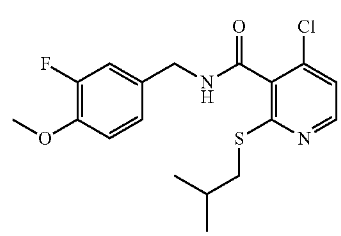 | + | + |

TABLE 2-continued

| Compound no. | Structure | ALDH2 (mutant) | ALDH2 (wild-type) |
|---|---|---|---|
| 219 | 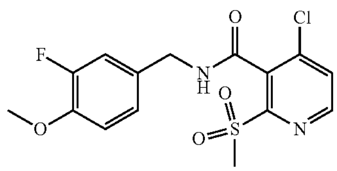 [SMILES: COc1ccc(CNC(=O)c2c(Cl)ccnc2S(C)(=O)=O)cc1F] | + | + |
| 220 | 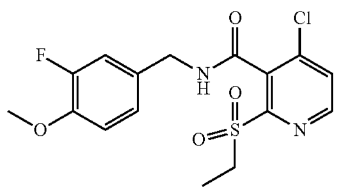 [SMILES: CCS(=O)(=O)c1nccc(Cl)c1C(=O)NCc1ccc(OC)c(F)c1] | + | + |
| 221 | 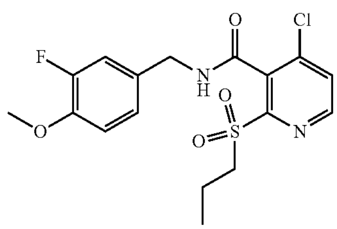 [SMILES: CCCS(=O)(=O)c1nccc(Cl)c1C(=O)NCc1ccc(OC)c(F)c1] | + | + |
| 222 | 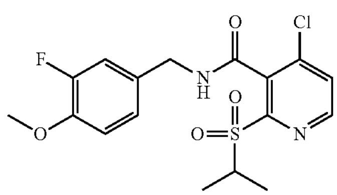 [SMILES: COc1ccc(CNC(=O)c2c(Cl)ccnc2S(=O)(=O)C(C)C)cc1F] | + | + |
| 223 | 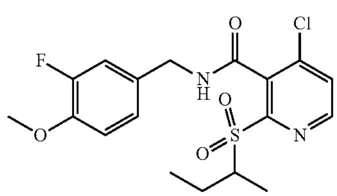 [SMILES: CCC(C)S(=O)(=O)c1nccc(Cl)c1C(=O)NCc1ccc(OC)c(F)c1] | + | + |
| 224 | 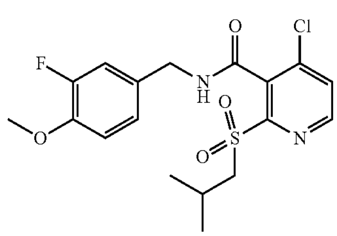 [SMILES: COc1ccc(CNC(=O)c2c(Cl)ccnc2S(=O)(=O)CC(C)C)cc1F] | + | + |
| 225 | 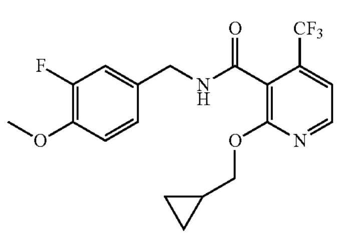 [SMILES: COc1ccc(CNC(=O)c2c(C(F)(F)F)ccnc2OCC2CC2)cc1F] | + | + |
| 226 | | + | + |
| 227 | | + | + |
| 228 | | + | + |
| 229 | | + | + |
| 230 | | + | + |
| 231 | | ++ | + |
| 232 | | + | + |

TABLE 2-continued

| Compound no. | Structure | ALDH2 (mutant) | ALDH2 (wild-type) |
|---|---|---|---|
| 233 | 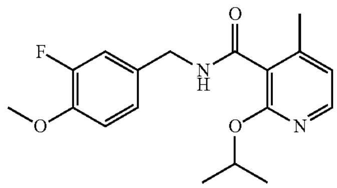 [SMILES: COc1ccc(CNC(=O)c2c(C)ccnc2OC(C)C)cc1F] | + | + |
| 234 | 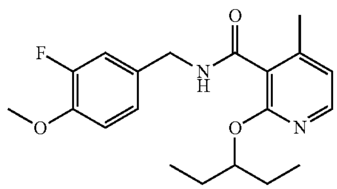 [SMILES: CCC(CC)Oc1nccc(C)c1C(=O)NCc1ccc(OC)c(F)c1] | + | + |
| 235 | 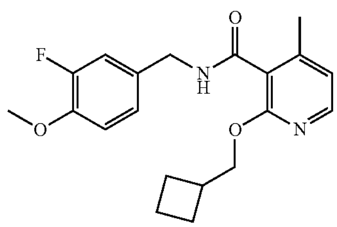 [SMILES: COc1ccc(CNC(=O)c2c(C)ccnc2OCC2CCC2)cc1F] | + | + |
| 236 | 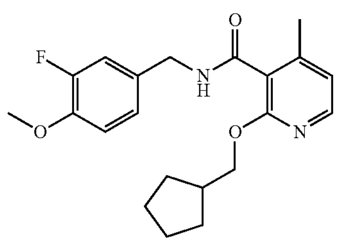 [SMILES: COc1ccc(CNC(=O)c2c(C)ccnc2OCC2CCCC2)cc1F] | + | + |
| 237 | 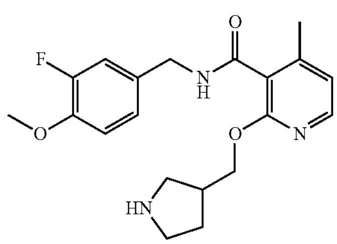 [SMILES: COc1ccc(CNC(=O)c2c(C)ccnc2OCC2CCNC2)cc1F] | + | + |
| 238 | 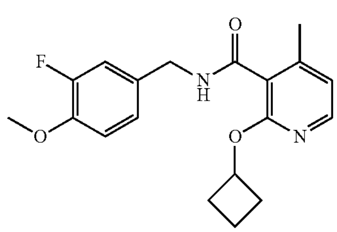 [SMILES: COc1ccc(CNC(=O)c2c(C)ccnc2OC2CCC2)cc1F] | + | + |
| 239 | 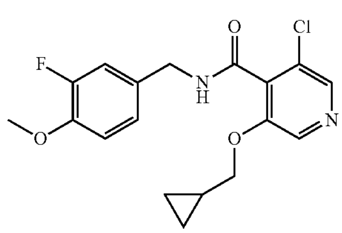 [SMILES: COc1ccc(CNC(=O)c2c(Cl)cncc2OCC2CC2)cc1F] | +++ | ++ |
| 240 | | ++ | + |
| 241 | | +++ | +++ |
| 242 | | ++ | ++ |
| 244 | | + | ++ |
| 245 | | +++ | + |
| 246 | | ++ | + |

TABLE 2-continued

| Compound no. | Structure | ALDH2 (mutant) | ALDH2 (wild-type) |
|---|---|---|---|
| 247 | 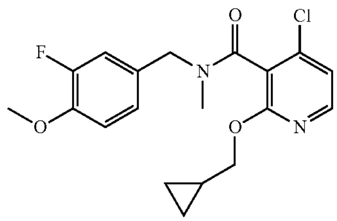 [SMILES: COc1ccc(CN(C)C(=O)c2c(Cl)ccnc2OCC2CC2)cc1F] | − | − |
| 248 | 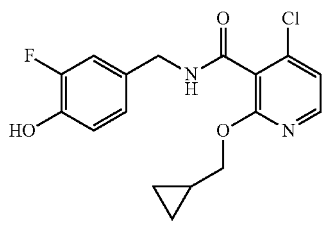 [SMILES: O=C(NCc1ccc(O)c(F)c1)c1c(Cl)ccnc1OCC1CC1] | − | − |
| 249 | 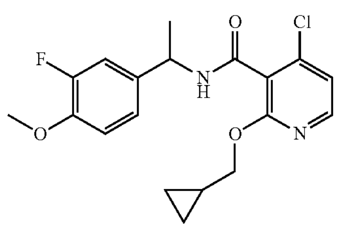 [SMILES: COc1ccc(C(C)NC(=O)c2c(Cl)ccnc2OCC2CC2)cc1F] | + | + |
| 250 | 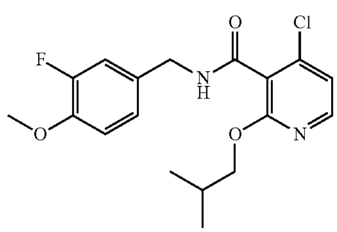 | + | + |
| 251 | 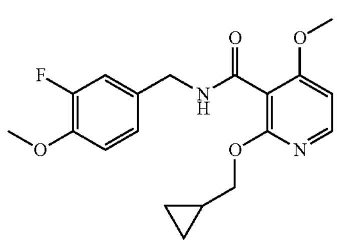 | + | + |
| 252 | 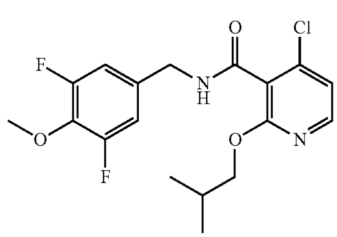 [SMILES: COc1c(F)cc(CNC(=O)c2c(Cl)ccnc2OCC(C)C)cc1F] | + | + |
| 253 | | + | + |
| 254 | | + | + |
| 255 | | + | + |
| 256 | | + | + |
| 257 | | + | + |
| 258 | | − | + |

TABLE 2-continued

| Compound no. | Structure | ALDH2 (mutant) | ALDH2 (wild-type) |
|---|---|---|---|
| 259 | 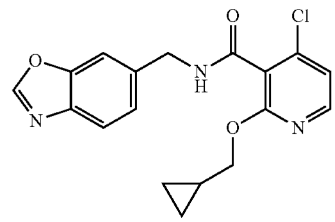 [SMILES: O=C(NCc1ccc2ncoc2c1)c1c(Cl)ccnc1OCC1CC1] | + | + |
| 260 | 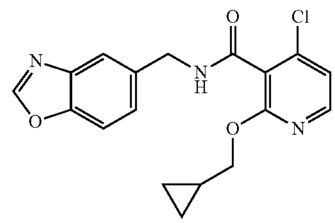 [SMILES: O=C(NCc1ccc2ocnc2c1)c1c(Cl)ccnc1OCC1CC1] | − | + |
| 261 | 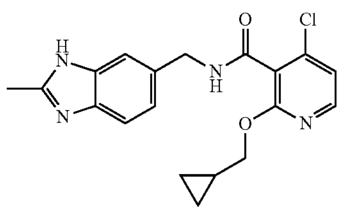 [SMILES: Cc1nc2ccc(CNC(=O)c3c(Cl)ccnc3OCC3CC3)cc2[nH]1] | + | + |
| 264 | 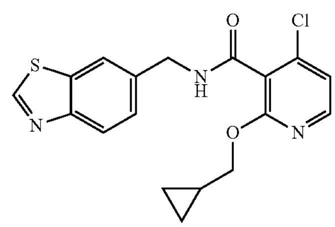 [SMILES: O=C(NCc1ccc2ncsc2c1)c1c(Cl)ccnc1OCC1CC1] | − | − |
| 269 | 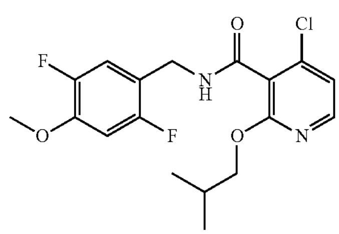 [SMILES: COc1cc(F)c(CNC(=O)c2c(Cl)ccnc2OCC(C)C)cc1F] | ++++ | ++++ |
| 273 | 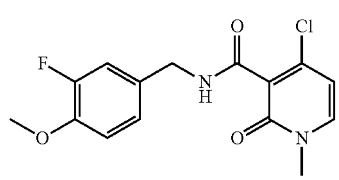 [SMILES: COc1ccc(CNC(=O)c2c(Cl)ccn(C)c2=O)cc1F] | + | + |

Example 3: Effect of Substrate (Acetaldehyde) Concentration on Mouse Liver Extract (Secondary Assay)

Compounds of the present disclosure were tested to determine their effect on physiological acetaldehyde substrate concentration. Concentration of 10 mM of acetaldehyde was previously tested, but this concentration is well above physiological concentration. Concentration 1 mM of acetaldehyde was chosen as it reflects a concentration that is closer to human after ethanol consumption.

The mitochondria fraction of fresh wild type mouse liver sample was isolated. Rodent liver mitochondria fraction was isolated based on published method as described in Hoppel et al. (1979) J Biol Chem. 254(10):4164. The final mitochondrial pellets were resuspended in a buffer containing 0.1 M Tris HCl 8.0, 10 mM dithiothreitol, 20% glycerol and 0.5% Triton-X. 10 mM, 1 mM, or 0.5 mM acetaldehyde was assayed in 250 µg of total protein. 20 µM of a compound of the present disclosure was tested along with control 1. Control 1 is:

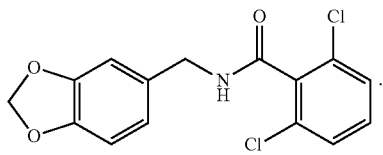 [SMILES: O=C(NCc1ccc2c(c1)OCO2)c1c(Cl)cccc1Cl]

Figure 2:
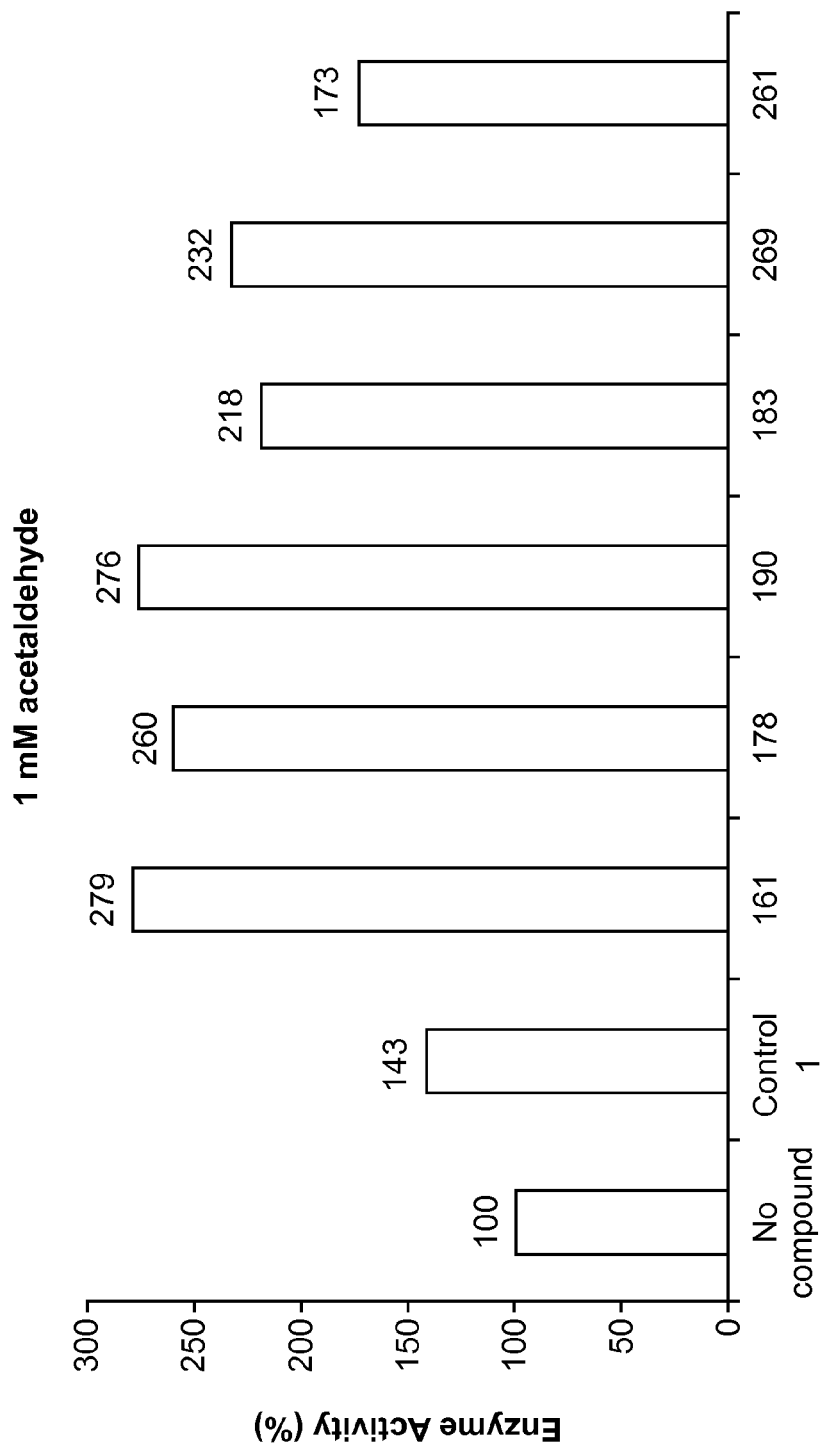
FIG. 2 is a graph showing the enzymatic activity (%) for compounds of the present disclosure tested in 1 mM acetaldehyde assay.
Figure 3:
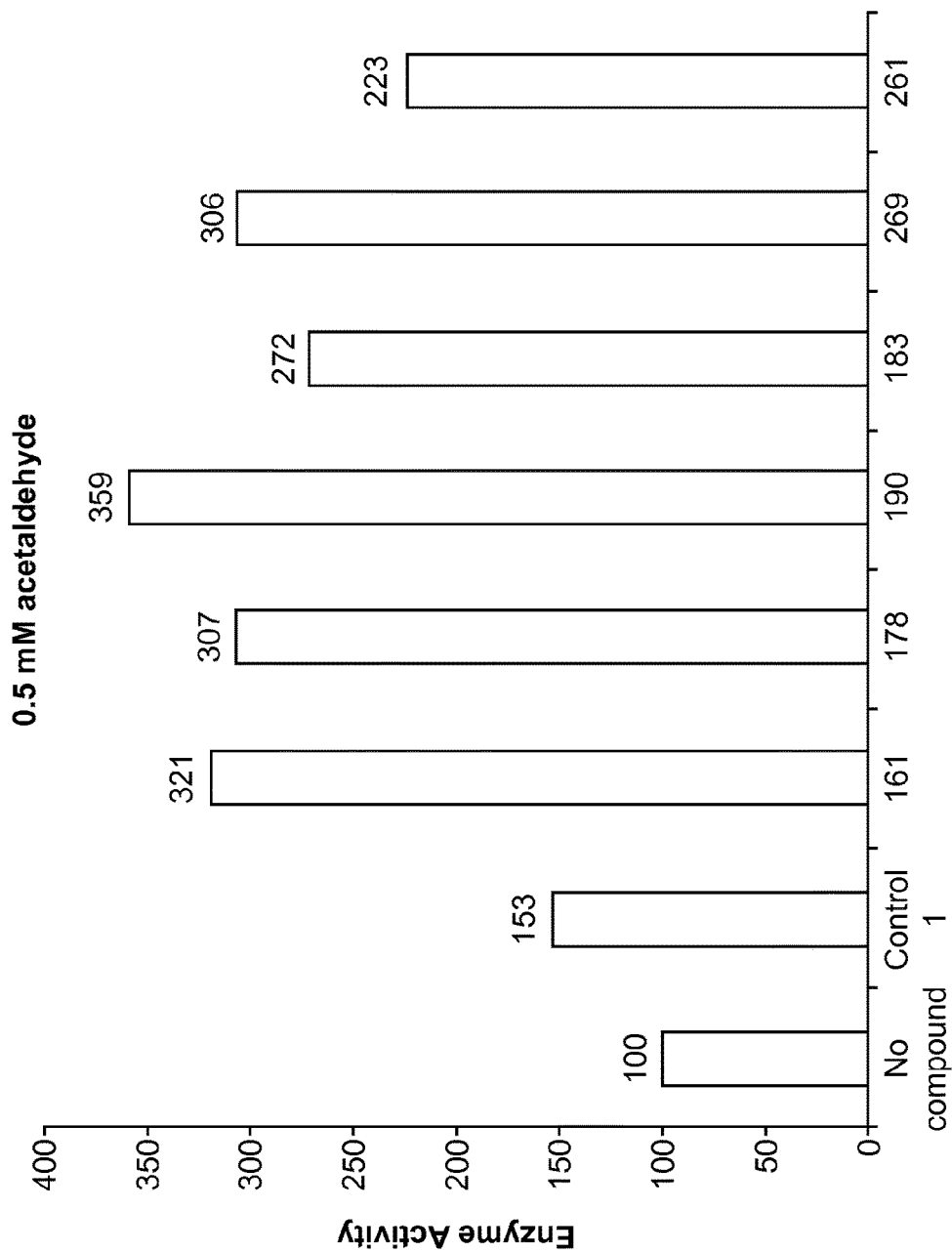
FIG. 3 is a graph showing the enzymatic activity (%) for compounds tested in 0.5 mM acetaldehyde assay.
Figure 4:
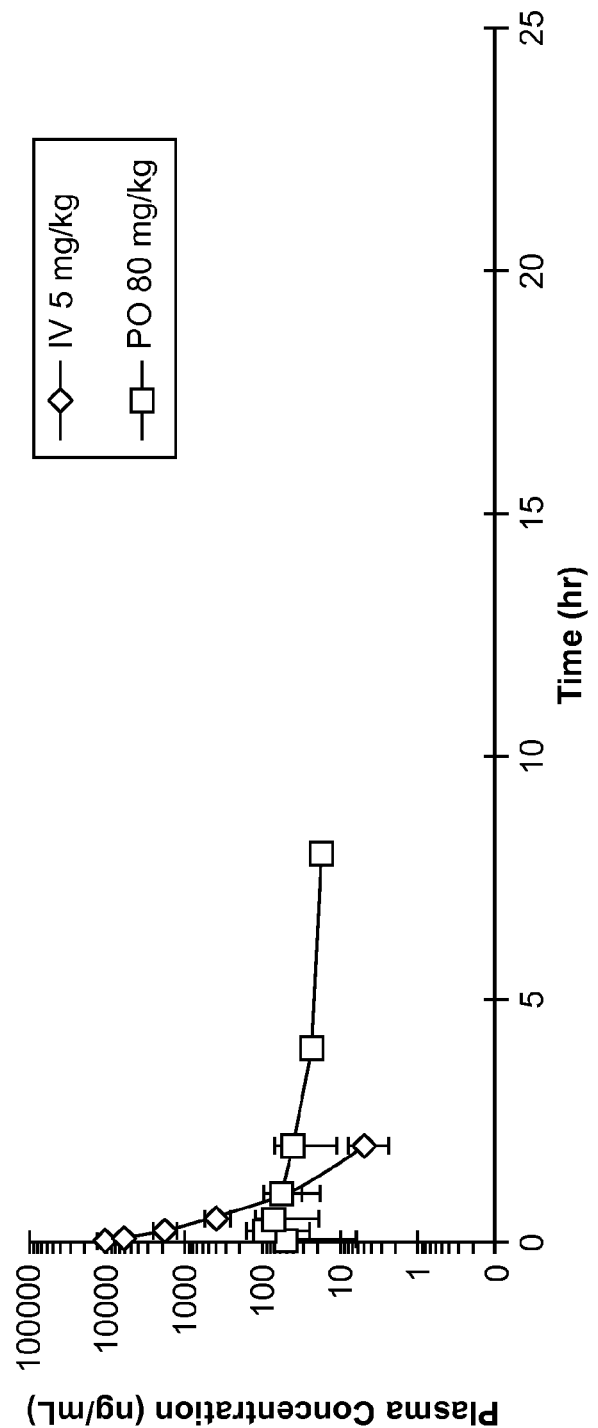
FIG. 4 is a graph showing the plasma concentration (ng/mL) over time for intravenous (IV) or oral (PO) administration to rats.
Figure 5:
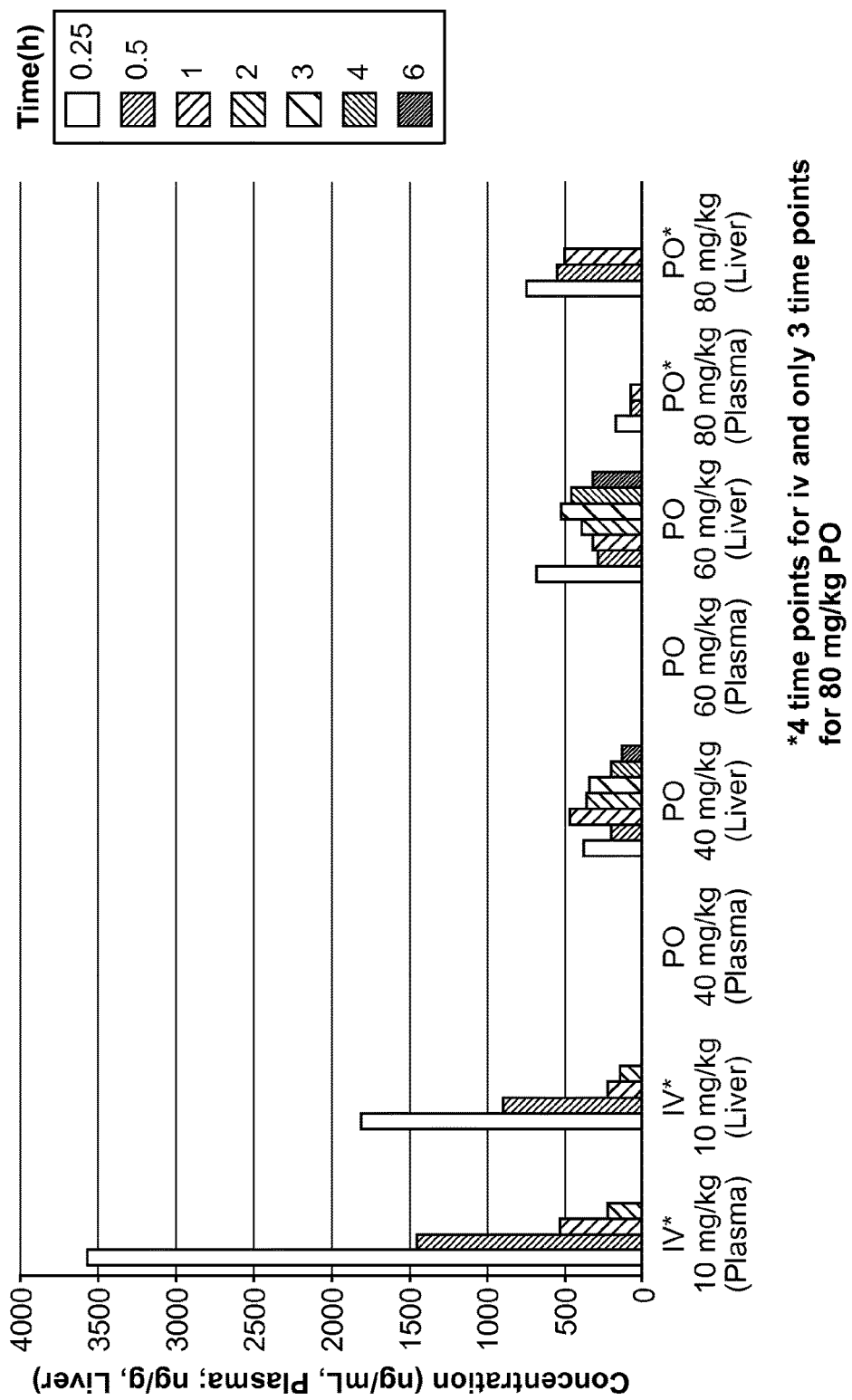
FIG. 5 is a graph showing the concentration of plasma (ng/mL) and concentration of liver (ng/g) for IV or PO administration.

Results are shown in FIGS. 1-3. FIG. 1 is a graph showing the enzymatic activity (%) for compounds of the present disclosure tested in 10 mM acetaldehyde assay. FIG. 2 is a graph showing the enzymatic activity (%) for compounds of the present disclosure tested in 1 mM acetaldehyde assay. FIG. 3 is a graph showing the enzymatic activity (%) for compounds tested in 0.5 mM acetaldehyde assay. The data revealed that the compounds of the present disclosure are potent under physiologically relevant acetaldehyde concentration.

Example 4: ADMET (Absorption, Distribution, Metabolism, and Excretion Toxicity)

In vitro ADMET of compounds of the present disclosure was carried out according to known methods in the art. Below are data for certain compounds of the present disclosure.

| Compound no. | Aqu. Solu. (µg/mL) | CLogP | LogD (pH 7.4) | HLM $T_{1/2}$ (min) | RLM $T_{1/2}$ (min) | MLM $T_{1/2}$ (min) | NHPLM $T_{1/2}$ (min) |
|---|---|---|---|---|---|---|---|
| Control 1 | 12 | 2.83 | 3.4 | 21.2 | 1.33 | 0.753 | 1.57 |
| 135 | 5 | 3.95 | 3.8 | 2.67 | 0.753 | 0.753 | 0.685 |

| 161 | 28 | 3.72 | 3.0 | 12.4 | 0.974 | 2.08 | 2.54 |
| 169 | 272 | 1.85 | 1.6 | 3.85 | 82.5 | 100 | 51.3 |

| Compound no | Plasma stability Human Rat | Cyp Inhibition (%, 10 μM) | | | | | Caco-2 Papp (×10⁻⁶ m/s) | | | PPB (%) Human Rat |
|---|---|---|---|---|---|---|---|---|---|---|
| | | 3A4 | 2C9 | 2C19 | 2D6 | 1A2 | A-B | B-A | B-A/A-B | |
| Control 1 | 100 100 | 83.5 | 16.3 | 72.4 | 9.1 | 31.9 | 16.6 | 11.7 | 0.70 | 97.5 96.3 |
| 161 | 100 100 | 14.9 | 5.7 | 15.9 | 6.4 | 35.2 | 15.7 | 10.7 | 0.68 | 99.3 96.1 |
| 169 | 100 100 | 7.7 | −12.0 | 3.5 | 0.81 | 1.1 | 1.22 | 13.1 | 10.7 | 90.2 63.3 |

In vitro ADMET of compound 161 is follows: the absorption (Caco-2, Papp, A-B) is 15.7×10⁻⁶ cm/s and B-A/A-B ratio is 0.68; the metabolism (HLM $t_{1/2}$) is 12.4 min; the Cyp inhibition (10 mM) is 3A4(15%), 2C9(6%), 2C19(16%), 2D6(6%), and 1A2(35%); the hERG channel (patch-clamp) $IC_{50}$ is greater than 30 μM; the protein binding is 99.3%; and the plasma stability (human, 5 h) is 100%.

Example 5: Behavior Observation of Mouse Pharmacodynamics (PD) Study for Compound 161

Figure 6:
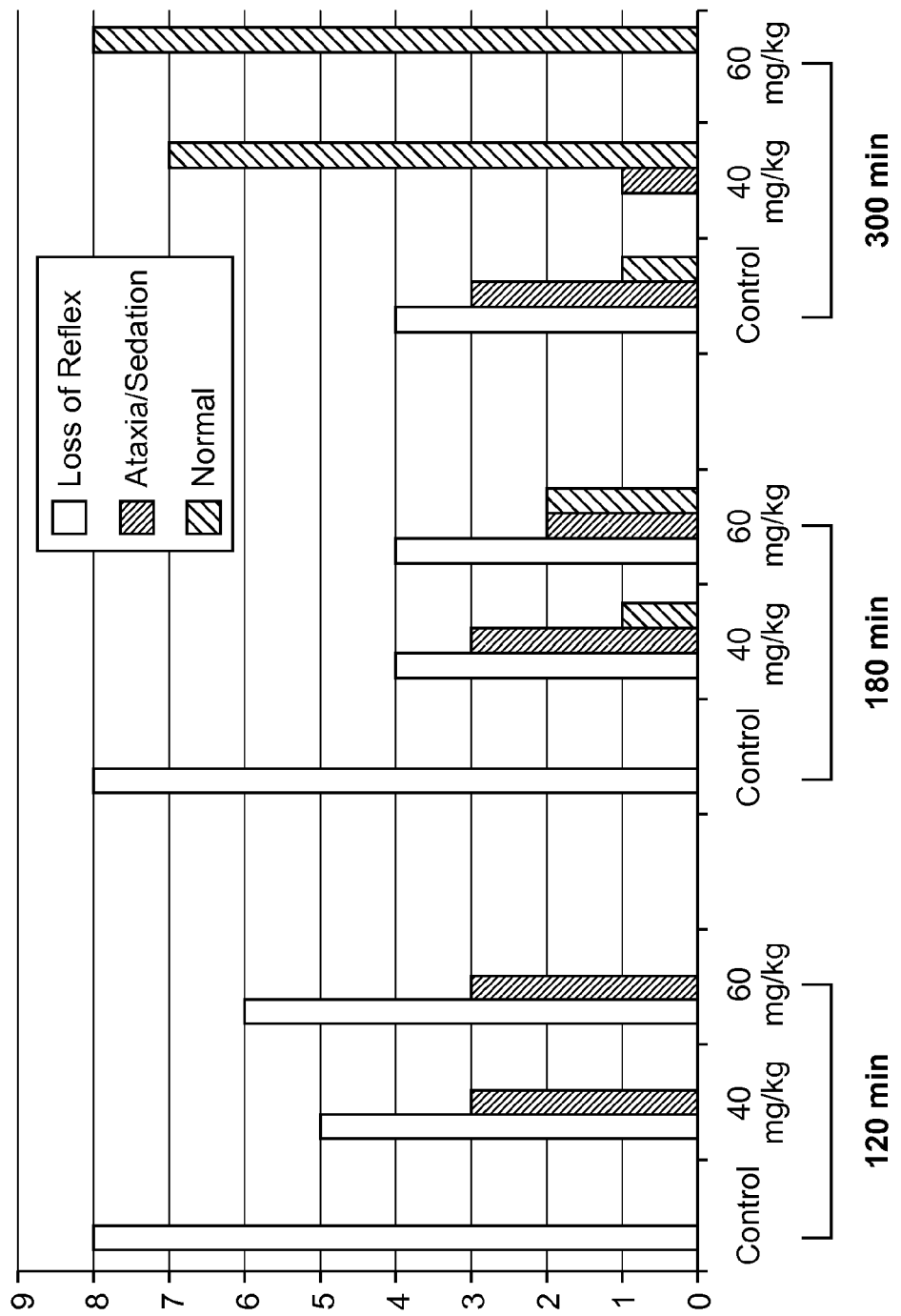
FIG. 6 is a graph showing the behavior of mice at 120 min, 180 min, and 300 min.
Figure 7:
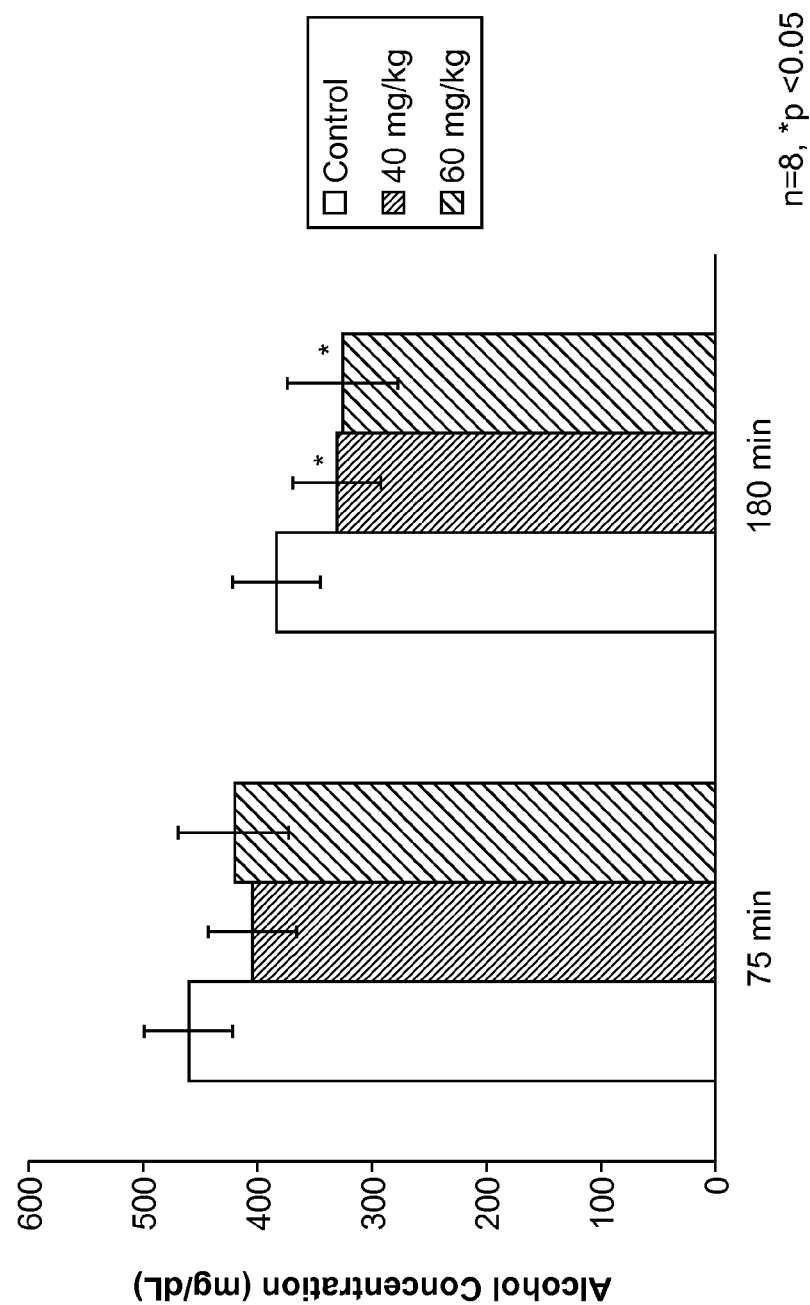
FIG. 7 is a graph showing the alcohol concentration (mg/dL) at 75 min and 180 min.

Mice (male C57BL6 (8 to 9 weeks, 20-22 g)) were treated with PO 5/kg of EtOH. Then PO 40 mg/kg or 60 mg/kg compound 161 were administered to the mice. The mice treated with compound 161 demonstrated significant PD response. Compound 161 reduces blood alcohol levels in mice treated with PO 5 g/kg of EtOH. FIG. 6 is a graph showing the behavior of mice at 120 min, 180 min, and 300 min. FIG. 7 is a graph showing the alcohol concentration (mg/dL) at 75 min and 180 min.

Figure 8:
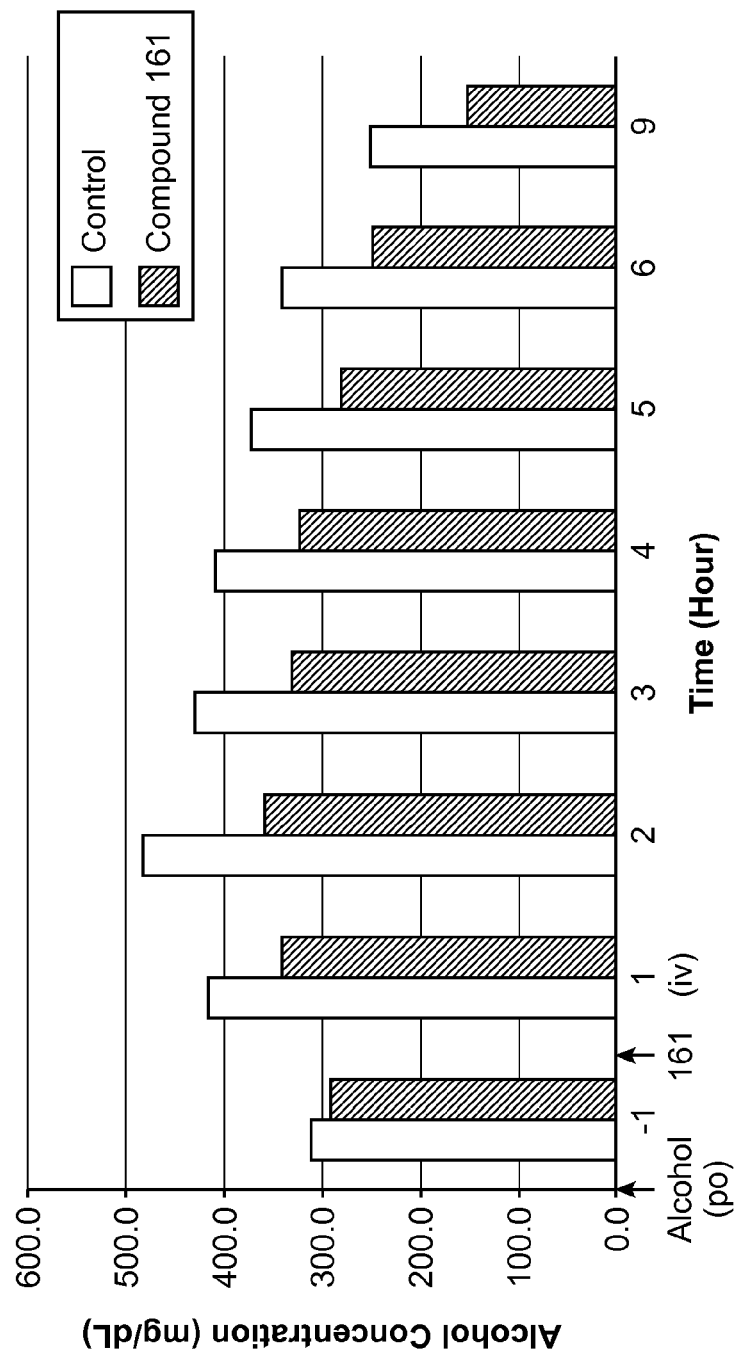
FIG. 8 is a graph showing the alcohol concentration (mg/dL) versus time (hr).

A PD study of IV administration of compound 161 was also carried out. The mice were treated with PO 5 g/kg of alcohol and were then treated with 10 mg/kg of compound 161 administered through IV. Results show that compound 161 treatment reduces blood alcohol levels in mice. FIG. 8 is a graph showing the blood alcohol concentration (mg/dL) versus time (hr).

Example 6: Compound 161 on the Rate of 4-HNE Oxidation by ALDH-2

The effect of compound 161 on the rate of 4-HNE oxidation by ALDH-2 was carried out by methods known in the art. To each well of a 96-well flat bottom UV plate, the following reagents were sequentially added by pipetting:
50 μl of 100 mM sodium pyrophosphate decahydrate (NaPPi, pH 8.4)
25 μl of 10 mM nicotinamide adenine dinucleotide hydrate (NAD)
22 μl of water
1 μl of 20 mM testing compound DMSO solution The plate was then put on a shaker to mix the cocktails in wells. After 5 minutes of mixing, 1 ul of ALDH-2 (or mutant) enzyme was added to each well with the reagent cocktail. DMSO was used as blank control in the plate. The plate was again put on shaker for another 5 minutes of shaking to enhance bonding between testing compounds and the enzyme.

1 ul of 30 mM 4-HNE in water was then added to each of wells containing the above reaction mixture. After a short vigorous mixing, the UV plate was fed into a plate reader to measure kinetic optical density (O.D.) at wavelength 340 nm at 25° C. over 4 minutes. Each point of measurement was taken at a time interval of 40 seconds.

Figure 9:
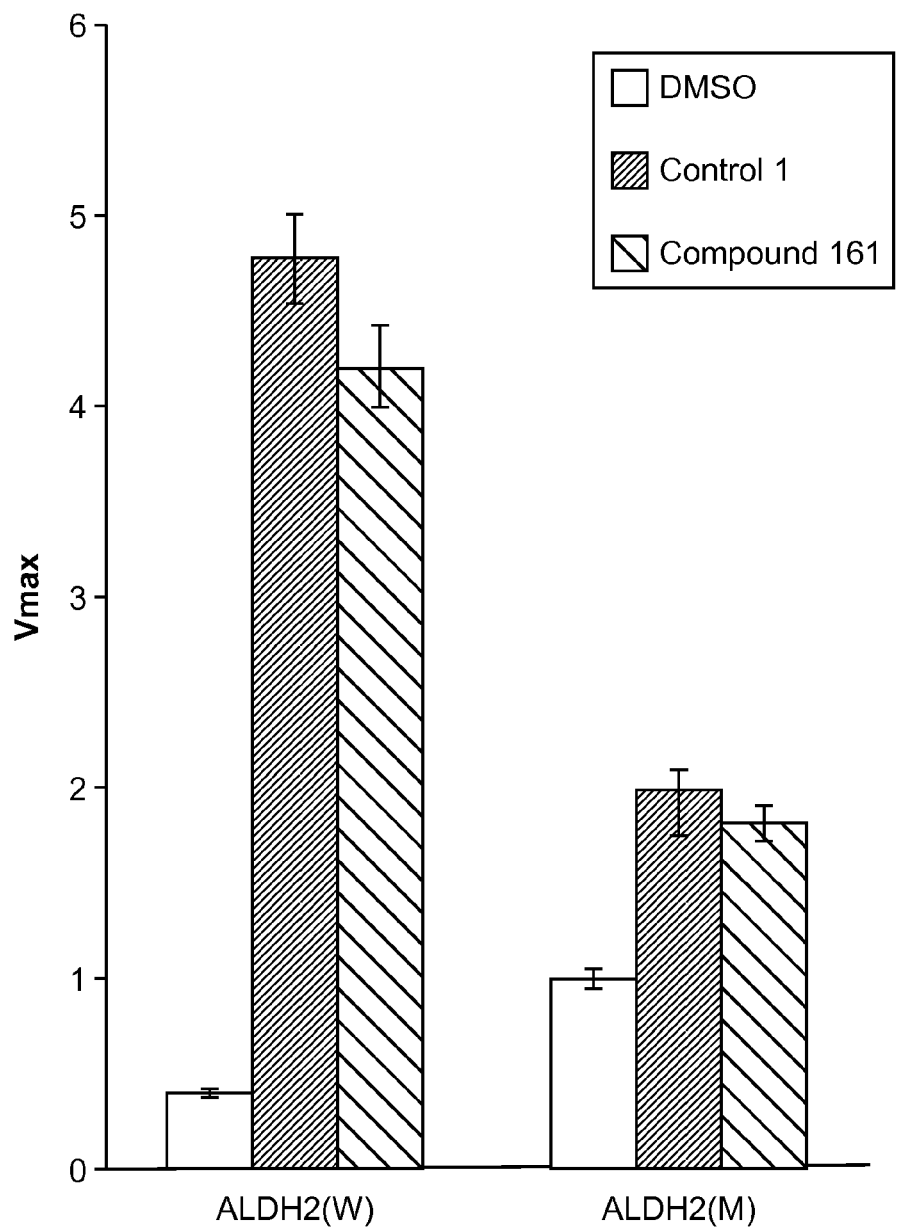
FIG. 9 is a graph showing the V max for ALDH2 (wild type, W) and ALDH2 (mutant, M).
Figure 10:
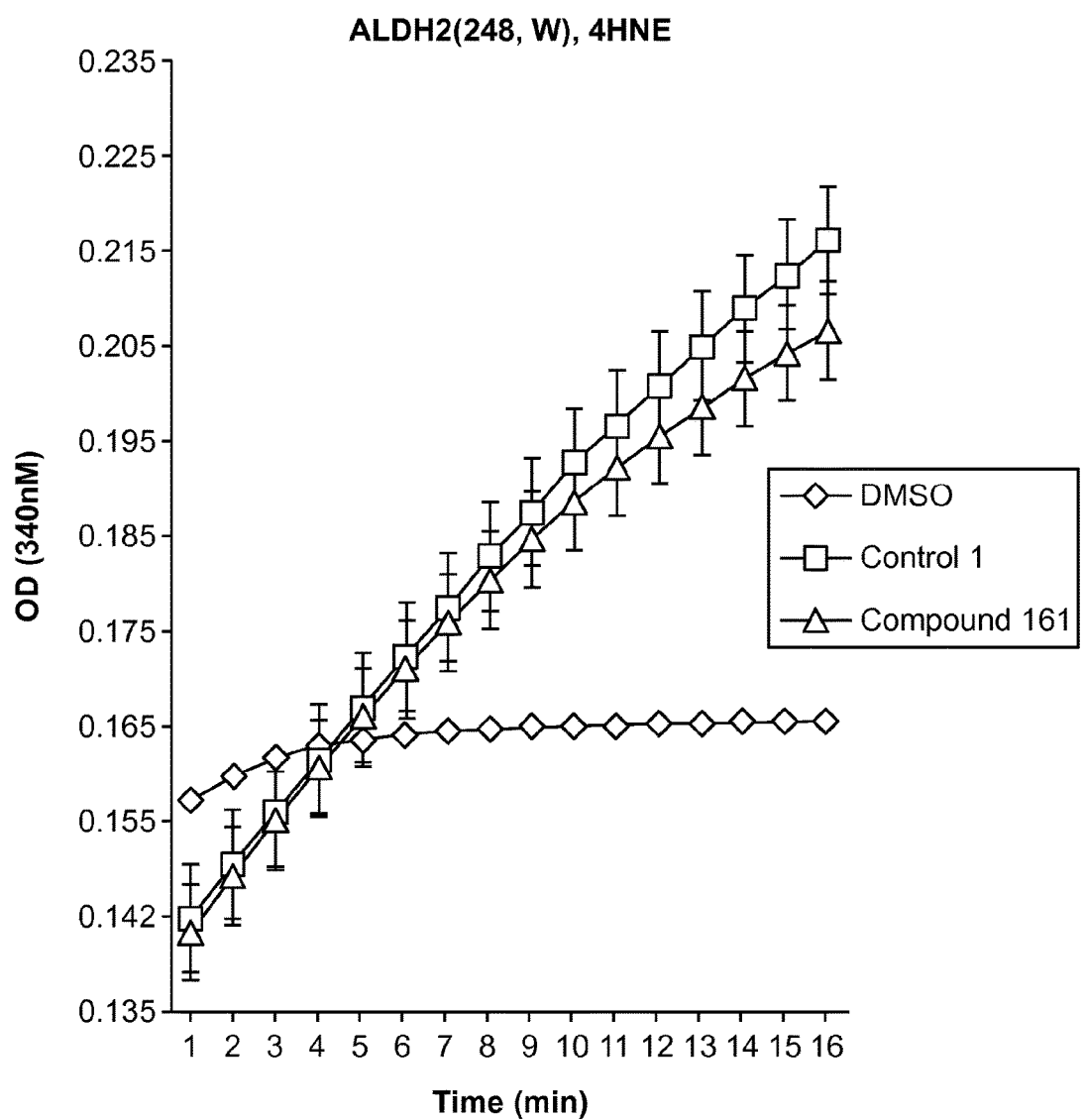
FIG. 10 is a graph showing the optical density (OD) (340 nM) versus time.

The results show that compound 161 accelerate the rate of 4-HNE oxidation by ALDH-2. FIG. 9 is a graph showing the V max for ALDH2 (wild type, W) and ALDH2 (mutant, M). FIG. 10 is a graph showing the optical density (340 nM) versus time.

Example 7: ALDH Activity in Human Liver Biopsy Samples

The study of compounds of the present disclosure on unpurified human liver homogenates was carried out according to methods known in the art. Briefly, 750 jug of the total unpurified protein from the liver mitochondria fraction was used in this assay. The kinetic increase of absorbance at λ340 nm was monitored for 15 minutes for NADH. For the first 3 minutes, the assay was carried in the absence of the substrate or AD-363 to establish the base line. As expected, no NADH production was detected. Substrate acetaldehyde was then added at the 3-min time point and the reaction monitored for the next 6 min to record the catalytic rate in the absence of an activator. Compound 161 (20 μM), was then added at the 9-min time point and the reaction monitored for the next 6 min to record the increase in catalytic rate.

Figure 11:
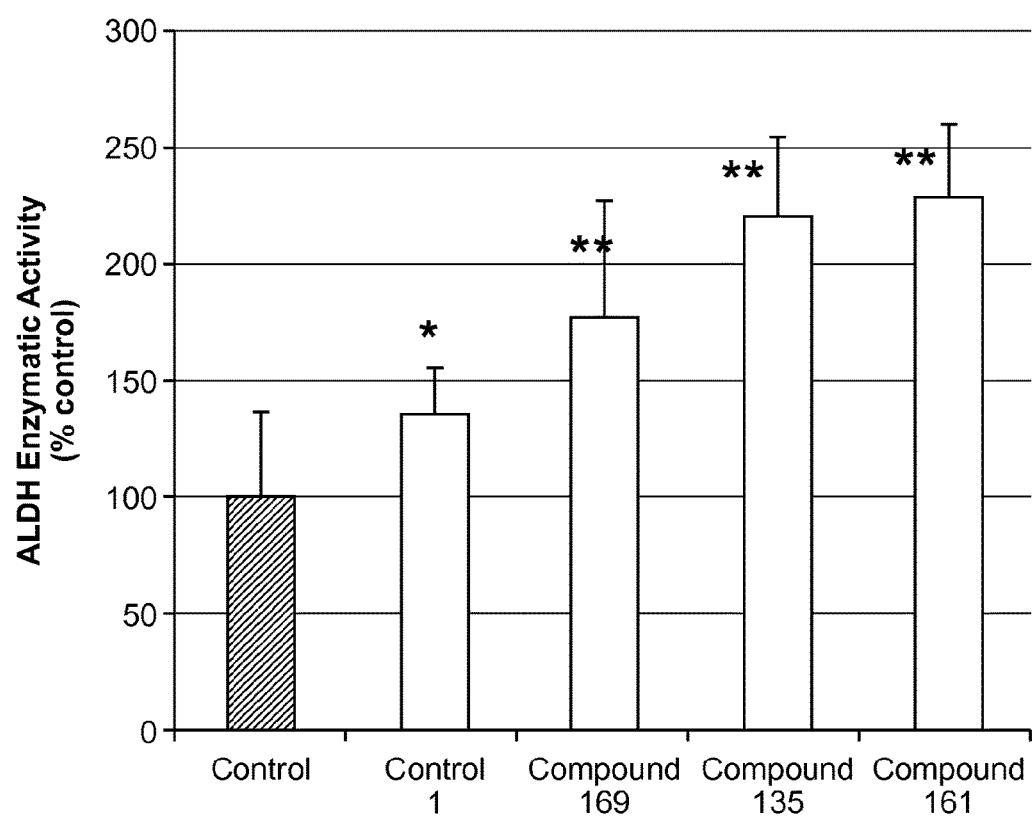
FIG. 11 is a graph showing the effect of compounds of the present disclosure on unpurified human liver homogenates (n=5).
Figure 12:
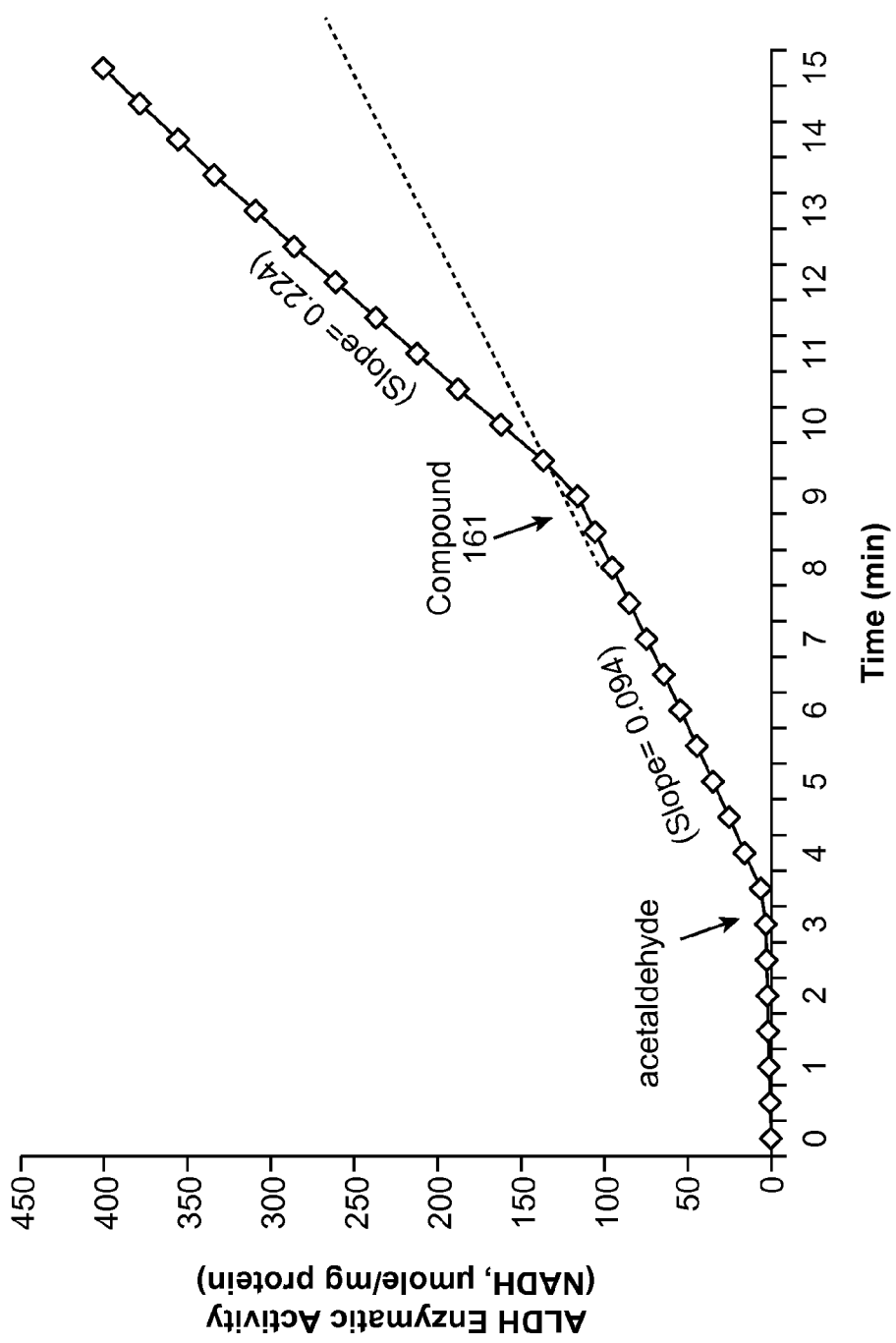
FIG. 12 is a graph showing the ALDH enzymatic activity (NADH, μmole/mg protein) versus time for compound 161.

The results show that compounds of the present disclosure increase ALDH activity in human liver samples. Compound 161 increases human liver enzyme's catalytic rate is increased by 2.38 folds. FIG. 11 is a graph showing the effect of compounds of the present disclosure on unpurified human liver homogenates (n=5). Control is the sample without any treatment. FIG. 12 is a graph showing the ALDH enzymatic activity (NADH, μmole/mg protein) versus time for compound 161.

What is claimed is:

1. A method of treating a disease or condition associated with ALDH2 modulation, the method comprising:
   administering to a subject in need thereof an effective amount of a compound of formula:

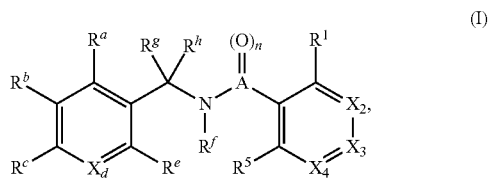

(I)

or a pharmaceutically acceptable salt or solvate thereof, wherein
A is C;
$X_2$ is $CR^2$;

X₃ is CR³;
X₄ is selected from N and NO;
X_d is CR^d;
R^a, R^b, R^d, and R^e are independently selected from hydrogen, halogen, OH, $C_1$-$C_6$ alkyl, and $C_1$-$C_6$ alkoxy
R^c is selected from OH, $C_1$-$C_6$ alkoxy, $OCF_3$, $OCF_2H$, and $OCFH_2$;
R^f, R^g, and R^h are independently selected from hydrogen and $C_1$-$C_6$ alkyl;
R¹ is halogen;
R² and R³ are independently selected from hydrogen, halogen, OH, $C_1$-$C_6$ alkyl, $C_1$-$C_6$ alkoxy, OR⁷, $NH_2$, $NO_2$, NHR⁷, NR⁷R⁷, $S(O)_q R^7$, C(O)R⁷, C(O)OR⁷, $CF_3$, $CF_2H$, $CFH_2$, $OCF_3$, $OCF_2H$, and $OCFH_2$;
R⁵ is selected from halogen, $C_1$-$C_6$ alkyl, OR⁷, and NHR⁷;
R⁶ is selected from hydrogen and $C_1$-$C_6$ alkyl;
R⁷ is selected from (a) hydrogen, (b) $C_1$-$C_6$ alkyl, (c) $C_2$-$C_6$ alkenyl, (d) $C_2$-$C_6$ alkynyl, (e) 3-14 membered saturated, partially saturated, or unsaturated carbocycle, and (f) 3-14 membered saturated, partially saturated, or unsaturated heterocycle containing one or more heteroatoms selected from N, O, and S;
wherein (b)-(f) optionally is substituted with one or more R⁸;
R⁸ is selected from (a) halogen, (b) OH, (c) $NO_2$, (c) $NH_2$, (d) C(O)OH, (e) NH($C_1$-$C_6$ alkyl), (f) N($C_1$-$C_6$ alkyl)2, (g) C(O)O—($C_1$-$C_6$ alkyl), (h) $C_1$-$C_6$ alkyl, (i) $C_1$-$C_6$ alkoxy, (j) 3-14 membered saturated, partially saturated, or unsaturated carbocycle, (k) 3-14 membered saturated, partially saturated, or unsaturated heterocycle containing one or more heteroatoms selected from N, O, and S; and (l) =O
wherein (e)-(k) optionally is substituted with one or more R⁹;
R⁹ is selected from halogen, OH, $C_1$-$C_6$ alkyl, $C_1$-$C_6$ alkoxy, C(O)OH, $NH_2$, NH($C_1$-$C_6$ alkyl), N($C_1$-$C_6$ alkyl)₂, $NO_2$, and $S(O)_q$—($C_1$-$C_6$ alkyl);
n is 1;
p is 1 or 2; and
q is 0, 1, or 2,
wherein the disease or condition associated with ALDH2 modulation is alcohol intolerance, alcohol addiction, an alcohol abuse disorder, alcohol intoxication, alcohol dependence, alcohol poisoning, or symptoms of alcohol consumption in the subject.

2. The method of claim 1, wherein the alcohol poisoning is methanol poisoning.

3. The method of claim 2, wherein the alcohol poisoning is acute alcohol poisoning.

4. The method of claim 3, wherein the alcohol intoxication is acute alcohol intoxication.

5. The method of claim 1, wherein the symptom of alcohol consumption is a hangover symptom.

6. The method of claim 5, wherein the hangover symptom is selected from a group consisting of dehydration, fatigue, headache, body aches, vomiting, diarrhea, flatulence, weakness, elevated body temperature and heart rate, hypersalivation, difficulty concentrating, sweating, anxiety, dysphoria, irritability, sensitivity to light and noise, erratic motor function, trouble sleeping, severe hunger, halitosis, and lack of depth perception.

7. The method of claim 1, further comprising an opioid receptor antagonist.

8. The method of claim 7, wherein the opioid receptor antagonist is naltrexone.

9. The method of claim 1, wherein the administering is effective for sequestering aldehydes in a subject exposed to alcohol or aldehydes.

10. The method of claim 1, wherein the administering is effective for reducing a level of an aldehyde present at a toxic level in the subject to below the toxic level, wherein the aldehyde is a biogenic aldehyde or a xenogenic aldehyde.

11. The method of claim 10, wherein the aldehyde is a biogenic aldehyde selected from the group consisting of acetaldehyde, malondialdehyde (MDA), 3,4-dihydroxyphenylacetaldehyde (DOPAL), 3,4-dihydroxyphenylglycolaldehyde (DOPEGAL), hexanal, acrolein, glyoxal, crotonaldehyde, trans-2-nonenal, 4-oxo-2-nonenal, and 4-hydroxy-2-nonenal (HNE).

12. The method of claim 10, wherein the xenogenic aldehyde is an environmental aldehyde that is ingested or inhaled.

13. The method of claim 1, wherein the disease or condition associated with ALDH2 modulation is an acute or a chronic free-radical associated disease in the subject.

14. The method of claim 13, wherein the acute free-radical associated disease is selected from seizures and photo-damage to the skin.

15. The method of claim 1, wherein the disease or condition associated with ALDH2 modulation is an ocular disorder in the subject.

16. The method of claim 15, wherein the ocular disorder is selected from age-related cataracts, secondary cataracts, traumatic cataracts, congenital cataracts, age-related macular degeneration, and radiation cataracts.

17. The method of claim 1, wherein the disease or condition associated with ALDH2 modulation is radiation-induced damage to epithelial cells in the subject.

18. The method of claim 17, wherein the radiation-induced damage results in radiation dermatitis.

19. The method of claim 17, wherein the compound is to be administered before the subject is exposed to ionizing radiation.

20. The method of claim 17, wherein the compound is to be administered after the subject is exposed to ionizing radiation.

21. The method of claim 7, wherein the compound is to be administered both before and after the subject is exposed to ionizing radiation.

22. The method of claim 17, wherein the radiation-induced damage results in mucositis.

23. The method of claim 17, wherein the compound is to be administered to a mucosal surface in the subject.

24. The method of claim 1, wherein the administering is effective for reducing the likelihood that the subject will develop head and neck cancer.

25. The method of claim 24, wherein the subject is a habitual user of betel quid.

26. The method of claim 25, wherein the compound is formulated as a toothpaste, a tooth gel, a tooth powder, a mouth rinse, a chewing gum, or a lozenge.

27. The method of claim 1, wherein the administering is effective for reducing the likelihood that the subject will develop oral cancer or lung cancer.

28. The method of claim 1, wherein the compound is to be administered by a route selected from intramuscular, intravenous, subcutaneous, topical, and oral.

29. The method of claim 1, wherein the administering of the compound to the subject activates ALDH2 activity in the subject.

30. The method of claim 1, wherein the compound is of the formula IIa:

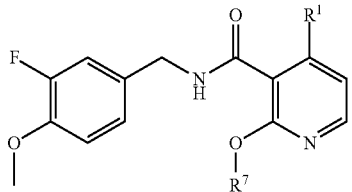

(IIa)

or a pharmaceutically acceptable salt or solvate thereof.

31. The method of claim 1, wherein the compound is of the formula IVa:

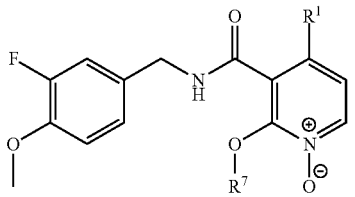

(IVa)

or a pharmaceutically acceptable salt or solvate thereof.

32. The method of claim 1, wherein the compound is of the formula IIb:

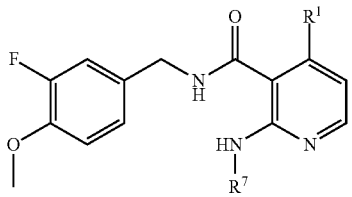

(IIb)

or a pharmaceutically acceptable salt or solvate thereof.

33. The method of claim 1, wherein the compound is of the formula IVb:

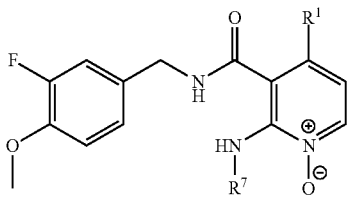

(IVb)

or a pharmaceutically acceptable salt or solvate thereof.

34. The method of claim 1, wherein the compound is of the formula IIc:

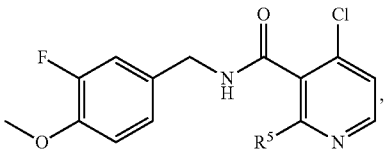

(IIc)

wherein:
$R^5$ is selected from halogen, $C_1$-$C_6$ alkyl, $OR^7$, and $NHR^7$,
$R^7$ is selected from $C_1$-$C_6$ alkyl optionally substituted with $R^8$,
$R^8$ is 3-14 membered saturated, partially saturated, or unsaturated carbocycle optionally substituted with $R^9$, and
$R^9$ is $C_1$-$C_6$ alkyl,
or a pharmaceutically acceptable salt or solvate thereof.

35. The method of claim 1, wherein the compound is of the formula IVc:

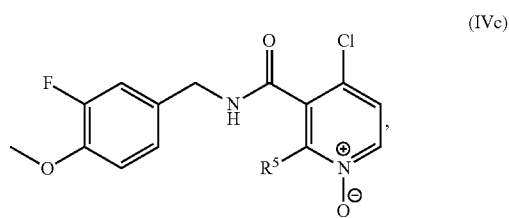

(IVc)

wherein:
$R^5$ is selected from halogen, $C_1$-$C_6$ alkyl, $OR^7$, and $NHR^7$,
$R^7$ is selected from $C_1$-$C_6$ alkyl optionally substituted with $R^8$,
$R^8$ is 3-14 membered saturated, partially saturated, or unsaturated carbocycle optionally substituted with $R^9$, and
$R^9$ is $C_1$-$C_6$ alkyl,
or a pharmaceutically acceptable salt or solvate thereof.

36. The method of claim 1, wherein the compound or a pharmaceutically acceptable salt or solvate thereof is selected from:

| Compound no. | Structure |
|---|---|
| 157 | ![structure] |
| 160 | ![structure] |
| 161 | ![structure] |

-continued

| Compound no. | Structure |
|---|---|
| 168 | 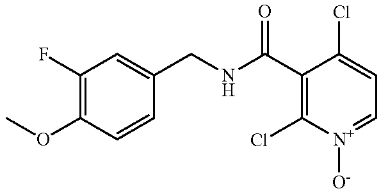 [SMILES: COc1ccc(CNC(=O)c2c(Cl)cc[n+]([O-])c2Cl)cc1F] |
| 169 | 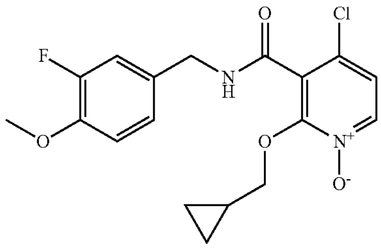 [SMILES: COc1ccc(CNC(=O)c2c(Cl)cc[n+]([O-])c2OCC2CC2)cc1F] |
| 173 | 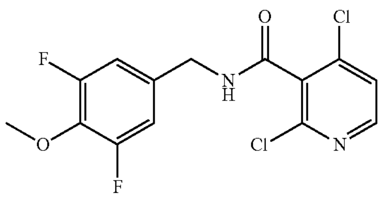 [SMILES: COc1c(F)cc(CNC(=O)c2c(Cl)ccnc2Cl)cc1F] |
| 174 | 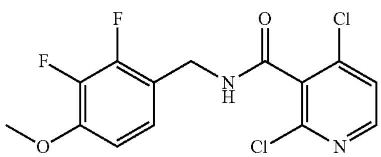 [SMILES: COc1ccc(CNC(=O)c2c(Cl)ccnc2Cl)c(F)c1F] |
| 175 | 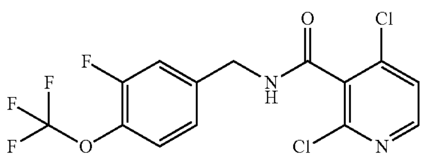 [SMILES: O=C(NCc1ccc(OC(F)(F)F)c(F)c1)c1c(Cl)ccnc1Cl] |
| 176 | 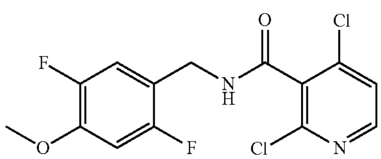 [SMILES: COc1cc(F)c(CNC(=O)c2c(Cl)ccnc2Cl)cc1F] |
| 177 | 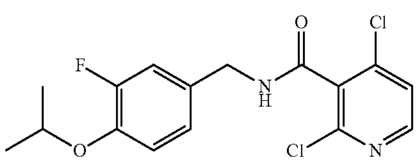 [SMILES: CC(C)Oc1ccc(CNC(=O)c2c(Cl)ccnc2Cl)cc1F] |
| 178 | 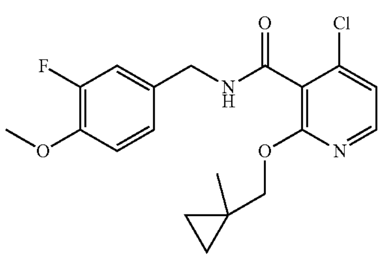 |

-continued

| Compound no. | Structure |
|---|---|
| 179 | 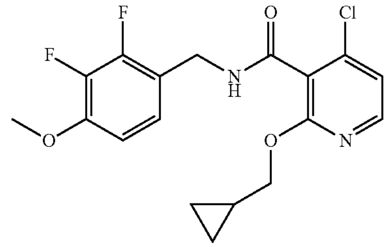 [SMILES: COc1ccc(CNC(=O)c2c(Cl)ccnc2OCC2CC2)c(F)c1F] |
| 181 | 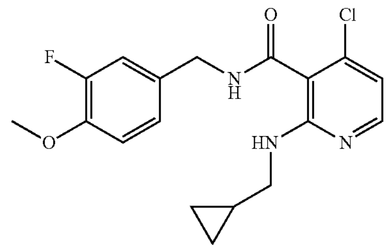 |
| 182 | 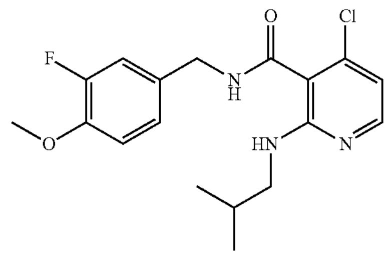 |
| 183 | 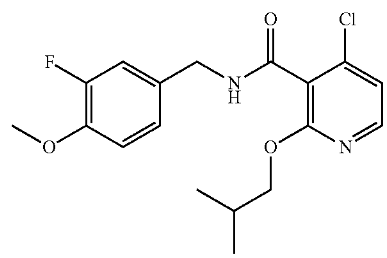 |
| 184 | 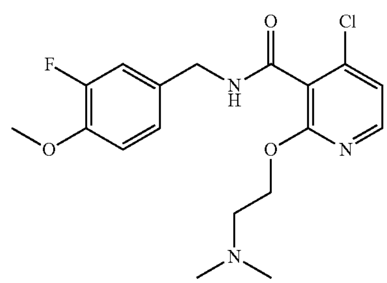 [SMILES: COc1ccc(CNC(=O)c2c(Cl)ccnc2OCCN(C)C)cc1F] |
| 185 | 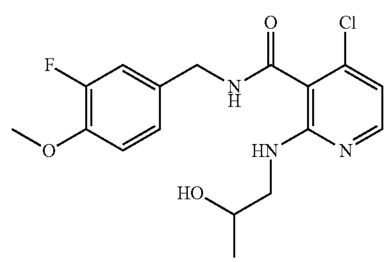 |

| Compound no. | Structure |
|---|---|
| 186 | 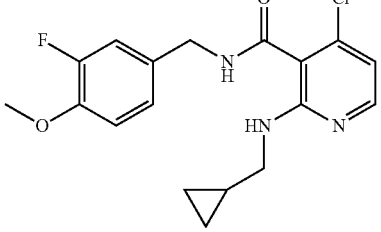 |
| 187 | 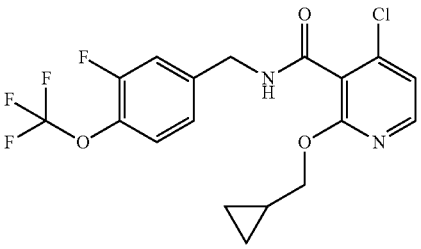 [SMILES: O=C(NCc1ccc(OC(F)(F)F)c(F)c1)c1c(Cl)ccnc1OCC1CC1] |
| 188 | 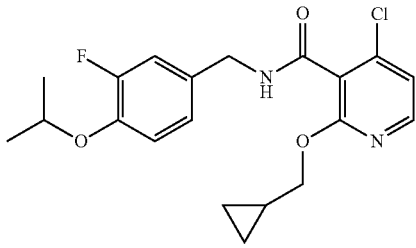 [SMILES: CC(C)Oc1ccc(CNC(=O)c2c(Cl)ccnc2OCC2CC2)cc1F] |
| 189 | 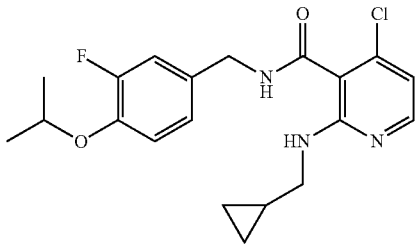 |
| 190 | 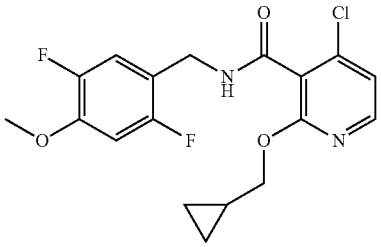 [SMILES: COc1cc(F)c(CNC(=O)c2c(Cl)ccnc2OCC2CC2)cc1F] |
| 191 | 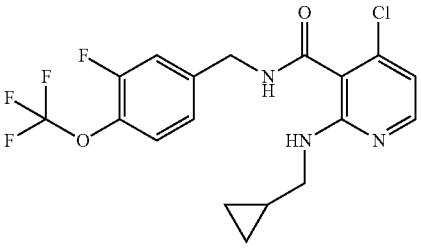 [SMILES: O=C(NCc1ccc(OC(F)(F)F)c(F)c1)c1c(Cl)ccnc1NCC1CC1] |
| Compound no. | Structure |
|---|---|
| 192 | 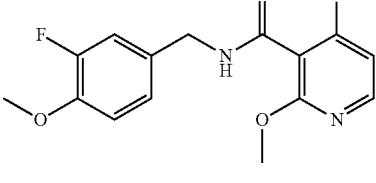 |
| 193 | 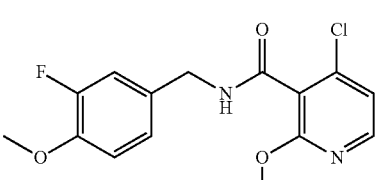 |
| 194 | 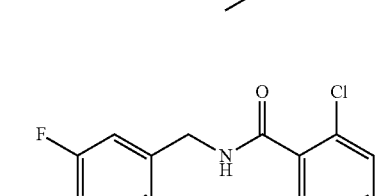 |
| 195 | 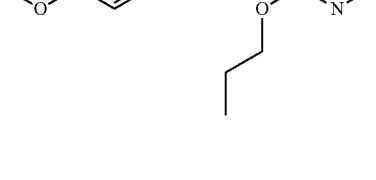 |
| 196 | 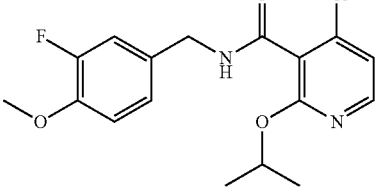 |
| 197 | 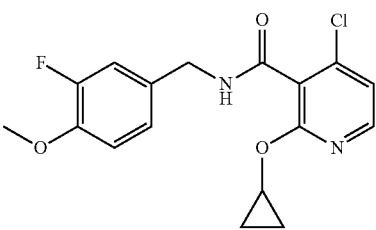 [SMILES: COc1ccc(CNC(=O)c2c(Cl)ccnc2OC2CC2)cc1F] |

-continued
| Compound no. | Structure |
|---|---|
| 198 | 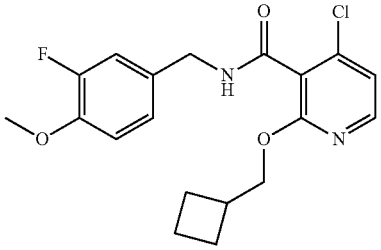 |
| 199 | 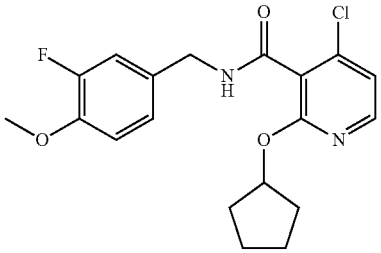 [SMILES: COc1ccc(CNC(=O)c2c(Cl)ccnc2OC2CCCC2)cc1F] |
| 200 | 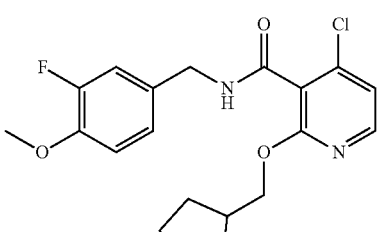 |
| 201 | 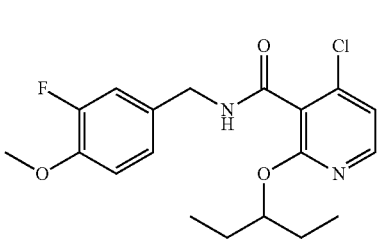 [SMILES: CCC(CC)Oc1nccc(Cl)c1C(=O)NCc1ccc(OC)c(F)c1] |
| 202 | 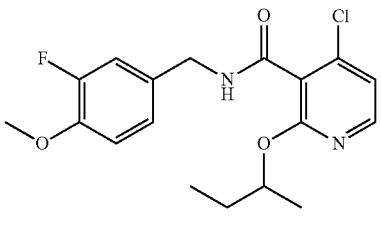 [SMILES: CCC(C)Oc1nccc(Cl)c1C(=O)NCc1ccc(OC)c(F)c1] |
| 203 | 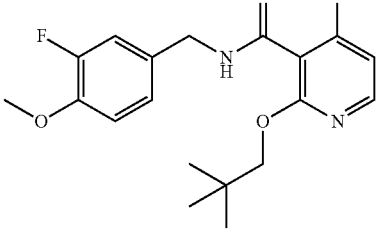 |
-continued
| Compound no. | Structure |
|---|---|
| 204 | 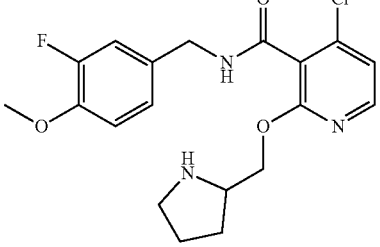 |
| 205 | 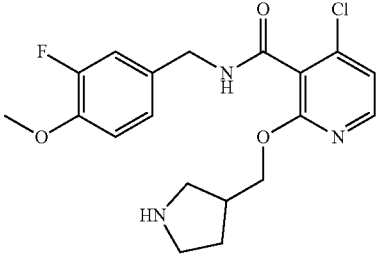 [SMILES: COc1ccc(CNC(=O)c2c(Cl)ccnc2OCC2CCCC2)cc1F] |
| 206 | 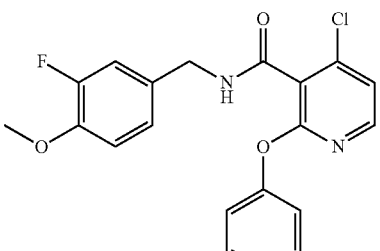 |
| 207 | 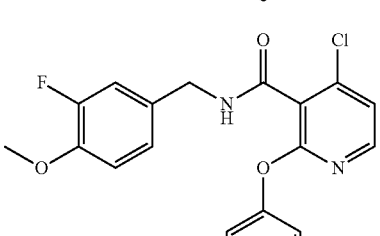 |
| 208 | 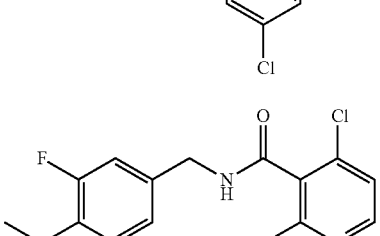 |
| 209 | 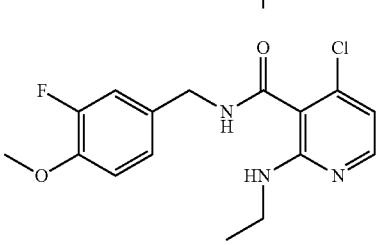 |

-continued

| Compound no. | Structure |
|---|---|
| 210 | (structure) |
| 211 | (structure) |
| 212 | (structure) |
| 241 | (structure) |
| 242 | (structure) |
| 243 | (structure) |

-continued

| Compound no. | Structure |
|---|---|
| 247 | (structure) |
| 248 | (structure) |
| 249 | (structure) |
| 250 | (structure) |
| 252 | (structure) |
| 256 | (structure) |

| Compound no. | Structure |
|---|---|
| 269 | 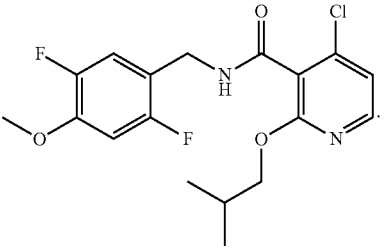 |
37. The method of claim 1, wherein the compound or a pharmaceutically acceptable salt or solvate thereof is:
(Compound 161)
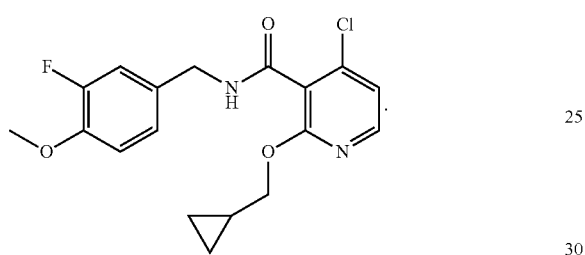
* * * * *